United States Patent
Albitar

(10) Patent No.: US 12,153,049 B2
(45) Date of Patent: Nov. 26, 2024

(54) BCR-ABL VARIANTS

(71) Applicant: Quest Diagnostics Investments LLC, Secaucus, NJ (US)

(72) Inventor: Maher Albitar, Coto De Caza, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 24 days.

(21) Appl. No.: 17/694,306

(22) Filed: Mar. 14, 2022

(65) Prior Publication Data

US 2022/0196665 A1 Jun. 23, 2022

Related U.S. Application Data

(63) Continuation of application No. 16/989,125, filed on Aug. 10, 2020, now Pat. No. 11,275,088, which is a continuation of application No. 15/643,937, filed on Jul. 7, 2017, now Pat. No. 10,739,345, which is a continuation of application No. 12/472,319, filed on May 26, 2009, now Pat. No. 9,702,877.

(60) Provisional application No. 61/110,512, filed on Oct. 31, 2008.

(51) Int. Cl.
- *C12Q 1/6883* (2018.01)
- *A61K 31/497* (2006.01)
- *A61K 31/506* (2006.01)
- *C07K 14/82* (2006.01)
- *C12N 9/12* (2006.01)
- *G01N 33/574* (2006.01)

(52) U.S. Cl.
CPC ..... *G01N 33/57426* (2013.01); *A61K 31/497* (2013.01); *A61K 31/506* (2013.01); *C07K 14/82* (2013.01); *C12N 9/12* (2013.01); *C12Q 1/6883* (2013.01); *C07K 2319/00* (2013.01); *C12Q 2600/106* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,798,885 A | 1/1989 | Mason et al. |
| 4,874,853 A | 10/1989 | Rossi |
| 4,946,778 A | 8/1990 | Ladner et al. |
| 4,952,496 A | 8/1990 | Studier et al. |
| 5,057,410 A | 10/1991 | Kawasaki et al. |
| 5,963,456 A | 10/1999 | Klein et al. |
| 6,001,230 A | 12/1999 | Burolla |
| 6,217,731 B1 | 4/2001 | Kane et al. |
| 6,329,179 B1 | 12/2001 | Kopreski |
| 6,582,908 B2 | 6/2003 | Fodor et al. |
| 6,773,882 B2 | 8/2004 | Hogan et al. |
| 6,849,400 B1 | 2/2005 | Harvey et al. |
| 6,916,634 B2 | 7/2005 | Kopreski |
| 6,939,671 B2 | 9/2005 | Kopreski |
| 7,521,213 B2 | 4/2009 | Hantash |
| 7,585,626 B1 | 9/2009 | Hantash et al. |
| 8,603,740 B2 | 12/2013 | Ma |
| 9,488,656 B2 | 11/2016 | Albitar et al. |
| 9,593,378 B2 | 3/2017 | Ma |
| 9,702,877 B2 | 7/2017 | Albitar |
| 9,957,574 B2 | 5/2018 | Ma |
| 10,093,980 B2 | 10/2018 | Albitar et al. |
| 2003/0148345 A1 | 8/2003 | Kopreski |
| 2003/0158105 A1 | 8/2003 | Sawyers et al. |
| 2004/0106140 A1 | 6/2004 | Thill |
| 2005/0176101 A1 | 8/2005 | West |
| 2005/0202519 A1 | 9/2005 | Barthe et al. |
| 2006/0269956 A1 | 11/2006 | Sawyers et al. |
| 2006/0292576 A1 | 12/2006 | Albitar et al. |
| 2007/0083334 A1 | 4/2007 | Mintz et al. |
| 2010/0113470 A1 | 5/2010 | Albitar |

FOREIGN PATENT DOCUMENTS

| | | |
|---|---|---|
| EP | 0 367 76 A2 | 9/1981 |
| EP | 0 117 060 A3 | 8/1984 |
| EP | 0 117 058 B1 | 9/1989 |
| GB | 2 211 504 A | 7/1989 |
| WO | WO-2009/029321 A2 | 3/2009 |

(Continued)

OTHER PUBLICATIONS

Chiarella (Current Molecular Medicine 2012 vol. 12 p. 547). (Year: 2012).*
"Chemotherapy Drugs"; STI-571, 2005[online][retrieved on May 19, 2010], Available on the Internet: <URL: http://www.chemocare.com/bio/sti.asp >.
ABI prism user bulletin #5 (1998).
Abravaya, et al., "Detection of point mutations with a modified ligase chain reaction (Gap-LCR)"; Nucleic Acids Research 23:675-682, 1995.
Albitar, M. et al., "Free circulating soluble CD52 as a tumor marker in chronic lymphocytic leukemia and its implication in therapy with anti-CD52 antibodies"; Cancer 101, 999-1008 (2004).

(Continued)

*Primary Examiner* — Katherine D Salmon
(74) *Attorney, Agent, or Firm* — Foley & Lardner LLP

(57) ABSTRACT

A splice variant of bcr-abl mRNA that produces BCR-ABL protein with a truncated C-terminus and its role in resistance to treatment with kinase inhibitors is disclosed. Vectors for expressing the truncated gene product are provided as well as recombinant cells that express the truncated gene product from a cDNA construct. Also provided are methods compositions and kits for detecting the BCR-ABL splice variant. Additionally, methods for screening BCR-ABL kinase domain inhibitors which rely on the recombinant cells and methods of predicting likelihood for resistance of a CML patient with a BCR/ABL translocation respond to treatment with one or more BCR-ABL kinase inhibitors are also disclosed.

6 Claims, 30 Drawing Sheets

Specification includes a Sequence Listing.

(56) References Cited

FOREIGN PATENT DOCUMENTS

WO    WO-2009/061890    5/2009

OTHER PUBLICATIONS

Aldea et al., "Rapid detection of herpes simplex virus DNA in genital ulcers by real-time PCR using SYSBR green 1 dye as the detection signal"; J. Clin. Microbiol. 40(3):1060-1062 (2002).
Alderborn et al., "Determination of Single-Nucleotide Polymorphisms by Real-time Pyrophosphate DNA Sequencing"; Genome Res. (2000), 10:1249-1265.
Antony et al., "A Molecular Beacon Strategy for the Thermodynamic Characterization of Triplex DNA: Triplex formation at the promoter Region of Cyclin D1"; Biochemistry, 40:9387-9395 (2001).
Azam et al., "Activity of dual SRC-ABL inhibitors highlights the role of BCR/ABL kinase dynamics in drug resistance"; PNAS, 103(24):9244-9249 (2006).
Bao et al., "SNP identification in unamplified human genomic DNA with gold nanoparticle probes"; Nucleic Acids Research, 33:e15 (2005).
Bolufer et al., "Rapid quantitative detection of BCR-ABL transcripts in chronic myeloid leukemia patients by real-time reverse transcriptase polymerase-chain reaction using fluorescently labeled probes," Haematologica, vol. 85, pp. 1248-1254, Dec. 2000.
Boom, et al., "Rapid and simple method for purification of nucleic acids"; J Clin Micro 28:495-503, 1990.
Boom, et al., "Rapid purification of hepatitis B virus DNA from serum"; J Clin Micro 29:1804-1811, 1991.
Bradeen et al., "Comparison of imatinib mesylate, dasatinib (BMS-354825), and nilotinib (AMN107) in an N-ethyl-N-nitrosourea (ENU)-based mutagenesis screen: high efficacy of drug combinations"; Blood, 108:2332-2338 (2006).
Branford et al., "Detection of BCR-ABL mutations in patients with CML treated with imatinib is virtually always accompanied by clinical resistance, and mutations in the ATP phosphate-binding loop (P-loop) are associated with a poor prognosis"; Blood, 102:276-283 (2003).
Branford et al., "High frequency of point mutations clustered within the adenosine triphosphate-binding region of BCR/ABL in patients with chronic myeloid leukemia or Ph-positive acute lymphoblastic leukemia who develop imatinib (ST1571) resistance"; Blood, 99:3472-3475 (2002).
Branford et al., "Real-time quantitative PCR analysis can be used as a primary screen to identify patients with CML treated with imatinib who have BCR-ABL kinase domain mutations"; Blood, vol. 104, No. 9, Nov. 1, 2004 (Nov. 1, 2004), pp. 2926-2932.
Bubnoff et al., "Resistance of Philadelphia-chromosome positive leukemia towards the kinase inhibitory imatinib (STI571, Glivec); a targeted oncoprotein strikes back", Leukemia, vol. 17, 2003, pp. 829-838.
Buchman, et al., A., "Selective RNA amplification: A novel method using dUMP-containing primers and uracil DNA glycosylase"; PCR Methods Applic 3:28-31, 1993.
Buck et al., Design Strategies and Performance of Custom DNA Sequencing Primers, BioTechniques, 1999, 27:528-536.
Burgess et al., "Comparative analysis of two clinically active BCR-ABL kinase inhibitors reveals the role of conformation-specific binding in resistance"; PNAS, 102(9):3395-3400 (2005).
Caceres et al., "Alternative splicing: multiple control mechanisms and involvement in human disease"; Trends in Genetics 2002 18:186-193.
Capdeville et al., "Glivec (STI571, Imatinib), a Rationally Developed, Targeted Anticancer Drug"; Nat. Rev. Drug Discov., 1:493 (2002).
Catovsky D., "Ph1 positive acute leukemia and chronic granulocytic leukemia: one or two disease"; Br. J. Haematol 42: 493-498 (1979).
Chang et al., "Phenotypic expression in E. coli of a DNA sequence coding for mouse dihydrofolate reductase"; Nature (1978), 275:617-624.

Cheung, et al., "Rapid and sensitive method for detection of hepatitis C virus RNA by using silica particles"; J Clin Micro 32:2593-2597, 1994.
Chirgwin, et al., "Isolation of biologically active ribonucleic acid from sources enriched in ribonuclease"; Biochemistry 18:5294-5299, 1979.
Chomczynski and Mackey, "Modification of the TRI reagent$2122 procedure for isolation of RNA from polysaccharide- and proteoglycan-rich sources"; BioTechniques 19:942-945, 1995.
Chomczynski and Mackey, "Substitution of choroform by bromo-chloropropane in the single-step method of RNA isolation"; Analytical Biochemistry 225:163-164, 1995.
Chomczynski and Sacchi, "Single-step method of RNA isolation by acid guanidinium thiocyanate-phenol-chloroform extraction"; Analytical Biochemistry 162:156-159, 1987.
Chomczynski, "A reagent for the single-step simultaneous isolation of RNA, DNA and proteins from cell and tissue samples"; Biotech 15:532-537, 1993.
Chu et al., "Dasatinib in Chronic Myelogenous Leukemia"; N. Engl. J. Med., 355:1062-1064, (2006).
Clark S. S. et al., "Unique forms of the abl tryrosine kinase distinguish PH-positive CML from PH-positive ALL"; Science 235:85-88, (1987).
Cole et al., "The EBV-Hybridoma Technique and Its Application to Human Lung Cancer, Monoclonal Antibodies and Cancer Therapy"; Alan R. Liss, Inc., pp. 77-96 (1985).
Cote, Richard J. et al., "Generation of human monoclonal antibodies reactive with cellular antigens"; Proc. Natl. Acad. Sci., (Apr. 1983), vol. 80, pp. 2026-2030.
Cross, et al., "Competitive polymerase chain reaction to estimate the number of BCR-ABL transcripts in chronic myeloid leukemia patients after bone marrow transplantation"; Blood 82: 1929-36, (1993).
Curvo et al., "A recurrent splicing variant without c-ABL Exon 7 in Imatinib-resistant patients"; Leukemia Research, Mar. 2008, 32:508-510, entire document.
Deboer et al., "The tac promoter: A functional hybrid derived from the trp and lac promoters"; Proc. Natl. Acad. Sci. USA, vol. 80, pp. 21-25, Jan. 1983.
Deininger et al., "The Tyrosine Kinase Inhibitor CGP57148B Selectively Inhibits the Growth of BCR-ABL-Positive Cells"; Blood, 90: 3691-3698 (1997).
Deininger, et al., "The development of imatinib as a therapeutic agent for chronic myeloid leukemia"; Blood 105:2640-53 (2005).
Dhingra et al., "Hybridization Protection Assay: A Rapid, Sensitive, and Specific Method for Detection of Philadelphia Chromosome-Positive Leukemias"; Blood, Jan. 15, 1991, 77(2):238-242.
Dieffenbach et al., "General concepts for PCR primer design," PCR Methods Appl., 1993, 3:s30-s37.
Donato, N.J., "BCR-ABL independence and LYN kinase overexpression in chronic myelogenous leukemia cells selected for resistance to STI571"; Blood, 101: 690-698 (2003).
Drexler, H.G., "The Leukemia-Lymphoma Cell Line Factsbook (2000)"; Academic Press.
Duffaud et al., "Expression and Secretion of Foreign Proteins in Escherichia coli"; Meth. in Enzymology, 153:492-507, 1987.
Eder et al., "Monitoring of BCR-ABL expression using Real-time RT-PCR in CML after bone marrow or peripheral blood stem cell transplantation"; Leukemia 13:1383-1389 (1999).
Elefanty et al., "bcr-abl, the hallmark of chronic myeloid leukaemia in man, induces multiple haemopoietic neoplasms in mice"; EMBO J., 9(4):1069-1078 (1990).
Emig et al., "Accurate and rapid analysis of residual disease in patients with CML using specific fluorescent hybridization probes for real time quantitative RT-PCR"; Leukemia, 13:1825-1832, 1999.
Ercolani et al., "Isolation and complete sequence of a functional human Glyceraldehyde 3 phosphate dehydrogenase gene"; J. Biol. Chem. 263(30):15335-15341 (1988).
Erlich, H., "PCR Technology, Principles and Application for DNA Amplifications"; 1989.
Ernst et al., "Dynamics of BCR-ABL mutated clones prior to hematologic or cytogenetic resistance to Imatinib"; Haematologica, February (2008), 93(2):186-192 entire document.

(56) References Cited

OTHER PUBLICATIONS

Evans et al., "Pharmacogenomics: Translating Functional Genomics into Rational Therapeutics"; Science, vol. 286:487-491 (1999).
Final Office Action in U.S. Appl. No. 12/472,319 dated Nov. 2, 2012.
Final Office Action in U.S. Appl. No. 12/892,679 dated Jan. 28, 2014.
Final Office Action on U.S. Appl. No. 15/952,436 DTD Mar. 18, 2020.
Fiser, A. & Sali, A., "Modeller: Generation and Refinement of Homology-Based Protein Structure Models"; Methods Enzymol., 374: 461-491 (2003).
Fournie, et al., "Recovery of nanogram quantities of DNA from plasma and quantitative measurement using labeling by nick translation"; Analytical Biochemistry 158:250-256, 1986.
Galea-Lauri, "Immunological weapons against acute myeloid leukaemia"; Immunology (2002); 107:20-27.
GenBank Accession No. U07563.1, Human Proto-oncogene tyrosine-protein kinase (ABL) gene, exon 1a and exons 2-10, complete cds, printed Aug. 8, 2012, 33 pages.
GenBank Record G03845, human STS WI-3568, sequence tagged site, Oct. 19, 1995, 1 page.
Gething et al., "Cell-surface expression of influenza haemagglutinin from a cloned DNA copy of the RNA Gene"; Nature (1981), 293:620-625.
Gibson et al., "A novel method for real-time quantitative RT-PCR"; Genomic Res. 6: 995-1001 (1996).
Goeddel et al., "Direct expression in *Escherichia coli* of a DNA sequence coding for human growth hormone"; Nature (1979), 281:544-548.
Gorre et al., "BCR-ABL point mutants isolated from patients with imatinib mesylate-resistant chronic myeloid leukemia remain sensitive to inhibitors of the BCR-ABL chaperone heat shock protein 90"; Blood, 100: 3041-3044 (2002).
Gorre et al., "Clinical Resistance to STI-571 Cancer Therapy Caused by BCR-ABL Gene Mutation or Amplification"; Science, 293: 876-880 (2001).
Gruber et al., "A novel Bcr-Abl splice isoform is associated with the L248V mutation in CML patients with acquired resistance to imatinib"; Leukemia, Nov. 2006 vol. 20 No. 11, pp. 2057-2060.
Guilhot, F., and Roy, L., "Chronic myeloid leukemia" in Textbook of Malignant Hematology Ch. 41, pp. 696-734, 2nd Ed. (Degos et al., eds), Taylor and Francis Medical Books, 2005.
Gumireddy et al., "A non-ATP-competitive inhibitor of BCR-ABL overrides imatinib resistance"; PNAS, 102:1992, 2005.
Hamaguchi et al., "Aptamer Beacons for the Direct Detection of Proteins"; Analytical Biochemistry 294:126-131 (2001).
Hariharan et al., "cDNA sequence for human BCR, the gene that translocates to the abl oncogene in chronic myeloid leukemia"; EMBO J. 6(1):115-119 (1987).
Hay et al., "Bone Morphogenetic Protein Receptor IB Signaling Mediates Apoptosis Independently of Differentiation in Osteoblastic Cells"; J. Biol. Chem., 279: 1650-1658 (2004).
Heid et al., Real Time Quantitative PCR, Genome Res 6:986-994, 1996.
Hitzeman et al., "Isolation and Characterization of the Yeast 3-Phosphoglycerokinase Gene (PGK) by and Immunological Screening Technique"; J. Biol. Chem, (1980), 255:12073-12080.
Hochhaus et al., "Hematologic and Cytogenic Response Dynamics to Nilotinib (AMN107) Depend on the Type of BCR-ABL Mutations in Patients with Chronic Myelogenous Leukemia (CML) after Imatinib Failure"; Blood, 108: 225a (2006).
Hochhaus et al., "Molecular and chromosomal mechanisms of resistance to imatinib (STI571) therapy"; Leukemia, 16: 2190-2196 (2002).
Hoelzer, D. and Gokbuget, N., "Acute lymphoblastic leukemia in adults" in Textbook of Malignant Hematology Ch. 32, pp. 500-520, 2nd Ed. (Degos et al., eds), Taylor and Francis Medical Books, 2005.

Holland et al., "Isolation and Identification of Yeast Messenger Ribonucleic Acids Coding for Enolase, Glyceraldehyde-3-Phosphate Dehydrogenase and Phosphoglycerate Kinase"; Biochemistry (1978), 17:4900-4907.
Hughes et al., "Monitoring CML patients responding to treatment with tyrosine kinase inhibitors: review and recommendations for harmonizing current methodology for detecting BCR-ABL transcripts and kinase domain mutations and for expressing results"; Blood, 108: 28-37 (2006).
Huse et al., "Generation of a Large Combinatorial Library of the Immunoglobulin Repertoire in Phage Lambda"; Science, 1989; 246:1275-1281.
Imai, et al., "Detection of HIV-1 RNA in heparinized plasma of HIV-1 seropositive individuals"; J Virol Methods 36:181-184, 1992.
International Search Report dated Apr. 15, 2011 in application PCT/US2010/058987.
International Search Report dated Nov. 8, 2010 in application PCT/US2010/50539.
International Search Report dated Jun. 7, 2010 in application PCT/US2009/061539.
Iqbal et al., "Two different point mutations in ABL gene ATP-binding domain conferring Primary Imatinib resistance in a Chronic Myeloid Leukemia (CML) patient: A case report"; Biol. Proced. Online, vol. 6, No. 1, pp. 144-148, Jul. 2004.
Juppner, "Functional Properties of the PTH/PTHrP Receptor", Bone, Aug. 1995, vol. 17, No. 2 Supplement, pp. 39S-42S.
Kaboev et al., "PCR hot start using primers with the structure of molecular beacons (hairpin-like structure)"; Nucleic Acids Research 28(21):e94 (2000).
Kampke et al., "Efficient primer design algorithms"; Bioinformatics, 17:214-225, (2000).
Kanehisa, M., "Use of Statistical Criteria for Screening Potential Homologies in Nucleic Acid Sequences"; Polynucleotides Res. (1984), 12(1):203-213.
Kantarjian, et al., "Quantitative polymerase chain reaction monitoring of BCR-ABL during therapy with imatinib mesylate (STI571; gleevec) in chronic-phase chronic myelogenous leukemia"; Clin. Cancer Res. 9, 160-6 (2003).
Karet, et al., "Quantification of mRNA in human tissue using fluorescent nested reverse-transcriptase polymerase chain reaction"; Analytical Biochemistry 220:384-390, 1994.
Kaspers, GJL and Ravindranath, Y., "Acute myeloid leukemia in children and adolescents" in Textbook of Malignant Hematology Ch. 37, pp. 617-632, 2nd Ed. (Degos et al., eds), Taylor and Francis Medical Books, 2005.
Kawasaki et al., "Diagnosis of chronic myelogenous and acute lymphocytic by detection of leukemia-specific mRNA sequences in vitro"; Proc. Natl. Acad. Sci USA 85: 5698-5702 (1988).
Kievits et al., "NASBA$2122 isothermal enzymatic in vitro nucleic acid amplification optimized for the diagnosis of HIV-1 infection"; J Virological Methods 35:273-286, 1991.
Kingsman et al., "Replication in *Saccharomyces cerevisiae* of Plasmid pBR313 Carrying DNA from the Yeast trpl Region," Oct. 1979, Gene, vol. 7, Issue 2, pp. 141-152.
Klein et al., "BCR-ABL 1 induces aberrant splicing of IKAROS and lineage infidelity in pre-B lymphoblastic leukemia cells"; Oncogene, Feb. 16, 2006, 25(7):1118-1124 entire document.
Kohler et al., "Continuous cultures of fused cells secreting antibody of predefined specificity"; Nature, 1975, 256:495-497.
Komarova et al., "Combination of Two but Not Three Current Targeted Drugs Can Improve Therapy of Chronic Myeloid Leukemia"; PLoS One, 4(2) e4423:1-5 (2009).
Konopka J.B. et al., "An alternative of the human c-abl protein in K562 leukemia cells unmasks associated Tyrosine kinase activity"; Cell 37:1035-1042 (1984).
Kozbor, Danuta et al., "The Production of Monoclonal antibodies from human lymphocytes"; Immunology Today, (1983), vol. 4(3), pp. 72-79.
Kreuzer et al., "Applicability of an Absolute Quantitative Procedure to Monitor Intra-Individual bcr/abl Transcript Kinetics in Clinical Samples from Chronic Myelogenous Leukemia Patients"; Int. J. Cancer: 86:741-746 (2000).

(56) References Cited

OTHER PUBLICATIONS

Kuroda et al., "Bim and Bad mediate imatinib-induced killing of BCR/ABL+ leukemic cells, and resistance due to their loss is overcome by a BH3 mimetic"; Proc. Natl. Acad. Sci., U.S.A. 103:14097 (2006).
Kurzrock et al., "The Molecular Genetics of Philadelphia Chromosome-Positive Leukemias"; N. Engl. J. Med., 319: 990-998 (1988).
Larkin et al., "Clustal W and Clustal X version 2.0, Bioinformatics"; 23:2947-2948 (2007).
Laudadio et al.,—Consultations in Molecular Diagnostics—"An Intron-Derived Insertion/Truncation Mutation in the BCR-ABL Kinase Domain in Chronic Myeloid Leukemia Patients Undergoing Kinase Inhibitor Therapy"; Journal of Molecular Diagnostics, Mar. 2008, vol. 10, No. 2, p. 177-180.
Lee et al., "Age-related telomere length dynamics in peripheral blood mononuclear cells of healthy cynomolgus monkeys measured by Flow FISH"; Immunology, 105:458-465, (2002).
Lee et al., "BCR-ABL alternative splicing as a common mechanism for imatinib resistance: evidence from molecular dynamics simulations"; Mol. Cancer Ther. 7(12):3834-3841 (2008).
Lerma et al., "Novel compounds with antiproliferative activity against imatinib-resistant cell lines"; Mol. Cancer Ther., 6(2): 655$201366 (2007).
Lesniak et al., "Calcyclin (S100A6) expression is stimulated by agents evoking oxidative stress via the antioxidant response element," Biochimica et Biophysica Acta, 2005, 1744:29-37.
Levinson et al., "A Src-Like Inactive Conformation in the Abl Tyrosine Kinase Domain"; PLoS Biol., 4: e144 (2006).
Lin et al., "Proliferation and apoptosis in acute and chronic leukemias and myelodysplastic syndrome"; Leuk Res., 26(6):551-9 (2002).
Lowe et al., A computer program for selection of oligonucleotide primers for polymerase chain reactions, Nucleic Acids Research, 1990, 18(7):1757-1761.
Lozzio, C.B. and Lozzio, B.B., "Human chronic myelogenous leukemia cell-line with positive Philadelphia chromosome"; Blood, 45(3):321-334 (1975).
Ma et al., "BCR-ABL Truncation due to Premature Translation Termination as a Mechanism of Resistance to Kinase Inhibitors"; Acta Haematol., 121:27-31 (2009).
Ma et al., "BCR-ABL Truncation due to Premature Translation Termination as a Mechanism of Resistance to Kinase Inhibitors," Acta Haematol., (2009), 121:27-31.
Ma et al., "Three Novel Alternative Splicing Mutations in BCR-ABL1 detected in CML Patients with Resistance to Kinase Inhibitors"; Blood (ASH Annual Meeting Abstracts), 2009, vol. 114, Abstract 1107.
Ma et al., "Three novel alternative splicing mutations in BCR-ABL 1 detected in CML patients with resistance to kinase inhibitors"; presented at 51st ASH annual meeting and exposition (2009).
Mahon, F.X., "Blood, Selection and characterization of BCR-ABL positive cell lines with differential sensitivity to the tyrosine kinase inhibitor STI571: diverse mechanisms of resistance"; 96:1070-1079 (2000).
Manley, P.W., "Imatinib: a selective tyrosine kinase inhibitor"; Eur. J. Cancer, 38: S19-S27 (2002).
Mantei et al., "Rabbit β-globin mRNA Production in mouse L cells transformed with cloned rabbit β-globin chromosomal DNA"; Nature, Sep. 6, 1979, 281:40-46.
Marasco et al., (ed.), "Intracellular Antibodies: Research and Disease Applications"; Springer-Verlag New York, Inc. (1998) (ISBN: 3540641513).
McKenzie et al., "Mutants of the Formyltetrahydrofolate interconversion pathway of *Saccharomyces cerevisiae*"; Genetics (1977), 86:85-102.
Melo, J.V. & Chuah, C., "Resistance to imatinib mesylate in chronic myeloid leukaemia"; Cancer Lett., 249:121-132 (2007).
Mensink et al., "Quantitation of minimal residual diseases in Philadelphia chromosome positive chronic myeloid leukemia patients using real time quantitative PCR"; British J. Haematology 102:768-774 (1998).
Moore, et al., "Design of PCR primers that detect only mRNA in the presence of DNA"; Nucleic Acids Res. 18:1921, 1991.
Morrison et al., "Chimeric human antibody molecules: Mouse antigen-binding domains with human constant region domains"; Proc. Natl. Acad. Sci. USA Nov. 1984, 81:6851-6855.
Mosmann, Tim, "Rapid Colorimetric Assay for Cellular Growth and Survival: Application to Proliferation and Cytotoxicity Assays"; J. Immunol. Meth. 1983; 65:55-63.
Mulligan et al., "Synthesis of rabbit β-globin in cultured monkey kidney cells following infection with a SV40 β-globin recombinant genome"; Nature, Jan. 11, 1979, vol. 277:108-114.
Mummidi et al., "Evolution of Human and Non-human Primate CC Chemokine Receptor 5 Gene and mRNA"; The Journal of Biological Chemistry, Jun. 2000, vol. 275, No. 25, pp. 18945-18961.
Nagar et al., "Crystal Structures of the Kinase Domain of c-Abl in Complex with the Small Molecule Inhibitors PD173955 and Imatinib (STI-571)"; Cancer Res., 62: 4236-4243 (2002).
Nagar, B., "Structural Basis for the Autoinhibition of C-Abl Tyrosine Kinase"; Cell, 112: 859-871 (2003).
NCBI GenBank Accession No. AB069693, *Homo sapiens* mRNA for bcr/abl e8a2 fusion protein, partial cds; http://www.ncbi.nlm.nih.gov/nuccore/AB069693.1?report=gbwithparts&log$=seqview, printed Aug. 8, 2012, 2 pages.
NCBI GenBank Accession No. AF113911, *Homo sapiens* BCR-ABL1 e1a2 chimeric protein (BCR/ABL fusion) mRNA, partial cds; http://www.ncbi.nlm.nih.gov/nuccore/AF113911.1?report=gbwithparts&log$=seqview, printed Aug. 8, 2012 2 pages.
NCBI GenBank Accession No. AF251769, *Homo sapiens* bcr/abl e1-a3 chimeric fusion protein (BCR/ABLe1-a3) mRNA, partial cds; http://www.ncbi.nlm.nih.gov/nuccore/AF251769.1?report=gbwithparts&log$=seqview, printed Aug. 8, 2012 1 page.
NCBI GenBank Accession No. AF487522, *Homo sapiens* BCRe18/ABL1e3 fusion protein (BCR/ABL fusion) mRNA, partial cds; http://www.ncbi.nlm.nih.gov/nuccore/AF487522.1?report=gbwithparts&log$=seqview, printed Aug. 8, 2012 1 page.
NCBI GenBank Accession No. AY789120, *Homo sapiens* BCR/ABL fusion mRNA sequence; http://www.ncbi.nlm.nih.gov/nuccore/AY789120.1?report=gbwithparts&log$=seqview, printed Aug. 8, 2012 1 page.
NCBI GenBank Accession No. DQ898313, *Homo sapiens* isolate e1a4 BCR/ABL fusion protein (BCR/ABL fusion) mRNA, partial cds, alternatively spliced; http://www.ncbi.nlm.nih.gov/nuccore/dq898313, printed Aug. 8, 2012 2 pages.
NCBI GenBank Accession No. DQ898314, *Homo sapiens* isolate e13a4 BCR/ABL fusion protein (BCR/ABL fusion) mRNA, partial cds, alternatively spliced; http://www.ncbi.nlm.nih.gov/nuccore/DQ898314.1?report=gbwithparts&log$=seqview, printed Aug. 8, 2012 2 pages.
NCBI GenBank Accession No. DQ898315, *Homo sapiens* isolate e14a4 BCR/ABL fusion protein (BCR/ABL fusion) mRNA, partial cds alternatively spliced; http://www.ncbi.nlm.nih.gov/nuccore/DQ898315.1?report=gbwithparts&log$=seqview, printed Aug. 8, 2012 2 pages.
NCBI GenBank Accession No. DQ912588. *Homo sapiens* BCR/ABL fusion protein e1a5 (BCR/ABL fusion) mRNA, partial cds, alternatively spliced; http://www.ncbi.nlm.nih.gov/nuccore/DQ912588.1?report=gbwithparts&log$=seqview, printed Aug. 8, 2012 1 page.
NCBI GenBank Accession No. DQ912589, *Homo sapiens* BCR/ABL fusion protein e13a5 (BCR/ABL fusion) mRNA, partial cds, alternatively spliced; http://www.ncbi.nlm.nih.gov/nuccore/DQ912589.1?report=gbwithaparts&log$=seqview, printed Aug. 8, 2012 1 page.
NCBI GenBank Accession No. DQ912590, *Homo sapiens* BCR/ABL fusion protein e14a5 (BCR/ABL fusion) mRNA, partial cds, alternatively spliced; http://www.ncbi.nlm.nih.gov/nuccore/DQ912590.1?report=gbwithparts&log$=seqview, printed Aug. 8, 2012 1 page.
NCBI GenBank Accession No. EF158045, *Homo sapiens* BCR/ABL p210 fusion protein (BCR/ABL fusion) mRNA, partial cds; http://www.ncbi.nlm.nih.gov/nuccore/EF158045.1?report=gbwithparts&log$=seqview, printed Aug. 8, 2012 1 page.
NCBI GenBank Accession No. EF423615, *Homo sapiens* BCR/ABL fusion protein (BCR/ABL fusion) mRNA, partial cds; http://www.ncbi.nlm.nih.gov/nuccore/EF423615?report=gbwithparts&log$=seqview, printed Aug. 8, 2012 1 page.

(56) References Cited

OTHER PUBLICATIONS

NCBI GenBank Accession No. EU216058, *Homo sapiens* BCR/ABL fusion protein isoform X1 (BCR/ABL fusion) mRNA, complete cds; http://www.ncbi.nlm.nih.gov/nuccore/EU216058.1?report=gbwithparts&log$=seqview, printed Aug. 8, 2012 2 pages.
NCBI GenBank Accession No. EU216059, *Homo sapiens* BCR/ABL fusion protein isoform X2 (BCR/ABL fusion) mRNA, complete cds; http://www.ncbi.nlm.nih.gov/nuccore/EU216059.1?report=gbwithparts&log$=seqview, printed Aug. 8, 2012 2 pages.
NCBI GenBank Accession No. EU216060, *Homo sapiens* BCR/ABL fusion protein isoform X3 (BCR/ABL fusion) mRNA, complete cds; http://www.ncbi.nlm.nih.gov/nuccore/Eu216060, printed Aug. 8, 2012 3 pages.
NCBI GenBank Accession No. EU216061, *Homo sapiens* BCR/ABL fusion protein isoform X4 (BCR/ABL fusion) mRNA, complete cds; http://www.ncbi.nlm.nih.gov/nuccore/Eu216061, printed Aug. 8, 2012 2 pages.
NCBI GenBank Accession No. EU216062, *Homo sapiens* BCR/ABL fusion protein isoform X5 (BCR/ABL fusion) mRNA, complete cds; http://www.ncbi.nlm.nih.gov/nuccore/Eu216062, printed Aug. 8, 2012 2 pages.
NCBI GenBank Accession No. EU216063, *Homo sapiens* BCR/ABL fusion protein isoform X6 (BCR/ABL fusion) mRNA, complete cds; http://www.ncbi.nlm.nih.gov/nuccore/Eu216063, printed Aug. 8, 2012 2 pages.
NCBI GenBank Accession No. EU216064, *Homo sapiens* BCR/ABL fusion protein isoform X7(BCR/ABL fusion) mRNA, complete cds; http://www.ncbi.nlm.nih.gov/nuccore/Eu216064, printed Aug. 8, 2012 2 pages.
NCBI GenBank Accession No. EU216065, *Homo sapiens* BCR/ABL fusion protein isoform X8 (BCR/ABL fusion) mRNA, complete cds; http://www.ncbi.nlm.nih.gov/nuccore/Eu216065, printed Aug. 8, 2012 2 pages.
NCBI GenBank Accession No. EU216066. *Homo sapiens* BCR/ABL fusion protein isoform X9 (BCR/ABL fusion) mRNA, complete cds; http://www.ncbi.nlm.nih.gov/nuccore/Eu216066, printed Aug. 8, 2012 3 pages.
NCBI GenBank Accession No. EU216067, *Homo sapiens* BCR/ABL fusion protein isoform Y1 (BCR/ABL fusion) mRNA, complete cds; http://www.ncbi.nlm.nih.gov/nuccore/Eu216067, printed Aug. 8, 2012 2 pages.
NCBI GenBank Accession No. EU216068, *Homo sapiens* BCR/ABL fusion protein isoform Y2 (BCR/ABL fusion) mRNA, complete cds; http://www.ncbi.nlm.nih.gov/nuccore/Eu216068, printed Aug. 8, 2012 2 pages.
NCBI GenBank Accession No. EU216069, *Homo sapiens* BCR/ABL fusion protein isoform Y3 (bcr/ABL fusion) mRNA, complete cds; http://www.ncbi.nlm.nih.gov/nuccore/Eu216069, printed Aug. 8, 2012 2 pages.
NCBI GenBank Accession No. EU216070, *Homo sapiens* BCR/ABL fusion protein isoform Y4 (BCR/ABL fusion) mRNA, complete cds; http://www.ncbi.nlm.nih.gov/nuccore/Eu216070; printed Aug. 8, 2012 2 pages.
NCBI GenBank Accession No. EU216071, *Homo sapiens* BCR/ABL fusion protein isoform Y5 (BCR/ABL fusion) mRNA, complete cds; http://www.ncbi.nlm.nih.gov/nuccore/Eu216071, printed Aug. 8, 2012 3 pages.
NCBI GenBank Accession No. EU236680, *Homo sapiens* BCR/ABL b3a3 fusion protein (BCR/ABL fusion) mRNA, partial cds; htt://www.ncbi.nlm.nih.gov/nuccore/eu236680, printed Aug. 8, 2012 2 pages.
NCBI GenBank Accession No. M14752, Human c-abl gene, complete cds; http://www.ncbi.nlm.nih.gov/nuccore/m14752, printed Aug. 8, 2012 2 pages.
NCBI GenBank Accession No. M15025, Human BCR/ABL mRNA (product of translocation t(22q11;9q34)), 5'end; www.ncbi.nlm.nih.gov/nuccore/m15025, printed Aug. 8, 2012, 2 pages.

NCBI GenBank Accession No. M17541, Human bcr/abl fusion protein (product of translocation t(22q11; 9q34)), exons 1 and 2; http://www.ncbi.nlm.nih.gov/nuccore/m17541, printed Aug. 8, 2012 1 page.
NCBI GenBank Accession No. M17542, Human bcr/abl protein gene (product of tranlocation t(22q11; 9q34)), exons 1 and 2, http://www.ncbi.nlm.nih.gov/nuccore/m17542, printed Aug. 8, 2012 1 page.
NCBI GenBank Accession No. M30829, Human bcr/abl fusion protein mRNA, partial cds, clone K28; http://www.ncbi.nlm.nih.gov/nuccore/m30829, printed Aug. 8, 2012 1 page.
NCBI GenBank Accession No. M30832, Human bcr/abl fusion protein, partial cds, clone E3; http://www.ncbi.nlm.nih.gov/nuccore/m30832, printed Aug. 8, 2012, 1 page.
NCBI GenBank Accession No. S72478, BCR . . . ABL {b3/a3 junction, translocation breakpoint} [human, Japanese CML patient 1 and ALL patient 2, peripheral blood, monoculear cells, mRNA Mutant, 3 genes, 140 nt]; http://www.ncbi.nlm.nih.gov/nuccore/s72478, printed Aug. 8, 2012 1 page.
NCBI GenBank Accession No. S72479, BCR . . . ABL {e1/a3 junction, translocation breakpoint} [human, Japanese ALL patient 3, bone marow, mononuclear cells, mRNA Mutant, 3 genes, 131 nt]. http://www.ncbi.nlm.nih.gov/nuccore/s72479, printed Aug. 8, 2012 1 page.
NCBI GenBank Accession Nos. EU216072, *Homo sapiens* BCR/ABL fusion protein isoform Y6 (BCR/ABL fusion) mRNA, complete cds; http://www.ncbi.nlm.nih.gov/nuccore/eu216072, printed Aug. 8, 2012 2 pages.
NCBI Protein Database Accession No. AAA35594, BCR-ABL protein, partial (*Homo sapiens*); http:www.ncbi.nlm.nih.gov/protein/AAA35594.1?report=gpwithparts&log$=seqview, printed Aug. 8, 2012 1 page.
NCBI Protein Database Accession No. ABX82702, BCR/ABL fusion protein isoform X3 [*Homo sapiens*]; http://www.ncbi.nlm.nih.gov/protein/abx82702, printed Aug. 8, 2012, 2 pages.
NCBI Protein Database Accession No. ABX82708, BCR/ABL fusion protein isoform X9 [*Homo sapiens*]; http://www.ncbi.nlm.nih.gov/protein/abx82708, printed Aug. 8, 2012, 2 pages.
NEB Catalog, New England Biolabs, 1996/1997 (1996), p. 111.
Neuberger et al., "Recombinant antibodies possessing novel effector functions"; Nature, Dec. 13, 1984, 312:604-608.
Non-Final Office Action in U.S. Appl. No. 12/472,319 dated Aug. 19, 2014.
Non-Final Office Action in U.S. Appl. No. 12/892,679 dated Aug. 5, 2013.
Non-Final Office Action in U.S. Appl. No. 13/512,945 dated Jan. 16, 2014.
Non-Final Office Action on U.S. Appl. No. 15/952,436 dated Oct. 4, 2019.
Non-Final Office Action on U.S. Appl. No. 16/153,094 DTD May 15, 2020.
Non-Final Office Action in U.S. Appl. No. 16/989,125 dated Jun. 17, 2021.
Notice of Allowance in U.S. Appl. No. 15/643,937 dated Apr. 10, 2020.
Notice of Allowance in U.S. Appl. No. 12/981,416 dated Aug. 9, 2013.
Notice of Allowance in U.S. Appl. No. 16/989,125 dated Nov. 3, 2021.
O'Hare et al., "AMN107: tightening the grip of imatinib"; Cancer Cell 7:117-9 (2005).
O'Hare et al., "Bcr-Abl kinase domain mutations, drug resistance, and the road to a cure for chronic myeloid leukemia"; Blood, 110:2242$20132249 (2007).
O'Hare et al., "Combined Abl Inhibitor Therapy for Minimizing Drug Resistance in Chronic Myeloid Leukemia: Src/Abl Inhibitors are Compatible with Imatinib"; Clin. Cancer Res., 11(19):6987-6993 (2005).
Okayama, "High-Efficiency Cloning of Full-Length DNA"; Mol. Cell. Biol. Feb. 1982, vol. 2:161-170.
Phillips G.J., "Green fluorescent protein—a bright idea for the study of bacterial protein localization"; FEMS Microbiol. Lett. 2001; 204(1):9-18.

(56) References Cited

OTHER PUBLICATIONS

Poddar, S.K. and Le, C.T., "Bordetella pertussis detection by spectrofluorometry using polymerase chain reaction (PCR) and a molecular beacon probe"; Molecular and Cellular Probes 15:161-167 (2001).
Priest et al., "Philadelphia chromosome positive childhood acute lymphocytic leukemia"; Blood 56: 15-22 (1980).
Quintas-Cardama et al., "Phase I/II study of subcutaneous homoharringtonine in patients with chronic myeloid leukemia who have failed prior therapy"; Cancer, (2006), 109(2):248-255.
Rao et al., "Genotyping single nucleotide polymorphisms directly from genomic DNA by invasive cleavage reaction on microspheres"; Nucleic Acids Research, 31(11):e66 (2003).
Rashtchian, "Amplification of RNA"; PCR Methods Applic 4:S83-S91, 1994.
Ren et al., "Abl protein-tyrosine kinase selects the Crk adapter as a substrate using SH3-binding sites"; Genes Dev., 8(7): 783-95 (1994).
Robertson and Walsh-Weller, "An Introduction to PCR Primer Design and Optimization of Amplification Reactions"; Methods of Mol. Biol., 98:121-126.
Rogers, et al., "Relative increase in leukemia-specific DNA in peripheral blood plasma from patients with acute myeloid leukemia and myelodysplasia"; Blood 103, 2799-2801 (2004).
Rothstein et al., "Chronic inhibition of superoxide dismutase produces apoptotic death of spinal neurons," PNAS USA, May 1994, 91:4155-4159.
Roux, K.H., "Optimization and troubleshooting in PCR," PCR Methods Appl., 1995, 4:s185-s194.
Rowley, J.D., "A New Consistent Chromosomal Abnormality in Chronic Myelogenous Leukaemia identified by Quinacrine Fluorescence and Giemsa Staining"; Nature, 243: 290-3 (1973).
Sambrook, J. et al., "Molecular Cloning: A Laboratory Manual (Dec. 1989)", Second Edition, Cold Spring Harbor Press, Plainview, NY.
Sanger et al., "DNA sequencing with chain-terminating inhibitors," PNAS USA, Dec. 1977, 74(12):5463-5467.
Shah et al., "Sequential ABL kinase inhibitor therapy selects for compound drug-resistant BCR-ABL mutations with altered oncogenic potency"; J. Clin. Invest., 117:2562-2569 (2007).
Shtivelman et al., "Alternative splicing of RNAs transcribed from the human abl gene and from the bcr-abl fused gene"; Cell, 47:277-284 (1986).
Smirnov, I. and Shafer, R.H., "Effect of Loop Sequence and Size on DNA Aptamer Stability"; Biochemistry 39:1462-1468 (2000).
Sooknanan, et al., "Detection and direct sequence identification of BCR-ABL mRNA in PH+ chronic myeloid leukemia"; Experimental Hematology 21:1719-1724, 1993.
Stinchcomb et al., "Isolation and Characterisation of a yeast chromosomal replicator"; Nature, Nov. 1, 1979, vol. 282, Issue 5734, pp. 39-43.
Stoilov et al., "Defects in Pre-mRNA Processing as Causes of and Predisposition to Diseases"; DNA and Cell Biology, 2002 21(11):803-818.
Stroun et al., "Neoplastic characteristics of the DNA found in the plasma of cancer patients"; Oncology 46:318-322, 1989.
Sun et al., "Modulation of the Cytotoxicity of 3'-Azido-3'-deoxythymidine and Methotrexate after Transduction of Folate Receptor cDNA into Human Cervical Carcinoma: Identification of a Correlation between Folate Receptor Expression and Thymidine Kinase Activity"; Cancer Res. Feb. 15, 1999; 59:940-946.
Takeda et al., "Construction of chimaeric processed immunoglobulin genes containing mouse variable and human constant region sequences"; Nature, Apr. 4, 1985, 314:452-454.
The Leukemia & Lymphoma Society, Fighting Blood Cancers, Facts 2009-2010, pp. 1-25.
Thomazy et al., "Use of plasma RNA for real-time quantitative RT-PCR to monitor imatinib therapy in patients with chronic myeloid leukemia"; Blood (ASH Annual Meeting Abstracts), 104: Abstract 1099, 2004.
Tokarski et al., "The structure of dasatinib (BMS-354825) bound to activated ABL kinase domain elucidates its inhibitory activity against imatinib-resistant ABL mutants"; Cancer Research, (2006), 66(11):5790-5797.
Tyagi et al., "Multicolor molecular beacons for allele discrimination"; Nature Biotechnology, Jan. 1998, 16:49-53.
Urdea et al., "Direct and quantitative detection of HIV-1 RNA in human plasma with a branched DNA signal amplification assay"; AIDS 7 (suppl 2):S11-S14, 1993.
Urdea, et al., "Branched DNA amplification multimers for the sensitive, direct detection of human hepatitis viruses"; Nucleic Acids Research Symposium Series 24:197-200, 1991.
Urlaub et al., "Isolation of Chinese hamster cell mutants deficient in dihydrofolate reductase activity"; Proc. Natl Acad. Sci. USA, Jul. 1980, pp. 4216-4220, vol. 77, No. 7.
US Final Office Action in U.S. Appl. No. 12/472,319 dated Dec. 20, 2016.
US Final Office Action in U.S. Appl. No. 14/076,324 dated Aug. 11, 2016.
US Final Office Action in U.S. Appl. No. 14/954,203 dated May 22, 2017.
US Notice of Allowance (Corrected) in U.S. Appl. No. 15/429,640 dated Jan. 24, 2018.
US Notice of Allowance in U.S. Appl. No. 12/472,319 dated Mar. 9, 2017.
US Notice of Allowance in U.S. Appl. No. 12/892,679 dated Jun. 21, 2016.
US Notice of Allowance in U.S. Appl. No. 14/076,324 dated Oct. 31, 2016.
US Notice of Allowance in U.S. Appl. No. 15/342,321 dated May 22, 2018.
US Notice of Allowance in U.S. Appl. No. 15/429,640 dated Dec. 27, 2017.
US Office Action dated Jan. 8, 2009 in U.S. Appl. No. 11/301,272.
US Office Action dated May 11, 2011 in U.S. Appl. No. 12/472,319.
US Office Action dated Nov. 12, 2009 in U.S. Appl. No. 11/301,272.
US Office Action dated Dec. 6, 2010 in U.S. Appl. No. 12/472,319.
US Office Action dated Mar. 14, 2012 in U.S. Appl. No. 12/472,319.
US Office Action dated Apr. 29, 2008 in U.S. Appl. No. 11/301,272.
US Office Action dated Jul. 6, 2011 in U.S. Appl. No. 11/301,272.
US Office Action in U.S. Appl. No. 12/472,319 dated Jul. 11, 2016.
US Office Action in U.S. Appl. No. 14/076,324 dated Apr. 18, 2016.
US Office Action in U.S. Appl. No. 14/954,203 dated Dec. 28, 2016.
US Office Action in U.S. Appl. No. 15/342,321 dated Oct. 4, 2017.
US Office Action in U.S. Appl. No. 15/429,640 dated Jul. 27, 2017.
US Office Action in U.S. Appl. No. 15/643,937 dated Feb. 6, 2019.
US Office Action in U.S. Appl. No. 11/301,272 dated Jun. 2, 2015.
US Office Action in U.S. Appl. No. 12/472,319 dated Jun. 3, 2015.
US Office Action in U.S. Appl. No. 12/892,679 dated Jun. 19, 2015.
US Office Action in U.S. Appl. No. 12/892,679 dated Sep. 30, 2014.
US Office Action in U.S. Appl. No. 13/512,945 dated Aug. 28, 2014.
Vandamme, et al., "Detection of HIV-1 RNA in plasma and serum samples using the NASBA amplification system compared to RNA-PCR"; J Virological Methods 52:121-132, 1995.
Volpe et al., "Alternative BCR/ABL Splice Variants in Philadelphia Chromosome—Positive Leukemias Result in Novel Tumor-Specific Fusion Proteins that May Represent Potential Targets for Immunotherapy Approaches"; Cancer Res, Jun. 1, 2007, 67(11):5300-5307.
Wang et al., "Primers are Decisive for Sensitivity of PCR"; Biotechniques, 17:82-85 (1994).
Wang, et al., "Quantitation of mRNA by the polymerase chain reaction"; Proc Natl Acad Sci USA 86:9717-9721, 1989.
Weisberg et al., "AMN107 (nilotinib): a novel and selective inhibitor of BCR-ABL"; Br. J. Cancer, 94:1765-1769 (2006).
Weisberg et al., "Beneficial effects of combining nilotinib and imatinib in preclinical models of BCR-ABL + leukemias"; Blood, 109:2112-2120 (2007).
Wertheim et al., "Localization of BCR-ABL to F-actin regulates cell adhesion but does not attenuate CML development"; Blood, Sep. 15, 2003, vol. 102, No. 6, pp. 2220-2228; from bloodjournal.hematologylibrary.org.

(56) References Cited

OTHER PUBLICATIONS

Wiedmann et al., "Ligase chain reaction (LCR) overview and applications"; Genome Res. 1994 3 S51-S64, downloaded from genome.cship.org on May 20, 2011.
Wiedmann et al., "Ligase Chain Reaction (LCR) Overview and Applications"; PCR Methods Appl. 3:S51-S64, (1994).
Wong et al., "Human GM-CSF: Molecular Cloning of the Complementary DNA and Purification of the Natural and Recombinant Proteins"; Science, 1985; 228:810-815.
Wong et al., "The BCR-ABL Story: Bench to Bedside and back"; Annu. Rev. Immunol. 2004; 22:247-306.
Wu et al., "Alternatively Spliced Genes"; Encyclopedia of Molecular and Cell Biology and Molecular Medicine, vol. 1, 2nd ed., 125-177 (2004).
Yamamoto, R. and Kumar, P.K.R., "Molecular beacon aptamer fluoresces in the presence of Tat protein of HIV-1"; Genes to Cells, 5:389-396 (2000).
Zhang et al., "Reproducible and inexpensive probe preparation for oligonucleotide arrays"; Nucleic Acids Research, 29(13):e66 (2001).
Zimmermann et al., "A simplified protocol for fast plasmid DNA sequencing"; Nucleic Acids Res. vol. 18, No. 4, p. 1067, Submitted Jan. 19, 1990, © 1990 Oxford University Press.

* cited by examiner

FIGURE 1

CATTTGGAGTATTGCTTTGGGAAATTGCTACCTATGGCATGTCCCCTTACCCGGG
AATTGACCTGTCCCAGGTGTATGAGCTGCTAGAGAAGGACTACCGCATGGAGCG
CCCAGAAGGCTGCCCAGAGAAGGTCTATGAACTCATGCgtaagccttcctcagcctgttctcacga
gtatatgtgggcattccaggaaattcaactgtgcaggagtgtgtacacaaagttgaaagttttttccatgagctctctccattccagttcttca
gatgcagctaatgtagccatttgctacctattgacctttatttacagataaatagtatgtgcgtgacttgtcttttaaagcaaaaatggtattga
tagataccaaacctgggtgtattcctaaatacagattcctgggccctgctttcacagacattctgctatagtagctaagctcatgaggtgat
ttttttttttttttttttttgagacggagtttcgctcttgtcgcccaggctggagtacaatggcgcaatgttggctcacttcaacctccacctccct
ggttcaagcgattctcctgcctcagcctcccaagtagctgggattacaggcatgcaccaccacgcccggctaattttgtatttttagtaga
gatggggtttctccatgttagtcaggctggtctccaactcccaacctcaggtgatctgcctgcctcggcctcccaaagtgctgcgattac
aggcgtgagccaccacgcccagctgcgaggtgattttatctggtcgttttatactgattacatatgtgttatctgtactatgcacacacag
gatgttttcatatatcttataaggtatttatatggccatttcttacactgttttcccacacatgtctttccacgtccatatattcagatctctccctct
ccctacctcttatttatgtatagctgcccagtactccatttcactcattcatccggtcctcttttgatgtgcatttggttgttttacacatttgtttg
gttttgcccttataaacaaagcagaaacaaatattcatgtacacgaatctctgggcactttggctggtatttctaaaagttgaactgttggtt
ccaagaactgtgtgggtttaaattttgatacatttaccaaactgttaaaaaaggttgtgccattgtatgctccagtcagacgcatatggga
gtgactgttcctggtccccagtactaggctttgtcagtctgtttagtcctcatgttagtctcattttcatgagaatttctttacttcag*ACTTT
GATAACCGTGAAGAAAGAACAAGATAGAAG*gtgagctgtttggcttagtaattttctacacctactagagcgg
gactgggaaaaatatatttgtaaatgcagttcttgctgtcactgtctctctggggttttacaatccatattcctgccagcatctaacgtctttc
aaattcttaatgtctataacaggacatgatgacattcatcgttttgacttgttgcagcaaaagatggttagcaggattggaatgttgctttcat
tctagacttttccttgagaactgctagccccgtattgctagccagatctcatggatgatctgacttgggtttcatctgtccagGTTGGC
AGTGGAATCCCTCTGACCGGCCCTCCTTTGCTGAAATCCACCAAGCCTTTGAAAC
AATGTTCCAGGAATCCAGTATCTCAGACG (SEQ ID NO: 3)

FIGURE 2 catttggagtattgctttgggaaattgctacctatggcatgtccccttacccgggaattgacctgtcccaggtgtatgagctgctagagaa
ggactaccgcatggagcgcccagaaggctgcccagagaaggtctatgaactcatgcgagcatACTTTGATAACCGT
GAAGAAAGAACAAGATAGAAGgttggcagtggaatccctctgaccggccctcctttgctgaaatccaccaagc
ctttgaaacaatgttccaggaatccagtatctcagacg (SEQ ID NO: 1)

Figure 3

```
              230        240        250        260        270
         |....|....|....|....|....|....|....|....|....|....
WT       MDPSSPNYDKWEMERTDITMKHKLGGGQYGEVYEGVWKKYSLTVAVKTLK
35INS    MDPSSPNYDKWEMERTDITMKHKLGGGQYGEVYEGVWKKYSLTVAVKTLK 280        290        300        310        320
         |....|....|....|....|....|....|....|....|....|....
WT       EDTMEVEEFLKEAAVMKEIKHPNLVQLLGVCTREPPFYIITEFMTYGNLL
35INS    EDTMEVEEFLKEAAVMKEIKHPNLVQLLGVCTREPPFYIITEFMTYGNLL 330        340        350        360        370
         |....|....|....|....|....|....|....|....|....|....
WT       DYLRECNRQEVSAVVLLYMATQISSAMEYLEKKNFIHRDLAARNCLVGEN
35INS    DYLRECNRQEVSAVVLLYMATQISSAMEYLEKKNFIHRDLAARNCLVGEN 380        390        400        410        420
         |....|....|....|....|....|....|....|....|....|....
WT       HLVKVADFGLSRLMTGDTYTAHAGAKFPIKWTAPESLAYNKFSIKSDVWA
35INS    HLVKVADFGLSRLMTGDTYTAHAGAKFPIKWTAPESLAYNKFSIKSDVWA 430        440        450        460        470
         |....|....|....|....|....|....|....|....|....|....
WT       FGVLLWEIATYGMSPYPGIDLSQVYELLEKDYRMERPEGCPEKVYELMRA
35INS    FGVLLWEIATYGMSPYPGIDLSQVYELLEKDYRMERPEGCPEKVYELMRA 480        490
         |....|....|....|....|...
WT       CWQWNPSDRPSFAEIHQAFETMFQ
35INS    YFD-NREERTR
```

FIGURE 5A
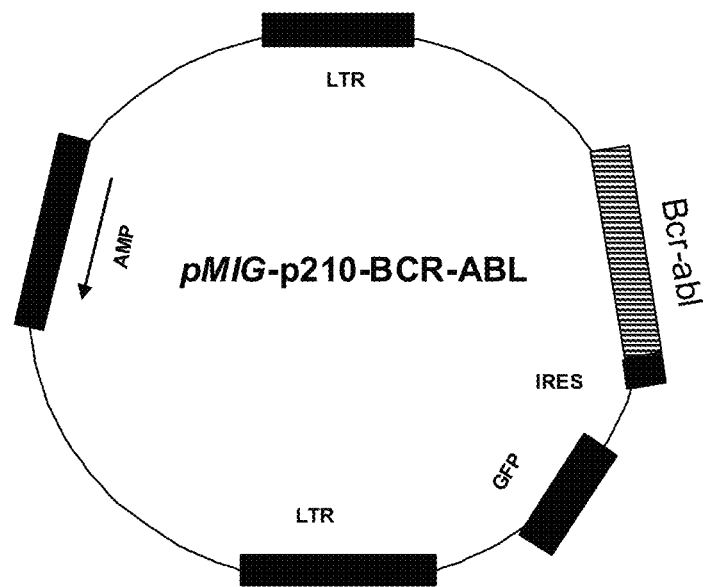
FIGURE 5B
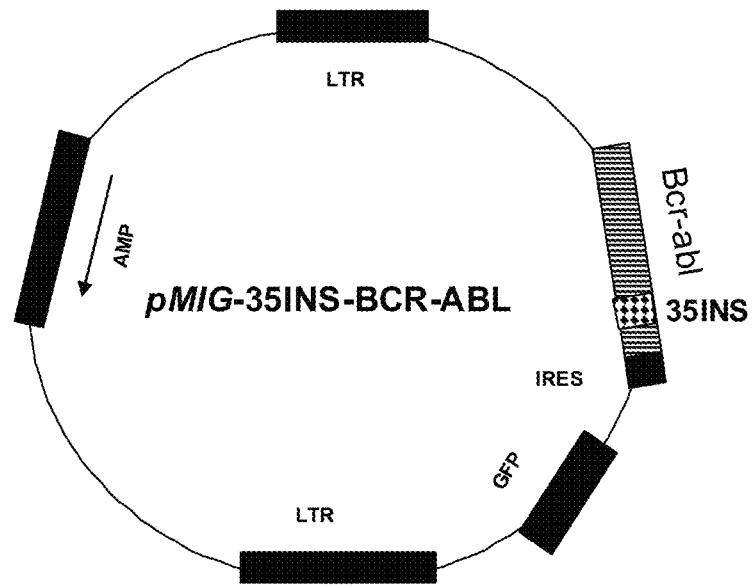

FIGURE 6

Relative frequency of individual BCR-ABL kinase domain mutations detected in patients

| Amino Acid Sequence of Wild-type BCR-ABL | Amino Acid Sequence of the Kinase Domain Mutant of BCR-ABL | % of Patients Having the Mutation |
|---|---|---|
| M 237 | M 237 I | <2% |
| M 244 | M 244 V | 2-10% |
| L 248 | L 248 V | <2% |
| G 250 | G 250 A | <2% |
| G 250 | G 250 E | 2-10% |
| Q 252 | Q 252 R | <2% |
| Q 252 | Q 252 E | <2% |
| Q 252 | Q 252 H | > 10% |
| Y 253 | Y 253 F | 2-10% |
| Y 253 | Y 253 H | 2-10% |
| E 255 | E 255 V | 2-10% |
| E 255 | E 255 K | > 10% |
| D 276 | D 276 G | <2% |
| V 289 | V 289 I | <2% |
| V 304 | V 304 G | <2% |
| F 311 | F 311 I | <2% |
| F 311 | F 311 L | <2% |
| T 315 | T 315 N | <2% |
| T 315 | T 315 I | > 10% |
| F 317 | F 317 L | 2-10% |
| G 321 | G 321 E | <2% |
| M 343 | M 343 T | <2% |
| M 351 | M 351 T | > 10% |
| E 352 | E 352 G | <2% |
| Y 353 | Y 353 H | <2% |
| E 355 | E 355 D | <2% |
| E 355 | E 355 G | 2-10% |
| F 359 | F 359 A | <2% |
| F 359 | F 359 C | <2% |
| F 359 | F 359 V | 2-10% |
| V 371 | V 371 A | <2% |
| E 373 | E 373 G | <2% |
| V 379 | V 379 I | <2% |
| F 382 | F 382 L | <2% |
| L 387 | L 387 M | <2% |
| T 389 | T 389 A | <2% |
| H 396 | H 396 P | <2% |
| H 396 | H 396 R | 2-10% |
| S 417 | S 417 Y | <2% |
| E 459 | E 459 K | <2% |
| F 486 | F 486 S | <2% |

FIGURE 11

MVDPVGFAEAWKAQFPDSEPPRMELRSVGDIEQELERCKASIRRLEQEVNQERFRMIYLQTLLAKEKKSYDRQRWGFRRAAQAPDGA
SEPRASASRPQPAPADGADPPPAEEPEARPDGEGSPGKARPGTARRPGAAASGERDDRGPPASVAALRSNFERIRKGHGQPGADAEKPF
YVNVEFHHERGLVKVNDKEVSDRISSLGSQAMQMERKKSQHGAGSSVGDASRPPYRGRSSESSCGVDGDYEDAELNPRFLKDNLIDA
NGGSRPPWPPLEYQPYQSIYVGGMMEGEGKGPLLRSQSTSEQEKRLTWPRRSYSPRSFEDCGGGYTPDCSSNENLTSSEEDFSSGQSSR
VSPSPTTYRMFRDKSRSPSQNSQQSFDSSSPPTPQCHKRHRHCPVVSEATIVGVRKTGQIWPNDGEGAFHGDADGSFGTPPGYGCAA
DRAEEQRRHQDGLPYIDDSPSSSPHLSSKGRGSRDALVSGALESTKASELDLEKGLEMRKWVLSGILASEETYLSHLQMLTNSCVKLQT
VHSIPLTINKEEALQRPVASDFEPQGLSEAARWNSKENLLAGPSENDPNLFVALYDFVASGDNTLSITKGEKLRVLGYNHNGEWCEAQ
TKNGQGWVPSNYITPVNSLEKHSWYHGPVSRNAAEYLLSSGINGSFLVRESESSPGQRSISLRYEGRVYHYRINTASDGKLYVSSESRF
NTLAELVHHHSTVADGLITTLHYPAPKRNKPTVYGVSPNYDKWEMERTDITMKHKLGGQYEGVYEGVWKKYSLTVAVKTLKEDT
MEVEEFLKEAAVMKEIKHPNLVQLLGVCTREPPFYIITEFMTYGNLLDYLRECNRQEVNAVVLLYMATQISSAMEYLEKKNFIHRDLA
ARNCLVGENHLVKVADFGLSRLMTGDTYTAHAGAKFPIKWTAPESLAYNKFSIKSDVWAFGVLLWEIATYGMSPYPGIDLSQVYELL
EKDYRMERPEGCPEKVYELMRACWQWNPSDRPSFAEIHQAFETMFQESSISDEVEKELGKQGVRGAVSTLLQAPELPTKTRTSRRAAE
HRDTTDVPEMPHSKGQGESDPLDHEPAVSPLLPRKERGPPEGGLNEDERLLPKDKKTNLFSALIKKKKTAPTPPKRSSSSFREMDGQPE
RRGAGEEEGRDISNGALAFTPLDTADPAKSPKPSNGAGVPNGALRESGGGSGFRSPHLWKKSSTLTSSRLATGEEEGGSSSKRFLRSCS
ASCVPHGAKDTEWRSVTLPRDLQSTGRQFDSSTFGGHKSEKPALPRKRAGENRSDQVTRGTVTPPPRLVKKNEEAADEVFKDIMESSP
GSSPPNLTPKPLRRQVTVAPASGLPHKEEAGKGSALGTPAAAEPVTPTSKAGSGAPGGTSKGPAEESRVRRHKHSSESPGRDKGKLSRL
KPAPPPPAASAGKAGGKPSQSPSQEAAGEAVLGAKTKATSLVDAVNSDAAKPSQPGEGLKKPVLPATPKPQSAKPSGTPISPAPVPST
LPSASSALAGDQPSTAFIPLISTRVSLRKTRQPPERIASGAITKGVVLDSTEALCLAISRNSEQMASHSAVLEAGKNLYTFCVSYVDSIQQ
MRNKFAFREAINKLENNLRELQICPATAGSGPAATQDFSKLLSSVKEISDIVQR (SEQ ID NO: 11)

FIGURE 12

MVDPVGFAEAWKAQFPDSEPPRMELRSVGDIEQELERCKASIRRLEQEVNQERFRMIYLQTLLAKEKKSYDRQRWGFRRAAQAPDGA
SEPRASASRPQPAPADGADPPPAEEPEARPDGEGSPGKARPGTARRPGAAASGERDDRGPPASVAALRSNFERIRKGHGQPGADAEKPF
YVNVEFHHERGLVKVNDKEVSDRISSLGSQAMQMERKKSQHGAGSSVGDASRPPYRGRSSESSCGVDGDYEDAELNPRFLKDNLIDA
NGGSRPPWPPLEYQPYQSIYVGGMMEGEGKGPLLRSQSTSEQEKRLTWPRRSYSPRSFEDCGGGYTPDCSSNENLTSSEEDFSSGQSSR
VSPSPTTYRMFRDKSRSPSQNSQQSFDSSSPPTPQCHKRHRHCPVVSEATIVGVRKTGQIWPNDGEGAFHGDADGSFGTPPGYGCAA
DRAEEQRRHQDGLPYIDDSPSSSPHLSSKGRGSRDALVSGALESTKASELDLEKGLEMRKWVLSGILASEETYLSHLQMLTNSCVKLQT
VHSIPLTINKEEALQRPVASDFEPQGLSEAARWNSKENLLAGPSENDPNLFVALYDFVASGDNTLSITKGEKLRVLGYNHNGEWCEAQ
TKNGQGWVPSNYITPVNSLEKHSWYHGPVSRNAAEYLLSSGINGSFLVRESESSPGQRSISLRYEGRVYHYRINTASDGKLYVSSESRF
NTLAELVHHHSTVADGLITTLHYPAPKRNKPTVYGVSPNYDKWEMERTDITMKHKLGGQYEGVWKKYSLTVAVKTLKEDT
MEVEEFLKEAAVMKEIKHPNLVQLLGVCTREPPFYIITEFMTYGNLLDYLRECNRQEVNAVVLLYMATQISSAMEYLEKKNFIHRDLA
ARNCLVGENHLVKVADFGLSRLMTGDTYTAHAGAKFPIKWTAPESLAYNKFSIKSDVWAFGVLLWEIATYGMSPYPGIDLSQVYELL
EKDYRMERPEGCPEKVYELMRAYFDNREERTR (SEQ ID NO: 20)

FIGURE 13

5'-GTAAGCCTTCCTCAGCCTGTTCTCACGAGTATATGTGGGCATTCCAGGAAATT
CAACTGTGCAGGAGTGTGTACACAAAGTTGAAAGTTTTCCATGAGCTCTCCATTCCAGTTCTTCAGATGCAGTAATGTAGCC
ATTTGCTACCTATTGACCTTTATTTACAGATAAATAGTATGTGCGTGACTTGTCTTTAAAGCAAAAATGGTATTGATAGATACCA
AACCTGGGTGTATTCCTAAATACAGATTCCTGGCCCTGCTTTCACAGACATTCTGCTATAGTAGCTAAGCTCATGAGGTGATTTT
TTTTTTTTTTTTGAGACGGAGTTTCGCTCTGTGCCCAGGCTGGAGTACAAGTGGCAATGTGGCTCACTTCAACCTCCAC
CTCCCTGGTCTTCAAGCGATTCTCCTGCCTCAGCCTCCCAAGTAGCTGGGATTACAGGCATGCACCACCACGCCCGGCTAATTTTGTA
TTTTTAGTAGAGATGGGGTTTCTCCATGTTAGTCAGGCTGGTCTCGAACCTCCCAACCTCAAGGTGATCTGCCTGCCTCGGCCTCCCA
AAGTGCTGCGATTACAGGCGTGAGCCACCACGCCCAGCTGCGAGGTGATTTTATCTGGTCGTTTCTTATACTGATTACATATGTGTT
ATCTGTACTATGCACACACAGGATGTTTCATATCTTATAAGGTATTTATATGGCCATTTCTTACACTGTTTCCCACACATGTC
TTTCCACGTCCATATATTCAGATCTCCATTCCCAGTACTCCATTCACTCATTCATCC
GGTCCTCTTTGATGTGCATTTGGTCATTTGGTTTTGGTTTTTGCCCTTATAAACAAGCAGAAACAAATATTCATGTAC
ACGAATCTCTGGGCACTTGCTGGTATTTCTAAAAGTTGAACTGTGGTTCCAAGAACTGTGTGGTTCCTGGTCCCCAGTACTAG
TTACCAAACTGTTAAAAAGGTTGTGCCATTGATGTCTCCAGTCAGACGCATATGGGAGTGACTGTTCCTGGTCCCCAGTACTAG
GCTTTGTCAGTCTGTTAGTCTGCATGTTAGTCCTCATGTTAGTCATTTTCAGTCATTTTCACTTCAG<u>ACTTTGATAACCGTGAAGAAAGA
ACAAGATAGAAG</u>GTGAGCTGTTGGCTTAGTAATTTCTACACCTACTAGAGGGACTGGGAAATATATTTGTAAATGCAG
TTCTTGCTGTCACTGTCTCTGGGTTTACAATCCATATTCCTGCCAGCATCTAACGTCTTTTCAAATTCTTAATGTCTATAACA
GGACATGATGACATTCATCGTTTGACTTGTTGCAGCAAAAGATGGTTAGCAGGATTGGAATGTTGCTTTCATTCTAGACTTTTCC
TTGAGAACTGCTAGCCCCGTATTGCTAGCCAGATCTCATGATGATCGACTTGGGTTTCATCTGTCCAG-3'

(SEQ ID NO: 3)

FIGURE 14

MLEICLKLVGCKSKKGLSSSSSCYLEEALQRPVASDFEPQGLSEAARWNSKENLLAGPSENDPNLFVALYDFVASGDNTLSITKGEKLR
VLGYNHNGEWCEAQTKNGQGWVPSNYITPVNSLEKHSWYHGPVSRNAAEYPLSSGINGSFLVRESESSPSQRSISLRYEGRVYHYRIN
TASDGKLYVSSESRFNTLAELVHHHSTVADGLITTLHYPAPKRNKPTVYGVSPNYDKWEMERTDITMKHKLGGGQYEGVYEGVWKK
YSLTVAVKTLKEDTMEVEEFLKEAAVMKEIKHPNLVQLLGVCTREPPFYIITEFMTYGNLLDYLRECNRQEVNAVVLLYMATQISSAM
EYLEKKNFIHRDLAARNCLVGENHLVKVADFGLSRLMTGDTYTAHAGAKFPIKWTAPESLAYNKFSIKSDVWAFGVLLWEIATYGMS
PYPGIDRSQVYELLEKDYRMKRPEGCPEKVYELMRACWQWNPSDRPSFAEIHQAFETMFQESSISDEVEKELGKQGVRGAVTTLLQAP
ELPTKTRTSRRAAEHRDTTDVPEMPHSKGQGESDPLDHEPAVSPLLPRKERGPPEGGLNEDERLLPKDKKTNLFSALIKKKKTAPTPP
KRSSSFREMDGQPERRGAGEEEGRDISNGALAFTPLDTADPAKSPKPSNGAGVPNGALRESGGSGFRSPHLWKKSSTLTSSRLATGEEE
GGGSSSKRFLRSCSVSCVPHGAKDTEWRSVTLPRDLQSTGRQFDSSTFGGHKSEKPALPRKRAGENRSDQVTRGTVTPPPRLVKKNEE
AADEVFKDIMESSPGSSPPNLTPKPLRRQVTVAPASGLPHKEEAWKGSALGTPAAAEPVTPTSKAGSGAPRGTSKGPAEESRVRRHKHS
SESPGRDKGKLSKLKPAPPPPAASAGKAGGKPSQRPGQEAAGEAVLGAKTKATSLVDAVNSDAAKPSQPAEGLKKPVLPATPKPHPA
KPSGTPISPAPVPLSTLPSASSALAGDQPSSTAFIPLISTRVSLRKTRQPPERASGAITKGVVLDSTEALCLAISGNSEQMASHSAVLEAGK
NLYTFCVSYVDSIQQMRNKFAFREAINKLENNLRELQICPASAGSGPAATQDFSKLLSSVKEISDIVQR (SEQ ID NO: 24)

FIGURE 15

MLEICLKLVGCKSKKGLSSSSSCYLEEALQRPVASDFEPQGLSEAARWNSKENLLAGPSENDPNLFVALYDFVASGDNTLSITKGEKLR
VLGYNHNGEWCEAQTKNGQGWVPSNYITPVNSLEKHSWYHGPVSRNAAEYPLSSGINGSFLVRESESSPSQRSISLRYEGRVYHYRIN
TASDGKLYVSSESRFNTLAELVHHHSTVADGLITTLHYPAPKRNKPTVYGVSPNYDKWEMERTDITMKHKLGGGQYEGVYEGVWKK
YSLTVAVKTLKEDTMEVEEFLKEAAVMKEIKHPNLVQLLGVCTREPPFYIITEFMTYGNLLDYLRECNRQEVNAVVLLYMATQISSAM
EYLEKKNFIHRDLAARNCLVGENHLVKVADFGLSRLMTGDTYTAHAGAKFPIKWTAPESLAYNKFSIKSDVWAFGVLLWEIATYGMS
PYPGIDRSQVYELLEKDYRMKRPEGCPEKVYELMRAYFDNREERTR (SEQ ID NO: 25)

FIGURE 16A

5'-ATGGTGGACCCGGTGGGCTTCGGCGAGGCGTGGAAGGCGCAGTTCCCGGACTCAGAGAGCCCCCGCCATGGAGCTGCGCTCAG
TGGGCGACATCGAGCAGGAGCTGGAGCGCCTCCATTCGGCGCTGGAAGCGCTGGAAGCAGGAGGTGAACCAGGAGCGCTTCCGCA
TGATCTACCTGCAGACGTTGCTGGCCAAGGAAAAGAAAGAGCTATGACCGGCAGCAGTCCCGGCAGCCGCTTCCGCGCGCCGGCCC
CCGACGGCGGCCTCCGAGCCCTCGAGCCCGACGGCGGGGAGGGGTTCTCCGGGTAAGGCGCAGGCCCCAGGCCGCGCCCGCCGAGG
AGCCCGAGCCCGAGCCCGACGGGGACGGGGACCCCCGCAGCGTGGCGCTCAGGTCCAACTTCGAGCGGATCCGAGCCCAGGCCGTCG
GGGAACGGGACGGGCGGGACGCCCGAGAAGCGCTCCTGGGCACTTGCACGAGCCAGCGCCCTGGTGAAGGTCAACGACAAAGA
GCCCGGGGGCGGGACGCGCATCAGCTCCGGGGACGTCCCTGGGCAGCCATGGAGCAGATGGAGCGCAAAAGTCCAGCGCGGGCGTGAGCGT
GGTGTCGAGACCGCATCCAGCGCCCCCTTACGAGGACAACCTGATCGACGCCAGGCGGTAGCAGGCCCCCTTGGCGCCGACTACGAGCGCCAGCCTA
GAACCCCGCTTCCTGAAGGACAACCTGATGATGGAAGGCGAAGGCCCGAGTTTGAGGATTGCGAGGGCTATACCCTGAGCAGTCCAA
CCAGAGCCTTACCTGGCCCGCAGTCTCTACTCCCCCGGAGTTTGAGGATTGCGAGGGCTATACCCTGAGCAGTCCAA
AGCGCCTTACCTGGCCCGCAGTCTCTACTCCCCCGGAGTTTGCGCAGAGCCCAGAGCCAGAGCCACCACTACCGCATGTTC
TGAGAACCTCACCTCAGCGGAGGAGACTTCCTCTGGCCAGTCCTTGGCACAGAACTCCTTGACACAGTCCTTGCGCCATAAGCGG
CGGGACAAAAGCCGTCTCCGCAACTGCCGAGAACTCGTGGGCGTCCGGGCAGATCTGCCCAACGATGGCGAG
CACCGGCACTGCCGCCGTTGTCGAGACGCAGATGGCTCGTTCGGAACACCACCTGGATACGGCTGCGCTGCAGACGGGGCAGAGAGCAGCGC
GGCGCCTTCCATGGAGACGCAGATGGCTGCCCTACACATTGACTCGCCCCTCATCGCCCACCTCAGCAGCAGCAAGGCAAGGGCAGCGGGAT
CGCGCACCAAGATGGCTCGCGGAGCCCTGGAGTCCACTAAAGCGAGTGAGTGGAACTTGGAAAAGGGCTTGCAGCCAGGGTCGGGTCTG
GCGCTGGTCTCGGGAGCCCCCTGGAGCTTACCTGGAGGAGACTTACCTGAGCAGTGCTGCGCCATGAAGCCTTTGAAAGCCGCTGCC
TCGGGAATCCTGGCTAGCGGAGGAGACTTACCTGAGCAGTGCTGAGGCCACTGCTCTTCAAAGTGCCTGAGTCTACGAGATCCACAAGGAGT
ACCACCTCTCAGCCGGTGCTGAGAGTCGACAGATGCAGCGAGTCGAGACCATCTTCAAAGTGCCTGAGTCTACGAGATCCACAAGGAGT
TCTATGATGGCTCCCCGCGTGCTGAGAGTGGAGCCACCAGCAGTGGGAGCACCTCTTCCAGAAGCTGGCCAGCCAGCT
GGGTGTGTACCGGTCTTAGCGTAATCACATGGTGTGAAGCGCACGAATGCCAGGCTGCAATGTCCCGCAATGCCGCTGAGTATCTGTG
CAACTACATCAACAGTCTTGGTAGAGCAGTTGGTGGCTGAGAGTGAGAGCAGTCCTGCCAGAGGTGCATCGTCGTGAGATACGAAGGG
AGCAGCGGGATCAATGCAGTCTTCTGGTGCCTGAGAGTGAGAGCAGTCCTAGCTCCAGAGGTGCATCGTCGTGAGATACGAAGGG
AGGGTGTACCATTACAGATCAACAGGTCTTCTGATGCAAGCTGTCTCGAGAGCCGCTTCAACACCCTGGCCGAGT
TGGTTCATCATCATTCAAGCGGTGCCGACGGCTCATCACCACGCTCCATTATCCAGCCAAGCCAACAAGCCACTGTCTA
TGGTGTGTCCCCAACTACGACAAGTGGGAGATGGAAGCACGAGATCACCATGAAGACAAGCTGGGCGGGCCAGTACG
GGGAGGTGTACGAGGCCGGTGTGAAGAAATACAGCCCGTGCCGTTGAAGACCTTGAAGGAGGACACCATGGAGGTGAA
GAGTTCTTGAAAGAAGCTGCAGTCATGAAAGAGATCAAACACCCTAACCTGGTGCAGTCCTTGGGGTCTGCACCCGGGAGCCC
CGTTCTATATCATCATCACTGAGTTCATGACCTACTGGAACCTCGACTACCTGAGGGAGTGCAACCGGCAGGAGG

FIGURE 16B

TGAACGCCGTGGTGCTGCTGTACATGGCCACTCGAGATCTCGTCAGCCATGAGTACCTGAGAGAAGAAAACTTCATCCACAGAG
ATCTTGCTGCCCGAAACTGCCTGGTAGGGAGAACCACTTGGTGAAGTAGCTGATTTGGCTGAGCAGGTTGATGACAGGG
ACACCTACACAGCCCATGCTGAGAGCCAAGTTCCCCATCAAATGACTGCCACCCGAGAGCCTGGCTACACAAGTTCTCCATCAA
GTCCGAGCTCTGGGCATTGCTTGGAGAGTATTGCTTGGGAAATTGCTACCTATGCATGTCCCCTTACCGGGAATTGACCTGTCCAGA
TGTATGAGCTGCTAGAAGGACTACCGCATGGAGGACCATGAAGGCTGCCCCAGAGAAGGTCTATGAACTCATGGAGCATGTT
GGCAGTGGAATCCCTCTGACCGCCTCCTTTGCTGAAATCCACCAAGCTTTGAAACAATGTTCCAGAATCCAGTATCTCAGA
CGAAGTGGAAAAGGAGCTGGGGAAACAAGGCGTCCGTGAGTACCTTGTCAGCCCCAGAGCTGCCAGCCCTCAAGGCCAAGA
CGAGGACCTTCCAGGACCATGAGCTGCAGAGCACCACCACTGACCTGCTCCCTCGAAAAGAGCGAGGTCACTCACTCCAAGGGCGGCTGAATGAAGAT
GATCCTCTGACCCTCTCCCAAAGACAAAAGACCAACTTGTTCAGCCGCTTGATCAAGAGGGGCCAGCAGCCAGTCCCCAAAGCTGATCGAGACATCAGCAA
GAGCCTTCTCCCAAAGACAAAAGACCAACTTGTTCAGCCGCTTGATCAAGAGGGGCCAGCAGCCAGTCCCCAAAGCCCCCTCCC
AAACGCAGCAGCTCCTTCACCCCCTTGACCAGCAGTCCAGCCAGTCGACCCAGCCAAGTCCCCCACACTGTGAAAGAAGTCCAGCACGCTGACCAGCAGCCTAGC
CGGGCACTGGCTCGGGAGTCCGGAGTGGCCGGTGCAGTCGCCTCCTCCAGCGCTTCCGCCTCTGCGTTCCCCATGGGCCAAG
CACCGGACGAGGAGGAGGAGCCGGCTCAGTGCAGCCTCTGCCTCGGAAGACAGTTGCAGTCGACCAGTCTGAAAGACATCATGGAGTCCAGCCTCGTCACATTTGACTCGTCACAGTGGAGGGCAC
AAAGTGAGAAGCCGGCTCTGCCTGCCAGTCAGTGAGGTCTTCAAAGACCGTGAGCCCTGCCTCGGCCTCCACGTGACCCCCACAAGGAAGAAGCTGGAAAGGG
CCCCAGGCTGGTGAAAAAAACCCCCTGAACCTGACTCAGAATGAGGAAGCGGCAGGTCGTCAAAGACCGTGAGCCCTGCCTCGGCCTCCACGTGACCCCCACAAGGAAGAAGCTGGAAAGGG
CAACCTGACTCAGTCCAAAAACCCTCAGGGACCCCAGGTCGCAGCTGCAGTGCAGCCAGGTCACCGTGACCCCCACAAGGAAGAAGCTGGAAAGGG
CAGTGCCTTAGGGACCCGAGAGTCCAGAGTGAGGAGCAGCCAGGCTGAGGAGGACACAAGCACTCCTGAGTCGCCAGGAAAGCAAGGAAGCGGAAATTGTCAGGC
GGGCCCCGCCAGGAGTGAGCCAGCAGCCAGCTCTGCAGGAAGGCTGGAGGAAAGCCCTGCAGAGCCGCAGCCAGGAGGCG
TCAAACCTGCCCCGCCCACCAGCAGCCAGCTCTGCAGGAAGGCTGGAGGAAAGCCCTGCAGAGCCGCCAGCCAGGAGGCG
GCCGGGGAGGCAGTCCTGGGCGCAAAGCCACGAGTTCGTTGATGCTGTGAACAGTGACGCTCCGCCAAGCCCCAGCCA
GCCGGGAGAGGGCCTCAAAAAGCCCGTGTCCAAAGCCACACTCCGGGACCCAAGCCGTCGGGGACCCCATCAGCCC
AGCCCCCCGTTCCCTCCACGTTGCCATCAGCATCTCCGGCCATCGGGCCGTCTTCCACCGCCTTCCATCCCTCTCATAT
CAACCGAGTGTCTTCGGAAAACCGGCATCTTGGAATCCGCAGAGCGGATCGCCAAGCCTCCAGAGCGGATCGCCATCACCAGGGCGTGGTCCTGGACA
GCACCGAGGCCGTGTGCCGAGCTTCAGATCTGCCCCGGACATCAGCAGACAAAATGAGGAACAGCAAGTTTGCCTTCCGAGAGGCCATCAACAACTGGA
TCTACACGTTCTGCGTGAGCTTCAGATCTGCCCGGACATCAGCAGACAAAATGAGGAACAGCAAGTTTGCCTTCCGAGAGGCCATCAACAACTGGA
GAATAATCTCGGAGGAAATCAGTGACATAGTGACAGAGGTAG-3'

(SEQ ID NO: 19)

FIGURE 17A

ATGGTGGACCCGGTGGCTTCGCGAGGCGTGGAAGGCCAGTTCCCGGACTCAGAGCCCGCGCATGGAGCTGCGCTCAGTG
GGCGACATCGAGCAGGAGCTGGAGCGCCTGCAAGGCCTCCATTCGGCGCCTGGAGCCAGGAGGTGAACCAGGAGCGTTCCGCATG
ATCTACCTGCAGACGTTGCTGCAAGGCCAAAGAGAGCTATGACCGGCAGCGGCTTCCGGCGCGGCGCAGCCCCC
GACGGGCGCCTCCAGCCCGAGCCCGGACGGCCAGCGCCCGGAGCGCGACCCGCCGAGCCCGCCCGCGAGGAG
CCCGAGGCCCGACGACCGGGACACCGGGAGGGTCTCCGGCAGCGGGTAAGGCCAGGACCCGGAGCGCAGCGGCGTCGGG
GGAACGGGACGACCGGGAGCGCGAGAAGCCCTTCAGGTCCAACTTCGAGCGGATCCGAAGGGCCATGGCCAGC
CCGGGGGACGCGCATCAGCTCCTGGGCAGCCAGCGTCTACGAGCAGCCATGCGAGTTCAACGTGAAGGTCAACGACAAAGAGG
TGTCGGACCGCATCAGCTCCTGGGCAGCCAGCGTCTACGAGCAGCCATGCGAGTGGCGCAAAAGTCCAGCGAGCGCTCGAGCGTGG
GGGATGCATCCAGGCCCCTTACCGGGAGCGCTCATGACGCAATGGCGGTAGCAGGCCCTGAGTGAGTCGACCGCGAGTTGA
ACCCCGCTTCCTGAAGGACAACCTGATCGACGCAATGGCGGTAGCAGGCCCCTGAGTACCAGCCTACCA
GAGCATCTACGTCGGGGGACGCCAGGTCTCCTACTCCCCCCGAGTTTTGAGGATTGCCGCAGGCCAAGGGCAAGGGCACCTCTGAGCAGGAGAAGC
GCCTTACCTGCCCCGCAGGCAGGACTCTCTGGCCAGTCCAGTCCCCCCAGAGAAGGGCAGTTTTGAGGATTGCCGCAGGCCAAGGGCAAGGGCACCTGACTCAGTCATGTTCGG
GAACCTCACCTCCAGGAGGACTTCTCTGGCCAGTCCAGTCCTTCGACACAGCAGCCCTCGCAACAGTCCTTCGACACAGCAGCCCTCGCAACAGTCCTTCGACACAGCAGCCCTCGCAACAGTCCTTCGACACAGCAGCCGCCATAAGCGGCAC
GGCACTGCCCGGTTGTCGTGGCCCGGTTGTCGTGGAGGCCACCATCGTGGGGTCCGAGGCAGATCTGGCCAACGATGGCGAGGGC
GCCTTCCATGGAGACGCAGATGGCTCGTTGCGAACCACCTCGGAACCACCTCCTCATCGCCCCACCTCAGCAGCAAGGGCCAGCAGCGCCGG
CACCAAGATGGGCTGCCCTACATTGATGACTCGCCCTACATTGATGACTCGCCCTACATTGATGACTCGCCCTACATTGATGACTCGCCCTACATTGATGACTCAAGGGCTTGGAGATGAGAAATGGGCTCTGTCG
CTGGTTCTCGGGAGCCCTGGAGCCCTGAGTCACTAAAGCGAGTCACTAAAGCGAGTGGACTGGAGCTGGACTGGAGCTGGAGCTGGACTGGAGATGAGAAATGGGCTCTGTCG
GGAATCCTGGCTAGCGAGGAGACTTACCTGAGGCCACCTGAGGCCACTCTTCAAAGTGCTGCTGCCCATGAAGCCTCTACGAGATCCACAAGGAGTTCT
ACCTCTCAGCCGGTCTCTTCCCCGGGTGCAGCAGTCAGCAGTGAGCCACCAGCAGGGTGGGAGCCACTGGAGCCACTGGAGATGAAAAATGGGATGTTGAAAGCCGCTGCACC
ATGATGGGCTCTTCCCCGGGGTGCAGCAGTGAGCCACCAGCAGGGTGGGAGCCACTGGAGCTGGGAAGCTGGGAAGCTCTACGAGATCCACAAGGAGTCT
GTGTGTACCGGGTCTTAGCTATAATCACAAGCGTGAAGCCCAAACCAAAAATGCCAAGCTGGGTCCAAGCA
ACTACATCACGCCAGTCAACAGTCTGGAGAAACACTCCTGGTACCATGGGCCTGTCCCGCAATGCCGCTGAGTATCTGCTGAG
CAGCGGGATCAATGGCAGCTTCTTGGTGCGT

FIGURE 17B

GAGAGTGAGAGCAGTCCTGGCCAGAGGTCCATCTCGCTGAGATACGAAGGGAGGGTGTACCATTACAGGATCAACACTGCTTCT
GATGGCAAGCTCTACGTTCGTCTCCTCCGAGACGTTCAACACCCTGGCCGAGTTGGTTCATCATCATTCAAGGGTGGCCGACGGC
TCATCACCACGCTCCATTATCCAGCCCCAAAGCGCAACAAGTGTCTATGGTGTGTCCCCAACTACGACAAGTGGGAGAT
GGAACGCACGGACATCACCATGAAGCACAAGTGGGCGGGGCCAGTACGGGAGGTGTACGAGGGCGTGTGAAGAAATACA
GCCTGACGGTGCCGTGAACCTGTGCAGCTCCTTGGGTTCTGCACCCGGGAGCCCCCCGTTGAAAGAAGCTGCAGTCATGAAAGAG
ATCAAACACCCTAACCTGGTGCAGCTCCTTGGGTTCTGCACCCGGGAGCCCCCCGTTCTATATCATCACTGAGTTCATGACCTACG
GAACCTCCTGGACTACCTGAAGGAGAAGAAAACTTCATCACAGAGATCTTGCCCGAAACTGCTGTACATGGCCACTCAGATCTCGT
CAGCCATGGAGTACCTGGAGAGAAGAAAACTTCATCACAGAGATCTTGCCCGAAACTGCTGTAGGGGAGAACCACTGG
TGAAGGTAGCTGATTTTGGCCTGAACAGGTTGATGACAGGTGATGACCTGTCCCAGTGTATGAGCGTATGAGGACGCATGGAGCGCCCA
GGACTGCACCCGAGAGCCTGGCCTACAACAGTTCTCATCAAGTCACCTATTTGGAGTATTGCTTTGGGAAATTGC
TACCTATGGCATGTCCCCTTACCCGGGAATTGAACCTGTCCCAGTGTATGAGCGTATGAGGACGCATGGAGCGCCCA
GAAGGCTGCCCAGAGAAGTCTATGAACTCATGCGAGCATACTTTGATAACCGTGAAGAACAAGAACAAGATAGAAGGTTGGCA
GTGGAATCCCTCTGACCGGCCGCTCCTTTGCTGAAATCCACCAAGCTTTGAAACAATGTTCCAGTATCTCAGACGAA
GTGGAAAAGGAGCTGGGGAAACAAGGCGTCCGTGAGTACCTTGCTGAGTACTTGTGCAGGCCCAGCTGCCCACCAAGAGACGAG
GACTCCAGGAGGAGAGTGCAGAGACACAGAGCACACCACTGACGTGCCTGAGATGCCTCACTCAAGGGCCAGGAGAGAGCGATC
CTCTGACCAATGAGCCTGCGTGTCCCATTGCTCCCTGAAAAGAGGAGGTCCCCGAGGGCGGCCTGAATGAAGATGAGC
GCCTTCTCCCAAAGACAAAAGACCAAACTTGTTCAGCGCCTTGATCAAGAAGAAGACACAGCCCAACCCCTCCAAAC
GCAGCAGTCCTTCCGGAGATGGACGGCCAGCCGGAGCCAGGAGAGGGCCAGAGAGGGCCGAGACATCAGCAACGGG
GCACTGGCTTTCACCCCTTGACACAGTCGACCAGCCAGCTGACCAGCCAGCCAATGGGGTCCCAATGGAGCC
CTCCGGGAGTCCGGAGTCCAGGCTCAGCTGCAGCTGCCAGCTGCCACCCGGTCTCCCACGCTGACGCTGAGCCAGCCACC
GGCGAGGAGAGGGCGGTGCAGTCACGCTGCCTCGGAAGCGTCTTGCTGCTTCCCAGCAAGCGTTCCTCGGTTCCCATGGGCCAAGGAC
ACGGAGGAGTGGAGGTCAGTCACGCTGCCTCGGAAGAGGGCAGGGGAGACAGTTGACTCGTCCACATTTGGAGGGCACAAA
AGTGAGAAGAAGCCGGTCTCTGCCTCGGAAATGAGGAAGCTGCTAGGTCTTCAAAGACATCATGGAGTCGAAAGACATCAGTAACGCCTCCCC
CAGGCTGGTGAAAAACCCCTCACCGTGGCCCTCACCGTGCCCCTGCCTCGCCAGCCTGGAGTCCAGCCGCCCAGCCCGCCCAA
CCTGACTCCAAAACCCCTCACCGTGGCCCTCACCGTGCCCCTGCCTCGCCAGCCAGCCTGGAGTCCAGCCGCCCAGCCCGCCCAA

FIGURE 17C

GAAGAAGCTGGAAAGGGCAGTGCCTTAGGGACCCCTGCTGCAGCTGAGCCAGTGACCCCACCAGCAAAGCAGGCTCAGGTGC
ACCAGGGGCACCAGCAGCAAGGGCCCGCCAGGAGTCCAGGAGTGAGGAGGCACAAGCACTCCTCTGAGTCGCCAGGAGGACA
AGGGGAAATTGTCCAGGCTCAAACCTGCCCGCCCCCGCCAGCAGCCTGCAGGGAGGCAGCCTGCAGGGAAGCCCTGCAGA
GCCCGAGCCAGGAGGCGGGAGGCAGTCCTGGGCGCAAAGACAAAGCCACGAGTCTGGTTGATGCTGTGAACAGTGAC
GCTGCCAAGCCAGCCAGCCCGTGCTCCCGGCCTCAAAAGCCCGGCCACTCCAAAGCCACAGTCCGCCAAGCCGTCG
GGGACCCCCATCAGCCAGCCCAGCCCCGCCCCCGTTCCCTCCACGTTGCCATCAGCATCCTCGGCCAGGGACCAGCCGTCTTCCACCG
CCTTCATCCCTCTCATATCAACCCGGAGTGTCTTCGGAAAACCCGCCAGCCTCTAGGAACTCCGAGCAGATGCCAGCCACAGCGCAGTGCT
GGGCGTGGTCCTGGACAGCACCGAGGCGTGTCCTGCCGCTATGTGGATTCCATCCAGCAACAAGTTTGCCTTCCGAGA
GGAGGCCGGCAAAAACCTCTACACGTTCTGCGTGAGCTATGTGGATTCCATCCAGCAACAAGTTTGCCTTCCGAGA
GGCCATCAACAAACTGGAGAATAATCTCCGGAGCTTCAGATCTGCCCGGACAGCAGGCAGTGGTCCGGCGGCCACTCAGGA
CTTCAGCAAGCTCCTCAGTTCGGTGAAGGAAATCAGTGACATAGTGCAGAGGTAG (SEQ ID NO: 26)

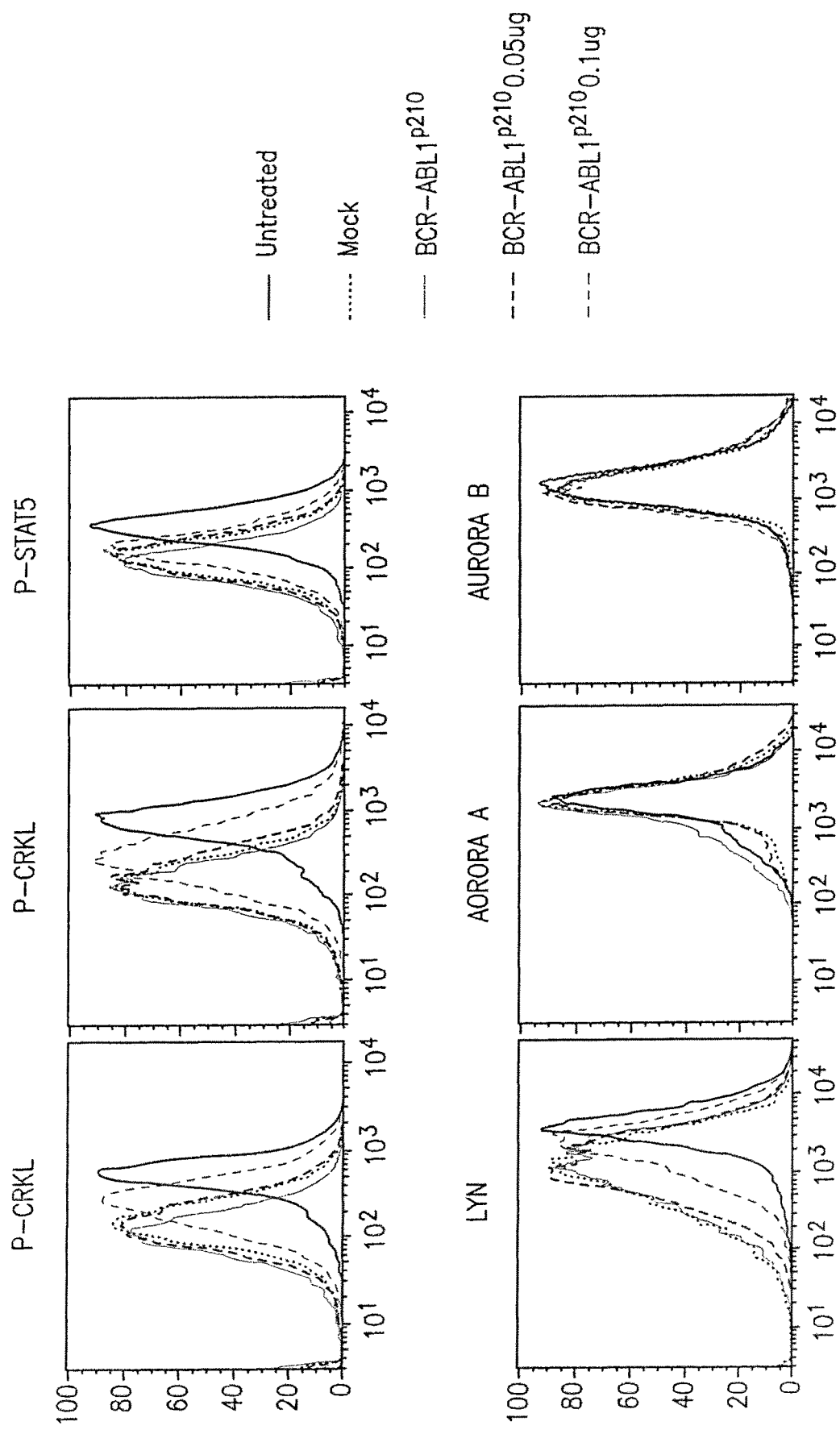

BCR-ABL VARIANTS

CROSS-REFERENCE TO RELATED APPLICATIONS

This application is a Continuation of U.S. application Ser. No. 16/989,125, filed Aug. 10, 2020, which is a Continuation of U.S. application Ser. No. 15/643,937, filed Jul. 7, 2017, which is a Continuation of U.S. application Ser. No. 12/472,319, filed May 26, 2009, which claims benefit of U.S. Provisional Application No. 61/110,512, filed Oct. 31, 2008, hereby incorporated by reference.

The instant application contains a Sequence Listing which has been submitted in ASCII format via EFS-WEB and is hereby incorporated by reference in its entirety. Said ASCII copy, created on Mar. 14, 2022, is named sequence.txt and is 62,994 bytes.

FIELD OF THE INVENTION

The present inventions relate to BCR-ABL variants and resistance to kinase inhibitor therapy.

BACKGROUND OF THE INVENTION

The following description is provided to assist the understanding of the reader. None of the information provided or references cited is admitted to be prior art to the present invention.

Chronic Myelogenous Leukemia ("CML") is a cancer of bone marrow and blood cells. In CML, healthy bone marrow cells are replaced with leukemic cells; myeloid, erythroid, megakaroyocytic and B lymphoid cells are among the blood cells which become leukemic due to the effects of a characteristic chromosomal translocation.

CML is associated with a specific chromosomal abnormality called Philadelphia chromosome. The genetic defect is caused by the reciprocal translocation designated t(9;22) (q34; q11), which refers to an exchange of genetic material between region q34 of chromosome 9 and region q11 of chromosome 22 (Rowley, J. D. Nature. 1973; 243: 290-3; Kurzrock et al. N. Engl. J. Med. 1988; 319: 990-998). This translocation results in a portion of the bcr ("breakpoint cluster region") gene from chromosome 22 (region q11) becoming fused with a portion of the abl gene on chromosome 9 (region q34).

The fused "bcr-abl" gene is located on chromosome 22, which is shortened as a result of the translocation. The fused gene retains the tyrosine kinase domain of the abl gene, which is constitutively active (Elefanty et al. EMBO J. 1990; 9: 1069-1078). This kinase activity activates various signal transduction pathways leading to uncontrolled cell growth and division (e.g., by promoting cell proliferation and inhibiting apoptosis). For example, BCR-ABL may cause undifferentiated blood cells to proliferate and fail to mature.

Treatment of CML may involve drug therapy (e.g., chemotherapy), bone marrow transplants, or combinations of both. One class of drugs that may be used for treating CML are kinase inhibitors. For example, "imatinib mesylate" (also known as STI571 or 2-phenylaminopyrimidine or "Imantinib" for short) has proven effective for treating CML (Deininger et al., Blood. 1997; 90: 3691-3698; Manley, P. W., Eur. J. Cancer. 2002; 38: S19-S27). Imatinib is marketed as a drug under the trade name "Gleevec" or "Glivec." Other examples of kinase inhibitor drugs for treating CML include nilotinib, dasatinib, Bosutinib (SKI-606) and Aurora kinase inhibitor VX-680.

Imatinib is an ATP competitive inhibitor of BCR-ABL kinase activity and functions by binding to the kinase domain of BCR-ABL and stabilizing the protein in its closed, inactive conformation. Monotherapy with imatinib has been shown to be effective for all stages of CML.

Resistance to imatinib remains a major problem in the management of patients with CML. Rates at which primary (failure to achieve any hematologic response) and secondary resistance (i.e., hematologic recurrence) occurs varies dependent on the stage of diseases. Primary resistance has been reported in chronic-, accelerated-, or blast-phase at rates of 3%, 9%, and 51%, respectively (Melo, J. V. & Chuah, C. Cancer Lett. 2007; 249: 121-132; Hughes, T. Blood. 2006; 108: 28-37). Secondary resistance has been reported in these patients at rates of 22%, 32%, and 41%, respectively.

The complete mechanism of imatinib resistance in CML patients is unclear and a significant number of patients resistant to imatinib have no mutation in the bcr-abl gene. However, 35-45% of patients with imatinib resistance have mutations in the kinase domain of the BCR-ABL protein (Mahon, F. X. Blood. 2000; 96: 1070-1079). Most of the reported mutations disrupt critical contact points between imatinib and the tyrosine kinase receptor or induce a transition from the inactive to the active protein configuration, preventing imatinib binding (Nagar, B. Cell. 2003; 112: 859-871; Nagar et al., Cancer Res. 2002; 62: 4236-4243; Branford S. Blood. 2002; 99: 3472-3475; Branford et al. Blood. 2003; 102: 276-283). The T315I mutation (Gorre et al. Science. 2001; 293: 876-880; Hochhaus et al. Leukemia. 2002; 16: 2190-2196) and some mutations affecting the so-called P-loop of BCR-ABL confer a greater level of resistance to imatinib (Branford et al. Blood. 2002; 99: 3472-3475; Branford et al. Blood. 2003; 102: 276-283; and Gone et al. Blood. 2002; 100: 3041-3044) and even the new tyrosine kinase inhibitors that are currently used and tested in these patients (Hughes et al. Blood. 2006; 108: 28-37; Hochhaus, et al. Blood. 2006; 108: 225a). The role of Src family kinases has received particular interest as possible mechanism for imatinib resistance (Levinson et al. PLoS Biol. 2006; 4: e144). Overexpression and activation of the Lyn has been implicated in imatinib-resistance (Donato, N. J. Blood. 2003; 101: 690-698).

Furthermore, Chu et al. (N. Engl. J. Med. 2006; 355: 10) describe an insertion/truncation mutant of BCR-ABL in a CML patient resistant to imatinib. Chu et al. report that the mutant results from a 35 base insertion of abl intron 8 into the junction between exons 8 and 9, resulting in a new C-terminus and truncation of the normal C-terminus of the Abl portion of the fusion protein. Laudadio et al. (J. Mol. Diag. 2008; 10(2): 177-180) also reports a similar splice variant in CML patients that had undergone imatinib therapy.

SUMMARY OF THE INVENTION

The present inventions are based on a BCR-ABL splice variant that results from insertion/truncation of the bcr-abl transcript and the finding that the variant provides cells with resistance to kinase domain inhibitors such as imatinib. In one embodiment, the splice variant results from a 35 bp portion of intron 8 into the junction of exons 8 and 9, (exemplified in FIG. 1). The BCR-ABL insertion/truncation mutant also may be referred to as "35 INS BCR-ABL."

The inventions described herein include polynucleotides which encode all or portions of a novel BCR-ABL insertion/truncation splice variant and recombinant cells that express all or portions of the splice variant from a cDNA construct. Recombinant cells expressing the insertion/truncation BCR-ABL protein with an active kinase domain are useful for identifying drug candidates for treating CML. Methods for predicting likelihood for responsiveness to kinase inhibitor therapy are included along with methods, compositions and reagents for detecting the splice variant.

In one aspect, the invention provides a vector including a recombinant polynucleotide, in which the recombinant polynucleotide includes at least 40 contiguous nucleotides of SEQ ID NO: 9 or its complement. In one embodiment, the vector includes a recombinant polynucleotide having a nucleotide sequence at least 95% identical to SEQ ID NO: 1. In other embodiments, the vector includes a recombinant polynucleotide having the nucleotide sequence of SEQ ID NO: 1.

In some embodiments, the recombinant polynucleotide is operably linked to an expression regulatory element which is capable of modulating the expression of the recombinant polynucleotide. In embodiment, the regulatory element may include any of a promoter, enhancer or poly-adenylation signal.

In some embodiments, the vector is an expression vector. The expression vector may be eukaryotic, prokaryotic or vector viral.

In another aspect, the invention provides genetically modified cells which include a recombinant polynucleotide, in which the recombinant polynucleotide includes at least 40 contiguous nucleotides of SEQ ID NO: 9 or its complement. In one embodiment, the genetically modified cells include a recombinant polynucleotide having a nucleotide sequence at least 95% identical to SEQ ID NO: 1. In other embodiments, the genetically modified cells include a recombinant polynucleotide having the nucleotide sequence of SEQ ID NO: 1. Also included are genetically modified cells that contain any of the vectors described above. In some embodiments, the recombinant polynucleotide is a cDNA construct while in other embodiments, the recombinant polynucleotide is genomic construct.

In some embodiments of the above aspect of the invention, the genetically modified cells are eukaryotic. In some embodiments, the genetically modified cells express a recombinant polypeptide, in which the recombinant polypeptide has Abl kinase activity.

In another aspect, the invention provides methods of identifying a compound for treating CML patients, including contacting genetically modified cells with a candidate compound, and assessing the effect of the candidate compound on the cells, in which the candidate compound is identified as a compound for treating CML patients when the effect of the candidate compound on the genetically modified cells is beneficial in the treatment of CML. In this method, the genetically modified cells express a BCR-ABL recombinant polypeptide having kinase activity, the polypeptide being encoded by some of the above described recombinant polynucleotides.

In some embodiments, the candidate compound is a kinase inhibitor. In some embodiments, the candidate compound is an inhibitor for BCR-ABL. In some embodiments, the candidate compound is selected from the group consisting of imatinib, dasatinib, bosutinib, and nilotinib.

In one embodiment, the effect of the compound on the cells is a reduction in the viability or growth rate of the cells or reduction of at least one activity of the expressed recombinant polypeptide. In one preferred embodiment, the effect is a reduction in the viability of the genetically modified cells. In another embodiment, the reduction in viability is reflected by an increase in apoptosis of the genetically modified cells. In one embodiment, the effect is the effect on the kinase activity of the expressed recombinant polypeptide. In one embodiment, the kinase activity is determined by testing the phosphorylation status of a substrate of BCR-ABL. In another embodiment, the effect is a reduction in growth rate of the cells. In one embodiment, the growth rate is measured by the amount of DNA synthesis. In one preferred embodiment, the cells are resistant to imatinib. In one embodiment, the cells are CML cells. In one preferred embodiment, the CML cells are K562 cells.

In another aspect, the invention provides a method for predicting likelihood for resistance of a CML patient with a BCR/Abl translocation to treatment with one or more BCR-ABL kinase inhibitors. In one approach, the method includes assessing the bcr-abl mRNA of the CML patient for the presence or absence of a polynucleotide sequence comprising at least 40 contiguous nucleotides of SEQ ID NO: 9 or a complement thereof; and further assessing for the presence or absence of at least one mutation in the abl portion of the bcr-abl gene. The presence of the polynucleotide sequence or a complement thereof in bcr-abl mRNA and presence of at least one mutation in the abl portion of the bcr-abl gene indicates that the patient has an increased likelihood of being resistant to treatment with one or more BCR-ABL kinase inhibitors relative to a CML patent having the mutation alone. In one embodiment, one or more kinase inhibitors are selected from a group consisting of imatinib, nilotinib, bosutinib, and dasatinib. In one preferred embodiment, the kinase inhibitor is imatinib.

In another approach, the method for predicting likelihood for resistance of a CML patient with a BCR/Abl translocation to treatment with one or more BCR-ABL kinase inhibitors includes assessing the bcr-abl mRNA of the CML patient for the amount of RNA encoding a full length BCR-ABL and the amount of RNA encoding a BCR-ABL insertion/truncation splice variant encoded by at least 40 contiguous nucleotides of SEQ ID NO: 9 or a complement thereof; wherein the likelihood of resistance increases with increasing amounts of BCR-ABL mRNA insertion/truncation splice variant relative to full length BCR-ABL encoding mRNA. Patients expressing a higher level of the BCR-ABL insertion/truncation splice variant (i.e., having increased likelihood of resistance) are candidates for treatment using higher doses of BCR-ABL kinase inhibitors, relative to the dosage administered to patients expressing lower amounts (or no) BCR-ABL insertion/truncation splice variant.

In one embodiment, the BCR-ABL splice variant is encoded by sequence that comprises SEQ ID NO: 1. In another embodiment, the amounts of bcr-abl mRNA are determined using primers described in any of invention kits. In another embodiment, the amounts of bcr-abl mRNA are determined using PCR, preferably a nested PCR. In another embodiment, the sizes of the amplified products are between 200-300 bp in length.

In another aspect, the invention provides an antibody that specifically binds to an epitope having an amino acid sequence of SEQ ID NO: 10 or SEQ ID NO: 12, wherein the antibody specifically binds to an insertion/truncation mutant of BCR-ABL protein but does not bind to BCR-ABL protein without the insertion/truncation mutation. In some embodiments of the above aspects of the invention, the antibody is a monoclonal antibody.

In another aspect, the invention provides a kit for detecting the presence or absence of bcr-abl insertion/truncation splice variant mRNA including a first primer and a second primer, in which the first primer anneals to a portion of bcr exon b2 and the second primer anneals to a region at the junction of abl exon 9 and 10. The use of the first primer and the second primer in an amplification reaction is capable of generating an amplicon. The kit also may include a detectably labeled probe capable of hybridizing to the amplicon, in which the probe hybridizes to at least 10 contiguous nucleotides of SEQ ID NO: 4 or a complement thereof. In preferred embodiments, the first primer is SEQ ID NO: 5 or its complement. In another embodiment, the second primer is SEQ ID NO: 6 or its complement.

In another aspect, the invention provides a kit for detecting the presence or absence of bcr-abl insertion/truncation splice variant mRNA including a first primer and a second primer, in which the first primer anneals to a portion of bcr exon b2 and the second primer anneals to a region at the junction of abl exon 9 and 10 to generate a first amplicon, and a third and a fourth primer, in which the third primer anneals to a portion of abl exon 8 and the fourth primer anneals to a portion of abl exon 9 to generate a second amplicon. In preferred embodiments, the kit also includes a detectably labeled probe capable of hybridizing to at least 10 contiguous nucleotides of SEQ ID NO: 4 or its complement. In preferred embodiments, the first primer is SEQ ID NO: 5 or its complement. In another embodiment, the second primer is SEQ ID NO: 6 or its complement. In some embodiments, the third primer is SEQ ID NO: 22 or its complement. In some embodiments, the fourth primer is SEQ ID NO: 23 or its complement.

In another aspect, the invention provides a method for detecting the presence or absence BCR-ABL insertion/truncation splice variant in a sample including detecting the presence or absence of a polypeptide that includes at least 15 contiguous amino acids of SEQ ID NO: 12, in which the presence of at least 15 contiguous amino acids of SEQ ID NO: 12 in a polypeptide identifies the presence of a insertion/truncation mutant of BCR-ABL protein in a sample. In some embodiments, the presence or absence of the polypeptide is determined by using an antibody that specifically binds to an epitope including the amino acid sequence of SEQ ID NO: 12 in which the antibody specifically binds to an insertion/truncation mutant of BCR-ABL protein and not to a BCR-ABL protein without such mutation.

In some embodiments, the presence or absence of the polypeptide is determined by assessing the size of the BCR-ABL protein. In another embodiment, the presence or absence of the polypeptide is determined by western blotting. In another embodiment, the presence or absence of the polypeptide is determined by flow cytometry. In some embodiments, the method simultaneously detects wild-type BCR-ABL protein and the insertion/truncation mutant of BCR-ABL protein.

In another aspect, the invention provides a kit for detecting the presence or absence of BCR-ABL insertion/truncation splice variant including an antibody that specifically binds to an epitope including 15 contiguous amino acids of SEQ ID NO: 12.

In another aspect, the invention provides a kit for detecting the presence or absence of BCR-ABL insertion truncation splice variant including an antibody that specifically binds to an epitope including 10 contiguous amino acids of SEQ ID NO: 10.

In another aspect, the invention provides a method for predicting the likelihood for drug resistance of a CML patient with a BCR/Abl translocation to treatment with one or more BCR-ABL kinase inhibitors. In an embodiment, the method includes assessing the BCR-ABL polypeptide of the CML patient for the presence or absence of a polypeptide that includes at least 15 contiguous amino acids of SEQ ID NO: 12, in which the presence of at least 15 contiguous amino acids of SEQ ID NO: 12 in a polypeptide indicates an increased likelihood of being resistant to treatment with BCR-ABL kinase inhibitors. In another embodiment, the method includes assessing the BCR-ABL polypeptide of the CML patient for the presence or absence of a polypeptide that includes at least 10 contiguous amino acids of SEQ ID NO: 10, in which the presence of at least 10 contiguous amino acids of SEQ ID NO: 10 in a polypeptide indicates an increased likelihood of being resistant to treatment with BCR-ABL kinase inhibitors In one embodiment, the kinase inhibitors are selected from a group consisting of imatinib, nilotinib, bosutinib, and dasatinib. In one preferred embodiment, the kinase inhibitor is imatinib.

In another approach, the method for predicting likelihood for resistance of a CML patient with a BCR/Abl translocation to treatment with one or more BCR-ABL kinase inhibitors includes assessing the BCR-ABL protein of the CML patient for the amount of full length BCR-ABL protein and the amount of an insertion/truncation mutant of BCR-ABL protein; wherein the likelihood of resistance increases with increasing amounts of insertion/truncation mutant of BCR-ABL protein relative to full length BCR-ABL protein. In an embodiment, the method includes assessing the BCR-ABL polypeptide of the CML patient for the amount of a polypeptide that includes at least 15 contiguous amino acids of SEQ ID NO: 12 and the amount of full length BCR-ABL polypeptide, wherein the likelihood of resistance increases with increasing amounts of BCR-ABL polypeptide that includes at least 15 contiguous amino acids of SEQ ID NO: 12 relative to full length BCR-ABL polypeptide. In another embodiment, the method includes assessing the BCR-ABL polypeptide of the CML patient for the amount of a polypeptide that includes at least 10 contiguous amino acids of SEQ ID NO: 10 and the amount of full length BCR-ABL polypeptide, wherein the likelihood of resistance increases with increasing amounts of BCR-ABL polypeptide that includes at least 10 contiguous amino acids of SEQ ID NO: 10 relative to full length BCR-ABL polypeptide. Patients expressing a higher level of the BCR-ABL insertion/truncation mutant protein (i.e., having increased likelihood of resistance) are candidates for treatment using higher doses of BCR-ABL kinase inhibitors, relative to the dosage administered to patients expressing lower amounts (or no) BCR-ABL insertion/truncation mutant protein.

In some embodiments, the presence or absence of the polypeptide is determined by assessing the size of the BCR-ABL protein. In another embodiment, the presence or absence of the polypeptide is determined by western blotting. In another embodiment, the presence or absence of the polypeptide is determined by flow cytometry. In some embodiments, the method simultaneously detects wild-type BCR-ABL protein and the insertion/truncation mutant of BCR-ABL protein.

In an embodiment, the invention provides a method for treating a CML patient found to be at increased risk of drug resistance by any of the above methods for assessing increased risk, by administering an increased dose of BCR-ABL kinase inhibitor relative to a CML patient not found to be at increased risk of drug resistance. In an embodiment, the invention provides a method for treating a CML patient found to be at increased risk of drug resistance by any of the above methods for assessing increased risk, by administering at least two kinase inhibitors to the patient. The kinase inhibitors may act synergistically. At least one kinase inhibitor may be a tyrosine kinase inhibitor. At least one kinase inhibitor may be imatinib, dasatinib, bosutinib, nilotinib, VX-480, or homoharringtonine (HHT). At least one kinase inhibitor may be a non-tyrosine kinase inhibitor.

In another aspect, the invention provides a method for treating patients diagnosed as having CML by administering synergistic combinations of tyrosine kinase inhibitors. Synergistic combinations may be identified using the methods provided herein. In some embodiments, the synergistic combinations include at least one of imatinib, nilotinib, and HHT. Specific synergistic combinations include, for example, imatinib/nilotinib and imatinib/HHT. The individual component drugs in the combination may be administered simultaneously or at different times. For example, imatinib and nilotinib, when used in combination may be administered simultaneously, while the components of the imatinib/HHT combination may be administered at different times. When administered at different times, the component drugs in a synergistic combination may be administered within 1, 2, 4, 8, 12, 24, 48 hours (or more) of each other. In one embodiment of the imatinib/HHT combination, HHT is administered about 24 hours prior to imatinib during each cycle of administration. In another embodiment, HHT is first administered alone, followed by a simultaneous administration of an imatinib/HHT combination within 24 hours.

As used herein, "subject" or "individual" is meant a human or any other animal that has cells that may contain a BCR/Abl translocation. A subject can be a patient, which refers to a human presenting to a medical provider for diagnosis or treatment of a disease. A human includes pre and post natal forms.

"Patient" as used herein, refers to one who receives medical care, attention or treatment. As used herein, the term is meant to encompass a person diagnosed with a disease as well as a person who may be symptomatic for a disease but who has not yet been diagnosed.

"Sample" or "patient sample" as used herein includes biological samples such as tissues and bodily fluids. "Bodily fluids" may include, but are not limited to, blood, serum, plasma, saliva, cerebral spinal fluid, pleural fluid, tears, lactal duct fluid, lymph, sputum, urine, amniotic fluid, and semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin.

"Plasma" as used herein refers to acellular fluid found in blood. "Plasma" may be obtained from blood by removing whole cellular material from blood by methods known in the art (e.g., centrifugation, filtration, and the like). As used herein, "peripheral blood plasma" refers to plasma obtained from peripheral blood samples.

"Serum" as used herein includes the fraction of plasma obtained after plasma or blood is permitted to clot and the clotted fraction is removed.

"Nucleic acid" or "nucleic acid sequence" as used herein refers to an oligonucleotide, nucleotide or polynucleotide, and fragments or portions thereof, which may be single or double stranded, and represent the sense or antisense strand. A nucleic acid may include DNA or RNA, and may be of natural or synthetic origin and may contain deoxyribonucleotides, ribonucleotides, or nucleotide analogs in any combination.

Non-limiting examples of polynucleotides include a gene or gene fragment, genomic DNA, exons, introns, mRNA, tRNA, rRNA, ribozymes, cDNA, recombinant polynucleotides, branched polynucleotides, plasmids, vectors, isolated DNA of any sequence, isolated RNA of any sequence, synthetic nucleic acid, nucleic acid probes and primers. Polynucleotides may be natural or synthetic. Polynucleotide may comprise modified nucleotides, such as methylated nucleotides and nucleotide analogs, uracyl, other sugars and linking groups such as fluororibose and thiolate, and nucleotide branches. A nucleic acid may be modified such as by conjugation, with a labeling component. Other types of modifications included in this definition are caps, substitution of one or more of the naturally occurring nucleotides with an analog, and introduction of chemical entities for attaching the polynucleotide to other molecules such as proteins, metal ions, labeling components, other polynucleotides or a solid support. Nucleic acid may include nucleic acid that has been amplified (e.g., using polymerase chain reaction).

A fragment of a nucleic acid generally contains at least about 15, 20, 25, 30, 35, 40, 45, 50, 75, 100, 200, 300, 400, 500, 1000 nucleotides or more. Larger fragments are possible and may include about 2,000, 2,500, 3,000, 3,500, 4,000, 5,000 7,500, or 10,000 bases.

"Gene" as used herein refers to a DNA sequence that comprises control and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained.

"cDNA" as used herein refers to complementary or copy polynucleotide produced from an RNA template by the action of RNA-dependent DNA polymerase activity (e.g., reverse transcriptase). cDNA can be single stranded, double stranded or partially double stranded. cDNA may contain unnatural nucleotides. cDNA can be modified after being synthesized. cDNA may comprise a detectable label.

Although a sequence of the nucleic acids may be shown in the form of DNA, a person of ordinary skill in the art recognizes that the corresponding RNA sequence will have a similar sequence with the thymine being replaced by uracil i.e. "t" with "u".

"Codon" as used herein refers to a sequence of three adjacent nucleotides (either RNA or DNA) constituting the genetic code that determines the insertion of a specific amino acid in a polypeptide chain during protein synthesis or the signal to stop protein synthesis. The term "codon" is also used to refer to the corresponding (and complementary) sequences of three nucleotides in the messenger RNA into which the original DNA is transcribed.

"Coding sequence" as used herein refers to a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

"Non-coding sequence" as used herein refers to a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

"Wild-type" as used herein refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. "Wild-type" may also refer to the sequence at a specific nucleotide position or positions, or the sequence at a particular codon position or positions, or the sequence at a particular amino acid position or positions.

"Mutant", or "modified" as used herein refers to a gene or gene product which displays modifications in sequence and or functional properties (i.e., altered characteristics) when compared to the wild-type gene or gene product. "Mutant", or "modified" also refers to the sequence at a specific nucleotide position or positions, or the sequence at a particular codon position or positions, or the sequence at a particular amino acid position or positions which displays modifications in sequence and or functional properties (i.e., altered characteristics) when compared to the wild-type gene or gene product.

"Mutation" as used herein refers to a nucleic acid with at least a single nucleotide variation relative to the normal sequence or wild-type sequence. In the context of polypeptide, "mutation" refers to at least a single amino acid variation in a polypeptide sequence relative to the normal sequence or wild-type sequence. A mutation may include a substitution, a deletion, an inversion or an insertion. With respect to an encoded polypeptide, a mutation may be "silent" and result in no change in the encoded polypeptide sequence or a mutation may result in a change in the encoded polypeptide sequence. For example, a mutation may result in a substitution in the encoded polypeptide sequence. A mutation may result in a frameshift with respect to the encoded polypeptide sequence.

The convention "NTwt###NTmut" is used to indicate a mutation that results in the wild-type nucleotide NTwt at position ### in the nucleic acid being replaced with mutant NTmut. The convention "AAwt###AAmut" is used to indicate a mutation that results in the wild-type amino acid AAwt at position ### in the polypeptide being replaced with mutant AAmut.

"Protein", "peptide", "polypeptide" and "polypeptide fragment" as used herein are used interchangeably to refer to polymers of amino acids ("an amino acid sequence") of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation of modification, such as conjugation with a labeling or bioactive component.

"Identity" and "identical" as used herein refer to a degree of identity between sequences. There may be partial identity or complete identity. A partially identical sequence is one that is less than 100% identical to another sequence. Preferably, partially identical sequences have an overall identity of at least 70% or at least 75%, more preferably at least 80% or at least 85%, most preferably at least 90% or at least 95% or at least 99%. Sequence identity determinations may be made for sequences which are not fully aligned. In such instances, the most related segments may be aligned for optimal sequence identity by and the overall sequence identity reduced by a penalty for gaps in the alignment.

"Insertion" or "addition", as used herein refers to a change in an amino acid or nucleotide sequence resulting in the addition of one or more amino acid residues or nucleotides respectively, as compared to the naturally occurring molecule.

"Truncation", as used herein refers to a change in an amino acid or nucleic acid sequence resulting in the loss of one or more positions in the sequence where amino acids residues or nucleotides, respectively, would be present as compared to the naturally occurring molecule.

"Insertion/truncation mutation" or "insertion/truncation mutant" in the context of BCR-ABL as used herein refers to a BCR-ABL protein with the addition of new amino acids at the c-terminal region of the protein and deletion of one or more amino acids at the c-terminal region of the protein as compared to the exemplary reference BCR-ABL protein amino acid sequence of SEQ ID NO: 11, such that the resultant protein will have a different c-terminal amino acid sequence than that of SEQ ID NO: 11. In preferred embodiments, such alternative splicing may result from insertion of a 35 bp portion of intron 8 into the junction of exon 8 and 9 in bcr-abl mRNA by alternative splicing, as depicted in FIG. 1. The insertion/truncation mutant also is referred to herein as "35 INS BCR-ABL."

Several variants of BCR-ABL are known in the art. Exemplary BCR-ABL protein sequences include but are not limited to NCBI protein database accession numbers: ABX82708, ABX82702, AAA35594.

"Heterozygous" as used herein refers to having different alleles at one or more genetic loci in homologous chromosome segments. "Heterozygous" also refers to a sample, a cell, a cell population or an organism in which different alleles at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiments, the smaller peak is at least about 10% of the larger peak. In other embodiments, the smaller peak is at least about 5% of the larger peak. In other embodiments, a minimal amount of the smaller peak is detected.

"Homozygous" as used herein refers to having identical alleles at one or more genetic loci in homologous chromosome segments. "Homozygous" may also refer to a sample, a cell, a cell population or an organism in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

"Hemizygous" as used herein refers to a gene or gene segment being present only once in the genotype of a cell or an organism because the second allele is deleted. As used herein "hemizygous" may also refer to a sample, a cell, a cell population or an organism in which a allele at one or more genetic loci may be detected only once in the genotype.

"Zygosity status" as used herein refers to a sample, a cell population, or an organism as appearing heterozygous, homozygous, or hemizygous as determined by testing methods known in the art and described herein. The term "zygosity status of a nucleic acid" means determining whether the source of nucleic acid appears heterozygous, homozygous, or hemizygous. The "zygosity status" may refer to differences in a single nucleotide in a sequence. In some methods, the zygosity status of a sample with respect to a single mutation may be categorized as homozygous wild-type, heterozygous (i.e., one wild-type allele and one mutant allele), homozygous mutant, or hemizygous (i.e., a single copy of either the wild-type or mutant allele). Because direct sequencing of plasma or cell samples as routinely performed in clinical laboratories does not reliably distinguish between hemizygosity and homozygosity, in some embodiments, these classes are grouped. For example, samples in which no or a minimal amount of wild-type nucleic acid is detected are termed "hemizygous/homozygous mutant." In some embodiments, a "minimal amount" may be between about 1-2%. In other embodiments, a minimal amount may be between about 1-3%. In still other embodiments, a "minimal amount" may be less than 1%.

"Hybridize" or "hybridization" as used herein refers to the pairing of substantially complementary nucleotide sequences (strands of nucleic acid) to form a duplex or heteroduplex through formation of hydrogen bonds between complementary base pairs. Hybridization and the strength of hybridization (i.e., the strength of the association between the nucleic acids) is influenced by such factors as the degree of complementarity between the nucleic acids, stringency of the conditions involved, and the $T_m$ of the formed hybrid. An oligonucleotide or polynucleotide (e.g., a probe or a primer) that is specific for a target nucleic acid will "hybridize" to the target nucleic acid under suitable conditions.

"Specific hybridization" as used herein refers to an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

"Stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

"Complement" as used herein refers to the complementary sequence to a nucleic acid according to standard Watson/Crick pairing rules. A complement sequence can also be a sequence of RNA complementary to the DNA sequence or its complement sequence, and can also be a cDNA. The complement of a nucleic acid sequence as used herein refers to an polynucleotide which, when aligned with the nucleic acid sequence such that the 5' end of one sequence is paired with the 3' end of the other, is in "antiparallel association". For example, for the sequence "5'-A-G-T-3'" is complementary to the sequence "3'-T-C-A-5". Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

"Substantially complementary" as used herein refers to two sequences that hybridize under stringent hybridization conditions. The skilled artisan will understand that substantially complementary sequences need not hybridize along their entire length.

Oligonucleotides can be used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

"Oligonucleotide" as used herein refers to a molecule that has a sequence of nucleic acid bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group in this position. Oligonucleotides also may include derivatives, in which the hydrogen of the hydroxyl group is replaced with organic groups, e.g., an allyl group. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. The oligonucleotide may be generated in any manner, including, for example, chemical synthesis, DNA replication, reverse transcription, PCR, or a combination thereof. The oligonucleotide may be modified. For example, the oligonucleotide may be labeled with an agent that produces a detectable signal (e.g., a fluorophore).

"Primer" as used herein refers to an oligonucleotide that is capable of acting as a point of initiation of synthesis when placed under conditions in which primer extension is initiated (e.g., primer extension associated with an application such as PCR). The primer is complementary to a target nucleotide sequence and it hybridizes to a substantially complementary sequence in the target and leads to addition of nucleotides to the 3'-end of the primer in the presence of a DNA or RNA polymerase. The 3'-nucleotide of the primer should generally be complementary to the target sequence at a corresponding nucleotide position for optimal expression and amplification. An oligonucleotide "primer" may occur naturally, as in a purified restriction digest or may be produced synthetically. The term "primer" as used herein includes all forms of primers that may be synthesized including peptide nucleic acid primers, locked nucleic acid primers, phosphorothioate modified primers, labeled primers, and the like.

Primers are typically between about 10 and about 100 nucleotides in length, preferably between about 15 and about 60 nucleotides in length, more preferably between about 20 and about 50 nucleotides in length, and most preferably between about 25 and about 40 nucleotides in length. In some embodiments, primers can be at least 8, at least 12, at least 16, at least 20, at least 25, at least 30, at least 35, at least 40, at least 45, at least 50, at least 55, at least 60 nucleotides in length. An optimal length for a particular primer application may be readily determined in the manner described in H. Erlich, PCR Technology, Principles and Application for DNA Amplification (1989).

"Probe" as used herein refers to nucleic acid that interacts with a target nucleic acid via hybridization. A probe may be fully complementary to a target nucleic acid sequence or partially complementary. The level of complementarity will depend on many factors based, in general, on the function of the probe. A probe or probes can be used, for example to detect the presence or absence of a mutation in a nucleic acid sequence by virtue of the sequence characteristics of the target. Probes can be labeled or unlabeled, or modified in any of a number of ways well known in the art. A probe may specifically hybridize to a target nucleic acid.

Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. A probe may be fully complementary to a target nucleic acid sequence or partially complementary. A probe may be used to detect the presence or absence of a target nucleic acid. Probes are typically at least about 10, 15, 20, 25, 30, 35, 40, 50, 60, 75, 100 nucleotides or more in length.

"Target nucleic acid" as used herein refers to a nucleic acid molecule (e.g., DNA or RNA) containing a sequence that has at least partial complementarity with a primer oligonucleotide and/or a probe oligonucleotide. A probe may specifically hybridize to a target nucleic acid.

"Flanking" as used herein refers to a primer hybridizes to a target nucleic acid adjoining a region of interest sought to be amplified on the target. The skilled artisan will understand that preferred primers are pairs of primers that hybridize upstream of a region of interest, one on each strand of a target double stranded DNA molecule, such that nucleotides may be added to the 3' end of the primer by a suitable DNA polymerase. Primers that flank mutant JAK2 sequences do not actually anneal to the mutant sequence but rather anneal to sequence that adjoins the mutant sequence.

"Amplification" or "amplifying" as used herein refers to the production of additional copies of a nucleic acid sequence. Amplification may be exponential or linear. A target nucleic acid may be either DNA or RNA. The sequences amplified in this manner form an "amplicon" or "amplification product". Amplification is generally carried out using polymerase chain reaction (PCR) technologies known in the art. While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols (1990), Innis et al., Eds., Academic Press, San Diego, CA, pp 13-20; Wharam, et al., Nucleic Acids Res. (2001), Jun. 1; 29(11): E54-E54; Hafner, et al., Biotechniques (2001), 4:852-6, 858, 860.

"Amplification reaction system" as used herein refers to any in vitro means for multiplying the copies of a target sequence of nucleic acid. The term "amplification reaction mixture" refers to an aqueous solution comprising the various reagents used to amplify a target nucleic acid.

"Assay" or "assaying" as used herein refers to qualitative or quantitative analysis or testing.

"Sequencing" as used herein refers to determining the sequence of a polynucleotide (or protein) using methods that determine the base identity at multiple base positions or determine the base identity at a single position. The term "direct sequencing" means that the letters of the genetic code of the molecule of interest are sequenced for reading. For example, if the molecule of interest is RNA, then the letters of RNA are read directly rather than the DNA sequence as alternative splicing during translation may result in different RNA sequences.

"Detecting" as used herein in context of detecting a signal from a detectable label to indicate the presence of a nucleic acid of interest in the sample (or the presence or absence of a protein of interest in the sample) does not require the method to provide 100% sensitivity and/or 100% specificity. As is well known, "sensitivity" is the probability that a test is positive, given that the person has a genomic nucleic acid sequence, while "specificity" is the probability that a test is negative, given that the person does not have the genomic nucleic acid sequence. A sensitivity of at least 50% is preferred, although sensitivities of at least 60%, at least 70%, at least 80%, at least 90% and at least 99% are clearly more preferred. A specificity of at least 50% is preferred, although specificity of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

"Detectable label" as used herein refers to a molecule or a compound or a group of molecules or a group of compounds used to identify a nucleic acid or protein of interest. In some cases, the detectable label may be detected directly. In other cases, the detectable label may be a part of a binding pair, which can then be subsequently detected. Signals from the detectable label may be detected by various means and will depend on the nature of the detectable label. Detectable labels may be isotopes, fluorescent moieties, colored substances, and the like. Examples of means to detect detectable label include but are not limited to spectroscopic, photochemical, biochemical, immunochemical, electromagnetic, radiochemical, or chemical means, such as fluorescence, chemifluoresence, or chemiluminescence, or any other appropriate means.

"TaqMan® PCR detection system" as used herein refers to a method for real time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

"Vector" as used herein refers to a recombinant DNA or RNA plasmid or virus that comprises a heterologous polynucleotide capable of being delivered to a target cell, either in vitro, in vivo or ex-vivo. The heterologous polynucleotide can comprise a sequence of interest and can be operably linked to another nucleic acid sequence such as promoter or enhancer and may control the transcription of the nucleic acid sequence of interest. As used herein, a vector need not be capable of replication in the ultimate target cell or subject. The term vector may include expression vector and cloning vector.

Suitable expression vectors are well-known in the art, and include vectors capable of expressing a polynucleotide operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome.

"Promoter" as used herein refers to a segment of DNA that controls transcription of polynucleotide to which it is operatively linked. Promoters, depending upon the nature of the regulation, may be constitutive or regulated. Exemplary eukaryotic promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter. Exemplary promoters suitable for use with prokaryotic hosts include T7 promoter, beta-lactamase promoter, lactose promoter systems, alkaline phosphatase promoter, a tryptophan (trp) promoter system, and hybrid promoters such as the tac promoter.

"Antibody" as used herein refers to a polypeptide, at least a portion of which is encoded by at least one immunoglobulin gene, or fragment thereof, and that can bind specifically to a desired target molecule. The term includes naturally-occurring forms, as well as fragments and derivatives. Fragments within the scope of the term "antibody" include those produced by digestion with various proteases, those produced by chemical cleavage and/or chemical dissociation, and those produced recombinantly, so long as the fragment remains capable of specific binding to a target molecule. Among such fragments are Fab, Fab', Fv, F(ab)'$_2$, and single chain Fv (scFv) fragments. Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., Marasco (ed.), Intracellular Antibodies: Research and Disease Applications, Springer-Verlag New York, Inc. (1998) (ISBN: 3540641513). As used herein, antibodies can be produced by any known technique, including harvest from cell culture of native B lymphocytes, harvest from culture of hybridomas, recombinant expression systems, and phage display.

"Specifically binds to an epitope" as used herein in the context of an antibody refers to binding of an antibody specifically to an epitope such that the antibody can distinguish between two proteins with and without such epitope.

In preferred embodiments, antibodies binding to epitopes comprising SEQ ID NO: 12 or SEQ ID NO: 10, specifically binds to insertion/truncation mutant of BCR-ABL proteins and can distinguish from BCR-ABL proteins without such mutation.

"Neoplastic disease" as used herein refers to a condition characterized by an abnormal growth of new cells such as a tumor. A neoplasm includes solid and non-solid tumor types such as a carcinoma, sarcoma, leukemia and the like. A neoplastic disease may be malignant or benign.

"CML patient" as used herein refers to a patient diagnosed with CML or suspected of having CML. One of ordinary skill in the art is capable of diagnosing CML using suitable diagnostic criteria.

"Diagnose" or "diagnosis" or "diagnosing" as used herein refer to distinguishing or identifying a disease, syndrome or condition or distinguishing or identifying a person having a particular disease, syndrome or condition. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease.

"Treatment," "treating," or "treat" as used herein refers to care by procedures or application that are intended to relieve illness or injury. Although it is preferred that treating a condition or disease will result in an improvement of the condition, the term treating as used herein does not indicate, imply, or require that the procedures or applications are at all successful in ameliorating symptoms associated with any particular condition. Treating a patient may result in adverse side effects or even a worsening of the condition which the treatment was intended to improve.

"Monitoring treatment of CML patient" as used herein refers to the process by which the skilled artisan can predict the course or outcome of treatment of CML patients. In some embodiments, such treatment of CML patients may include treating CML patients with tyrosine kinase inhibitors for BCR-ABL protein. Exemplary BCR-ABL tyrosine kinase inhibitors include, but not limited to imatinib, dasatinib, nilotinib, Bosutinib (SKI-606) Aurora kinase inhibitor VX-680. In one preferred embodiment, the tyrosine kinase inhibitor for BCR-ABL is imatinib.

"Isolated", as used herein when referring to a nucleic acid or protein molecule means that the molecule is apart from its natural environment and/or is substantially separated from other cellular components which naturally accompany such molecule. For example, any nucleic acid or protein that has been produced synthetically (e.g., by serial base condensation) is considered to be isolated. Likewise, nucleic acids or proteins that are recombinantly expressed, cloned, produced by a synthetic in vitro reaction are considered to be isolated. An isolated nucleic acid or protein is at least 25% free, preferably at least 30% free, preferably at least 40% free, preferably at least 50% free, preferably at least 60% free, more preferably at least 75% free, and most preferably at least 90% free from other components with which it is naturally associated.

"Substantially pure" as used herein with reference to a nucleic acid (or protein), means that the nucleic acid (or protein) represents more than 50% of the biological molecules in a sample. The sample may exist in solution or as a dry preparation.

"Substantially all" as used herein means between about 60-100%, more preferably, between about 70-100%; more preferably between about 80-100%, more preferably between about 90-100%, and more preferably between about 95-100%.

"Including" as used herein has the same meaning as the term comprising.

"About" as used herein means in quantitative terms, plus or minus 10%.

"Ratio" as used herein refers to the relation in degree or number between two similar things. For example, the relative amount of mutant to wild-type nucleic acid in a sample may be referred to as a ratio of wild-type to mutant nucleic acid.

BRIEF DESCRIPTION OF FIGURES

FIG. 1 provides a sequence for an exemplary segment of bcr-abl genomic nucleic acid showing exon 8, intron 8 and exon 9. The exons are depicted in upper case letters and the intron in lowercase letters with the exception that the bold underlined uppercase sequence within intron 8 is highlighted to show the 35 bp segment of intron 8 which inserts into the junction of exons 8 and 9 forming the 35 INS BCR-ABL.

FIG. 2 shows a portion of an exemplary cDNA sequence of bcr-abl insertion/truncation splice variant. Sequences derived from abl exons 8 and 9 are depicted in lowercase. Sequence derived from the 35 bp insert from abl intron 8 is shown in bold uppercase. The 3'-terminal region of abl exon 8 and 5'-terminal region of exon 9 flanking the 35 bp insert is shown in bold lowercase and underlined.

FIG. 3. shows the amino acid sequence alignment of the c-terminus of wild type ABL protein (SEQ ID NO: 29) and translated amino acid sequence of the bcr-abl mRNA splice variant (SEQ ID NO: 30) resulting in the insertion/truncation mutant 35 INS BCR-ABL described in FIG. 2. Position numbering is based on the wild type ABL protein (GenBank accession number AAA51561). The 10 abl intron 8 derived amino acids begins at amino acid 475, replacing C with Y and ends with amino acid 484 (but shown as position 485 due to the alignment).

FIGS. 5A-5B show maps of expression vectors pMIG/bcr-abl (wildtype) and pMIG/35 INS bcr-abl (splice variant).

FIG. 6 shows the relative frequency of individual BCR-ABL kinase domain mutations detected in a group of 245 patients, 219 of which have CML and 26 of which have Ph-positive acute lymphoblastic leukemia. The numbering of amino acids is based on the Abl protein variant B (which includes Abl exon 1b but not exon 1a). The letters inside the circles denote the amino acid encoded by the corresponding mutated nucleotide. At some positions, 2 or 3 possible mutant nucleotides encode different amino acids. The percentage of patients in the series with each mutation specified on the y axis is color-coded as shown in the box.

FIG. 10B shows six patient samples with various percentages of 35 INS BCR-ABL splice variant evaluated by western blotting using BCR 7c6 antibody for immunoprecipitation and ABL K12 for the developing antibody. The percentages of 35 INS BCR-ABL relative to full length BCR-ABL was determined by RT/PCR coupled with heminested PCR as described in Example 2.

FIG. 11 shows an exemplary amino acid sequence of a full length BCR-ABL protein without the insertion/truncation mutation (SEQ ID NO: 11).

FIG. 12 shows an exemplary amino acid sequence of the 35 INS BCR-ABL splice variant. The ten new amino acids generated at the c-terminus of the protein due the alternate splicing are underlined (SEQ ID NO: 20).

FIG. 13 shows an exemplary nucleotide sequence of intron 8 of abl (nucleotides 148-1,647 of SEQ ID NO: 3). The bold and underlined sequence represents an exemplary sequence of the 35 bases inserted into the junction of abl exons 8 and 9 in the 35 INS BCR-ABL splice variant.

FIG. 14 shows an exemplary amino acid sequence of wild-type Abl protein (SEQ ID NO: 24).

FIG. 15 shows an exemplary amino acid sequence of insertion/truncation mutant of Abl protein (SEQ ID NO: 25) due to the 35 INS BCR-ABL alternate splicing. The ten new amino acids generated at the c-terminus of the protein due the alternate splicing are underlined FIGS. 16A-16B shows an exemplary cDNA sequence of bcr-abl (SEQ ID NO: 19) without 35 INS BCR-ABL alternate splicing. The junction of abl exons 8 and 9 "TG" is bolded and underlined.

FIGS. 17A-17C shows an exemplary cDNA sequence of alternately spliced bcr-abl (SEQ ID NO: 26). The 35 base insert from abl intron 8 is shown bolded and underlined.

FIGS. 18A-18C show the effect of 35 INS BCR-ABL truncation mutant on resistance to selected kinase inhibitors in CML cells. (A) The effect of the kinase inhibitor drugs on cell proliferation as measured by MTT. (B) Induction of apoptosis measured by caspase-3 activation. (C) FACS analysis of transfected K562 cells after imatinib mesylate treatment.

DETAILED DESCRIPTION OF THE INVENTION

Figure 4:
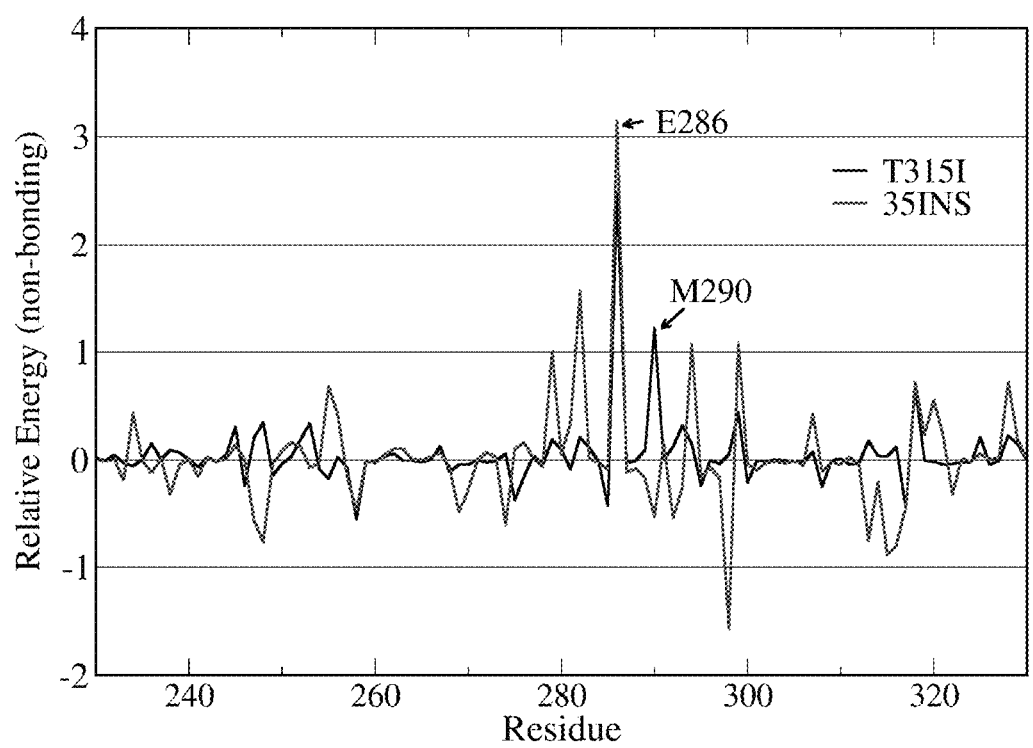
FIG. 4. shows the relative non-bonding interaction energies (compared to wild-type) from simulations between a selected set of amino acids from the two indicated BCR-ABL mutants and imatinib. Relative non-bonding interaction energies are represented as the average over the last 15 ns simulations with a sampling frequency of 1 ps. Unit is Kcal/mol.

Embodiments of the present invention are based on a bcr-abl splice variant that encodes a C-terminal truncated BCR-ABL protein that renders cells resistant to treatment with kinase domain inhibitors such as imatinib. As demonstrated herein, increasing amounts of the truncation mutant correlate directly with resistance and a majority of drug-resistant CML patients have at least some cells expressing the truncation mutation. Embodiments of the invention described herein include polynucleotides which encode all or portions of the splice variant and cells that express all or portions of the splice variant. Recombinant cells expressing the truncated BCR-ABL protein with an active kinase domain are useful for identifying drug candidates for treating CML. Methods for predicting likelihood for responsiveness to kinase inhibitor therapy are included along with methods, compositions and reagents for detecting the splice variant. Methods of treating patients at increased risk of having or developing drug resistance by administering combinations of drugs are also included.

Variants of the Bcr-Abl mRNA

Several variants of bcr-abl mRNA have been reported. Many of the known sequences are full length cDNA sequences and some are partial cDNA sequences. Exemplary bcr-abl mRNA sequences include but are not limited to: NCBI GenBank accession numbers: EU216072, EU216071, EU216070, EU216069, EU216068, EU216067, EU216066, EU216065, EU216064, EU216063, EU216062, EU216061, EU216060, EU216059, EU216058, EU236680, DQ912590, DQ912589, DQ912588, DQ898315, DQ898314, DQ898313, EF423615, EF158045, 572479, 572478, AY789120, AB069693, AF487522, AF113911, AF251769, M30829, M30832, M17542, M15025, and M17541. An exemplary cDNA sequence of bcr-abl is listed as SEQ ID NO: 19 and shown in FIGS. 16A-16B.

bcr-abl splice variants: Alternative splicing may result in bcr-abl mRNA variants. In some embodiments, CML patients undergoing BCR-ABL tyrosine kinase inhibitor therapy (for example, imatinib), may exhibit an insertion of 35 nucleotides from abl intron 8 at the junction of abl exons 8 and 9 of the bcr-abl mRNA due to alternate splicing. Exemplary cDNA sequence of alternately spliced bcr-abl mRNA is listed as SEQ ID NO: 26 and shown in FIGS. 17A-17C.

In preferred embodiments, the 35 base insert of abl intron 8 (nucleotides positions 132744926 to 132744960 of GenBank accession number NC 00009) is SEQ ID NO: 4.

```
                                            (SEQ ID NO: 4)
5'-actttgataaccgtgaagaaagaacaagatagaag-3'
```

In preferred embodiments, insertion of 35 bp sequence of abl intron 8 (SEQ ID NO: 4) at the junction of abl exons 8 and 9 due to alternate splicing will create a new splice variant of bcr-abl mRNA comprising a sequence of SEQ ID NO: 1.

```
                                            (SEQ ID NO: 1)
5'-catttggagtattgattgggaaattgctacctatggcatgtcccctt acccgggaattgacctgtcccaggtgtatgagctgctagagaaggactac cgcatggagcgcccagaaggctgcccagagaaggtctatgaactcatgcg agcatactttgataaccgtgaagaaagaacaagatagaaggttggcagtg gaatccctctgaccggccctcctttgctgaaatccaccaagcctttgaaa caatgttccaggaatccagtatctcagacg-3'
```

Exemplary nucleic acid sequence of abl exons 8 and 9 and abl intron 8 can be found in GenBank accession number NC_00009 between nucleic acid positions 132743623 and 132745365. FIG. 1 shows an exemplary abl exons 8 and 9 and intron 8. The 35 base pair insertion sequence of abl intron 8 is indicated with highlighting.

Exemplary abl intron 8 sequence is listed in nucleotides 148-1,647 of SEQ ID NO: 3 and shown in FIG. 13.

FIG. 2 shows a portion of exemplary bcr-abl mRNA splice variant. Nucleic acid sequences of abl exon 8, 35 base insert sequence and abl exon 9 are indicated.

In preferred embodiments, bcr-abl splice variant mRNA can be detected by detecting SEQ ID NO: 1 or portions and complements thereof. In preferred embodiments, bcr-abl splice variant mRNA can be detected by detecting SEQ ID NO: 4 or complements thereof.

In other embodiments, bcr-abl splice variant mRNA resulting from alternate splicing can be detected by detecting the sequences encompassing the junction of 35 bp abl 8 insert and abl exons 8. In preferred embodiments, bcr-abl splice variant mRNA can be detected by detecting SEQ ID NO: 15 or a complement thereof. In preferred embodiments, bcr-abl splice variant mRNA can be detected by detecting a polynucleotide comprising SEQ ID NO: 16 or a complement thereof. In other embodiments, bcr-abl splice variant mRNA can be detected by detecting at least 25 nucleotides comprising SEQ ID NO: 16 or a complement thereof. In some embodiments, bcr-abl splice variant mRNA can be detected by detecting at least 1000 nucleotides comprising SEQ ID NO: 16 or a complement thereof. In some embodiments, bcr-abl splice variant mRNA can be detected by detecting 15 or fewer nucleotide sequences comprising SEQ ID NO: 13. Sequences of SEQ ID NO: 13, SEQ ID NO: 15 and SEQ ID NO: 16 are shown below.

```
                                            (SEQ ID NO: 13)
            5'-gagcatactttg-3'

(SEQ ID NO: 15)
            5'-aactcatgcgagcatactttgataaccgtg-3'

(SEQ ID NO: 16)
            5'-atgcgagcatactttgataa-3'
```

In preferred embodiments, bcr-abl splice variant mRNA resulting from alternate splicing can be detected by detecting the sequences encompassing the junction of 35 bp insert of abl intron 8 (SEQ ID NO: 4) and abl exon 9. In preferred embodiments, bcr-abl splice variant mRNA can be detected by detecting SEQ ID NO: 17 or a complement thereof. In preferred embodiments, bcr-abl splice variant mRNA can be detected by detecting a polynucleotide comprising SEQ ID NO: 18 or a complement thereof. In other embodiments, bcr-abl splice variant mRNA can be detected by detecting at least 25 nucleotides comprising SEQ ID NO: 18 or a complement thereof. In some embodiments, bcr-abl splice variant mRNA can be detected by detecting at least 1000 nucleotides comprising SEQ ID NO: 18 or a complement thereof. In some embodiments, bcr-abl splice variant mRNA can be detected by detecting 15 or fewer nucleotide sequences comprising SEQ ID NO: 14. Sequences of SEQ ID NO: 14, SEQ ID NO: 17 and SEQ ID NO: 18 are shown below:

```
                                        (SEQ ID NO: 14)
5'-tagaaggttggc-3'

(SEQ ID NO: 17)
5'-agaacaagatagaaggttggcagtggaatc-3'

(SEQ ID NO: 18)
5'-gaaggttggcagtggaatcc-3'
```

In preferred embodiments, bcr-abl splice variant mRNA can be detected by detecting at least 100 contiguous nucleotides of SEQ ID NO: 1 or a complement thereof, and SEQ ID NO 13 or SEQ ID NO: 14 or both.

In preferred embodiments, bcr-abl splice variant mRNA can be detected by detecting at least 40 contiguous nucleotides of SEQ ID NO: 9.

Sequence of SEQ ID NO: 9 is shown below:

```
                                        (SEQ ID NO: 9)
5'-gagcatactttgataaccgtgaagaaagaacaagatagaaggttgg
c-3'
```

Splice variant of any of the known bcr-abl mRNA sequences listed above and also of any unknown bcr-abl mRNA sequence that comprises at least 40 contiguous nucleotides of SEQ ID NO: 9 that results from alternate splicing producing a bcr-abl mRNA variant may be detected using the methods herein. The resulting bcr-abl mRNA after such alternative splicing may comprise a nucleic acid sequence preferably at least 90% identical to, more preferably at least 95% identical to, and most preferably identical to the entire length of the sequence of SEQ ID NO: 1 or a complement thereof.

Although a sequence of the nucleic acids of SEQ ID NO: 1, 3, 4-9, and 13-18 are shown in the form of DNA, a person of ordinary skill in the art recognizes that the corresponding RNA sequence will have a similar sequence with the thymine being replaced by uracil i.e. "t" with "u".

Variants of BCR-ABL Protein

Several variation of BCR-ABL protein sequence is known in the art. Some of the amino acid sequences are for full length protein and some are amino acid sequences for a fragment of BCR-ABL protein. Exemplary BCR-ABL protein sequence include but not limited to the NCBI protein database accession numbers: ABX82708, ABX82702, AAA35594, ACA62749, ABX82713, CAM33013, CAA10377, CAA10376, AAL99544, AAA88013, CAM33009, ABX82714, ABX82712, ABX82711, ABX82710, ABX82709, ABX82707, ABX82706, ABX82705, ABX82704, ABX82703, ABX82701, ABX82700, ABZ01959, ABW90981, AAL05889, AAA87612, CAM33011, CAP08044, ABM21758, AAD04633, AAF89176, ABZ01958, AB009836, ABZ01957, ABK56838, ABK56837, ABK56836, ABK19807, ABK19806, ABK19805, AAA35596, AAF61858, AAA35595, AAA35592.

Exemplary amino acid sequence of full length BCR-ABL protein without the insertion/truncation mutation is listed in SEQ ID NO: 11 and shown in FIG. 11.

Insertion/truncation mutant of BCR-ABL protein: In some embodiments, CML patients undergoing BCR-ABL tyrosine kinase inhibitor therapy (for example, imatinib), may have a bcr-abl splice variant mRNA due to the insertion of 35 nucleotides from abl intron 8 at the junction of abl exons 8 and 9 of the bcr-abl mRNA due to alternate splicing. In preferred embodiments, the sequence of the 35 base insert may be SEQ ID NO: 4. The insertion of SEQ ID NO: 4 at the abl exon 8/9 junction creates a premature stop codon at nucleotide 30 of the abl intron 8 derived sequence resulting in a new c-terminal region for the BCR-ABL protein with the insertion of 10 new amino acids derived from the abl intron sequence and truncation of 653 c-terminal amino acids. The truncated 653 amino acids include a part of the kinase domain and the amino acids encoded by the entire last exon. Exemplary amino acid sequence of the insertion/truncation mutant of BCR-ABL protein is listed as SEQ ID NO: 20 and shown in FIG. 12.

In preferred embodiments, the amino acid sequence of the c-terminal region of the BCR-ABL protein encoded by the bcr-abl splice variant mRNA may comprise a sequence shown in SEQ ID NO: 2.

Sequence of SEQ ID NO: 2 is shown below:

```
                                        (SEQ ID NO: 2)
MSPYPGIDLSQVYELLEKDYRMERPEGCPEKVYELMRAYFDNREERTR
```

Amino acid sequence of the 10 new amino acids derived from abl intron 8 and inserted at the c-terminal region of the BCR-ABL protein encoded by the bcr-abl splice variant mRNA is shown as SEQ ID NO: 10.

Sequence of SEQ ID NO: 10 is shown below:

```
                                        (SEQ ID NO: 10)
YFDNREERTR
```

In preferred embodiments, c-terminal region of the BCR-ABL protein encoded by the bcr-abl splice variant mRNA may comprise a sequence of at least 15 contiguous amino acids of SEQ ID NO: 2 from amino acid positions 34 to 48 and represented as SEQ ID NO: 12.

Sequence of SEQ ID NO: 12 is shown below:

```
                                        (SEQ ID NO: 12)
ELMRAYFDNREERTR
```

The insertion/truncation mutant of BCR-ABL protein of any of the known BCR-ABL protein sequence listed above and also of any unknown BCR-ABL protein sequence resulting from alternate splicing comprising a c-terminal region amino acid sequence of SEQ ID NO: 12 may be detected herein. In some embodiments, the resulting insertion/truncation mutant of BCR-ABL protein will have an amino acid sequence of the c-terminal region preferably at least 90% identical to, more preferably at least 95% identical to, and most preferably identical to the entire length of the amino acid sequence of SEQ ID NO: 2.

Mutations in the ABL kinase domain: CML patients undergoing tyrosine kinase inhibitor therapy (such as, imatinib, nilotinib, dasatinib, Bosutinib (SKI-606) and Aurora kinase inhibitor VX-680) may develop resistance to such inhibitors. Several underlying mechanisms of resistance to kinase inhibitors have been identified. One major cause is the presence of point mutations within the ABL kinase domain of BCR-ABL. In one embodiment, such mutations inhibit the ability of imatinib to bind to BCR-ABL by altering the binding sites or preventing the kinase domain from assuming the inactive conformation required for imatinib binding (O'Hare et al. Blood. 2007; 110: 2242-2249). Point mutations develop in approximately 35% to 70% of patients displaying resistance to imatinib, either spontaneously or through the evolutionary pressure of imatinib (Branford et al. Blood. 2003; 102: 276-283).

More than 40 distinct resistance-conferring mutations have been detected; the majority fall within four regions of the kinase domain: the ATP-binding loop (P-loop) of the ABL kinase domain, the contact site, the SHY binding site (activation loop), and the catalytic domain (Hughes et al. Blood. 2006; 108: 28-37). A list of such mutations are shown in FIG. 6 and incorporated herein by reference. Approximately 85% of all imatinib-resistant mutations are associated with amino acid substitutions at just seven residues (P-loop: M244V, G250E, Y253F/H and E255K/V; contact site: T315I; and catalytic domain: M351T and F359V). The most frequently mutated region of BCR-ABL is the P-loop, accounting for 36% to 48% of all mutations.

The importance of P-loop mutations is further underlined by in vitro evidence suggesting that these mutations are more oncogenic with respect to un-mutated BCR-ABL as well as other mutated variants. In various biological assays, P-loop mutants Y253F and E255K exhibited an increased transformation potency relative to un-mutated BCR-ABL. Overall, the relative transformation potencies of various mutations were found to be as follows: Y253F>E255K>native BCR-ABL>T315I>H396P>M351T. Transformation potency also correlated with intrinsic BCR-ABL kinase activity in this study.

In some embodiments, CML patients undergoing kinase inhibitor therapy may develop two kinds of mutations: a) an insertion/truncation mutant of BCR-ABL due to alternate splicing and b) one or more point mutations in the kinase domain of ABL. The association of these mutations in CML patients resistant to imatinib are shown in Table 1.

In preferred embodiments, the alternate splice variant of bcr-abl mRNA can be detected simultaneously with the detection of mutations in abl portion of bcr-abl mRNA. In another embodiment, the mutations in the abl portion of bcr-abl mRNA can be detected separately. Several methods are known in the art for detection of the presence or absence of such mutations. Non limiting examples include, DNA sequencing, detection by hybridization of a detectably labeled probe, detection by size, allele specific PCR, ligation amplification reaction (LAR), detection by oligonucleotide arrays.

Insertion/Truncation Mutant of Abl Protein

In some embodiments, transcripts abl gene may exhibit alternate splicing. The alternate splicing may result in the insertion of 35 nucleotides from abl intron 8 at the junction of abl exons 8 and 9 of the bcr-abl mRNA. Insertion of the 35 nucleotides of abl intron 8 at the junction of abl exons 8 and 9 may result in the generation of ten new codons and also a stop codon resulting in an insertion/truncation mutant. Exemplary nucleic acid sequence of abl intron 8 is listed as nucleotides 148-1,647 of SEQ ID NO: 3 and shown in FIG. 13. In the insertion/truncation mutant protein, a portion of the c-terminus of the Abl protein will be truncated and 10 new amino acids will be added to the c-terminus. Exemplary amino acid sequence of wild-type Abl protein is listed as SEQ ID NO: 24 and shown in FIG. 14. Exemplary amino acid sequence of the insertion/truncation mutant protein is listed as SEQ ID NO: 25 and shown in FIG. 15.

In preferred embodiments, bcr-abl splice variant mRNA resulting from alternate splicing can be detected simultaneously with the splice variant of abl mRNA. In other preferred embodiments, the splice variant of abl mRNA may be detected simultaneously with detection of the presence or absence of other mutations in the abl gene.

In another embodiment, the presence or absence of the insertion/truncation mutant of Abl protein may be detected. In some embodiments, the presence or absence of the insertion/truncation mutant of Abl protein may be detected simultaneously with the detection of the presence or absence of insertion/truncation mutant of BCR-ABL protein. In some other embodiments, the presence or absence of the insertion/truncation mutant of Abl protein may be detected simultaneously with the detection of the presence or absence of other mutation in the Abl protein.

Biological Sample Collection and Preparation

Sample: Sample may contain polynucleotide or polypeptide. Sample may be of biological and non-biological origin. The sample may be of human or non-human origin. The sample may be obtained from eukaryotic or prokaryotic organisms, or environment. The sample may be solid, liquid, and semisolid, with or without any cell or tissue. The sample may include, but are not limited to, amniotic fluid, biopsies, blood, blood cells, bone marrow, cerebrospinal fluid, fecal samples, excrements, fine needle biopsy samples, peritoneal fluid, plasma, serum, pleural fluid, bronchial alveolar lavage, bronchial wash, saliva, semen, serum, sputum, tears, buccal swab, tissue, tissue homogenates, frozen tissue, paraffin sections of tissue, tissue culture media, cells, cell lysates, cell from culture, cell culture supernatant, fetus, embryo, urine, microbes, virus, mycoplasma.

In one embodiment, the sample may be obtained from an individual who is suspected of having a disease, or a genetic abnormality. In another embodiment sample may be obtained from a healthy individual who is assumed of having no disease, or a genetic abnormality. In preferred embodiments, the sample may be obtained from CML patients undergoing kinase inhibitor therapy. In another embodiment, sample may be obtained from CML patients not undergoing kinase inhibitor therapy.

Sample Collection: Methods of obtaining samples are well known to those of skill in the art and include, but are not limited to, aspirations, tissue sections, drawing of blood or other fluids, surgical or needle biopsies, collection of paraffin embedded tissue, collection of body fluids, collection of stool, urine, buccal swab and the like.

Sample Preparation: The nucleic acid (DNA or RNA) or polypeptide may be isolated from the sample according to any methods well known to those of skill in the art. If necessary, the sample may be collected or concentrated by centrifugation and the like. The sample may be subjected to lysis, such as by treatments with enzymes, heat, surfactants, ultrasonication, or a combination thereof. The lysis treatment is performed in order to obtain a sufficient amount of nucleic acid or polypeptide. The sample may be subjected to liquid chromatography to partially purify the nucleic acid or polypeptide. In some embodiments, the whole cell lysates or tissue homogenate may used as source of nucleic acid or polypeptide without further isolation and purification.

Suitable DNA isolation methods include phenol and chloroform extraction, see Sambrook, et al., Molecular Cloning: A Laboratory Manual (1989), Second Edition, Cold Spring Harbor Press, Plainview, NY.

Numerous commercial kits also yield suitable DNA including, but not limited to, QIAamp™ mini blood kit, Agencourt Genfind™, Roche Cobas® Roche MagNA Pure® or phenol: chloroform extraction using Eppendorf Phase Lock Gels®. Total DNA (e.g., genomic, mitochondrial, microbial, viral,) can be purified from any biological sample such as whole blood, plasma, serum, buffy coat, bone marrow, other body fluids, lymphocytes, cultured cells, tissue, and forensic specimens using commercially available kits e.g., QIAamp DNA and QIAamp DNA Blood mini kits from Qiagen. Viral RNA can be purified from whole blood, plasma, serum, buffy coat, bone marrow, other body fluids, lymphocytes, cultured cells, tissue, and forensic specimens using commercially available kits e.g., QIAamp Viral RNA mini kit.

In another embodiment, nucleic acid may be mRNA or cDNA generated from mRNA or total RNA may be used. RNA is isolated from cells or tissue samples using standard techniques, see, e.g., Sambrook, et al., Molecular Cloning: A Laboratory Manual, Second Edition (1989), Cold Spring Harbor Press, Plainview, NY. In addition, reagents and kits for isolating RNA from any biological sample such as whole blood, plasma, serum, buffy coat, bone marrow, other body fluids, lymphocytes, cultured cells, tissue, and forensic specimens are commercially available e.g., RNeasy Protect Mini kit, RNeasy Protect Cell Mini kit, QIAamp RNA Blood Mini kit, RNeasy Protect Saliva Mini kit, Paxgene Blood RNA kit from Qiagen; MELT™, RNaqueous®, ToTALLY RNA™, RiboPure™-Blood, Poly(A)Purist™ from Applied Biosystems; TRIZOL® reagent, Dynabeads® mRNA direct kit from Invitrogen.

In one embodiment, the nucleic acid is isolated from paraffin embedded tissue. Methods of extracting nucleic acid from paraffin embedded tissue are well known in the art e.g., paraffin blocks containing the tissue are collected, de-waxed by treatment with xylene, treated with proteinase to remove protein contaminants, and then finally extracted with phenol and chloroform, followed by ethanol precipitation. Alternatively, nucleic acid from a paraffin embedded tissue can be isolated by commercially available kits e.g., EZ1 DNA kit, QIAamp DNA Mini Kit from Qiagen; Paraffin Block RNA Isolation Kit, RecoverAll™ Total Nucleic Acid Isolation Kit from Ambion.

Nucleic acid need not be extracted, but may be made available by suitable treatment of cells or tissue such as described in U.S. patent application Ser. No. 11/566,169.

Nucleic Acid Amplification

Nucleic acid extracted can be amplified using nucleic acid amplification techniques well know in the art. Nucleic acid amplification can be linear or exponential. Many of these amplification methods can also be used to detect the presence of mutations simply by designing oligonucleotide primers or probes to interact with or hybridize to a particular target sequence in a specific manner. By way of example, but not by way of limitation these techniques can include the polymerase chain reaction (PCR) reverse transcriptase polymerase chain reaction (RT-PCR), nested PCR, ligase chain reaction. See Abravaya, K., et al., Nucleic Acids Res. (1995), 23:675-682, branched DNA signal amplification; Urdea, M. S., et al., AIDS (1993), 7(suppl 2):S11-S14; amplifiable RNA reporters, Q-beta replication, transcription-based amplification, boomerang DNA amplification, strand displacement activation, cycling probe technology, isothermal nucleic acid sequence based amplification (NASBA). See Kievits, T. et al., J Virological Methods (1991), 35:273-286, Invader Technology, or other sequence replication assays or signal amplification assays.

Primers

Oligonucleotide primers for use in these methods can be designed according to general guidance well known in the art as described herein, as well as with specific requirements as described herein for each step of the particular methods described.

In some embodiments, oligonucleotide primers for cDNA synthesis and PCR are 10 to 100 nucleotides in length, preferably between about 15 and about 60 nucleotides in length, more preferably 25 and about 50 nucleotides in length, and most preferably between about 25 and about 40 nucleotides in length. There is no standard length for optimal hybridization or polymerase chain reaction amplification.

Methods of designing primers have been described in U.S. patent application Ser. No. 10/921,482. Primers useful in the methods described herein are also designed to have a particular melting temperature ($T_m$) by the method of melting temperature estimation. Commercial programs, including Oligo™, Primer Design and programs available on the internet, including Primer3 and Oligo Calculator can be used to calculate a $T_m$ of a polynucleotide sequence useful according to the invention.

$T_m$ of a polynucleotide affects its hybridization to another polynucleotide (e.g., the annealing of an oligonucleotide primer to a template polynucleotide). In the subject methods, it is preferred that the oligonucleotide primer used in various steps selectively hybridizes to a target template or polynucleotides derived from the target template (i.e., first and second strand cDNAs and amplified products). Typically, selective hybridization occurs when two polynucleotide sequences are substantially complementary (at least about 65% complementary over a stretch of at least 14 to 25 nucleotides, preferably at least about 75%, more preferably at least about 90% complementary). See Kanehisa, M., Polynucleotides Res. (1984), 12:203, incorporated herein by reference. As a result, it is expected that a certain degree of mismatch at the priming site is tolerated. Such mismatch may be small, such as a mono-, di- or tri-nucleotide. In preferred embodiments, 100% complementarity is preferred.

Probes

Probes are capable of hybridizing to at least a portion of the nucleic acid of interest or a reference nucleic acid. Probes may be an oligonucleotide, artificial chromosome, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may be used for detecting and/or capturing nucleic acid of interest.

Typically, probes can be about 10 bases, about 20 bases, about 25 bases, about 30 bases, about 35 bases, about 40 bases, about 50 bases, about 60 bases, about 75 bases, about 100 bases long.

However, longer probes are possible. Longer probes can be about 200 bases, about 300 bases, about 400 bases, about 500 bases, about 750 bases, about 1,000 bases, about 1,500 bases, about 2,000 bases, about 2,500 bases, about 3,000 bases, about 3,500 bases, about 4,000 bases, about 5,000 bases, about 7,500 bases, about 10,000 bases long.

In some embodiments in all aspects of this invention, probes consist of a detectable label or a plurality of detectable labels. In one preferred embodiment, the detectable label associated with the probe can generate a detectable signal directly. In another embodiment, the detectable label associated with the probe can be detected indirectly using a reagent, wherein the reagent includes a detectable label, and binds to the label associated with the probe. In one embodiment the reagent including a detectable label is a labeled antibody. In another embodiment the reagent including a detectable label is a primary antibody/secondary antibody pair, wherein the detectable label may be in the primary antibody, or in the secondary antibody or in both.

Detectable Label

The term "detectable label" as used herein refers to a molecule or a compound or a group of molecules or a group of compounds associated with an oligonucleotide (e.g., a probe or primer) and is used to identify the probe hybridized to a genomic nucleic acid or reference nucleic acid.

Detectable labels include but are not limited to fluorophores, isotopes (e.g., $^{32}P$, 33P, $^{35}S$, $^{3}H$, $^{14}C$, $^{125}I$, $^{131}I$), electron-dense reagents (e.g., gold, silver), nanoparticles, enzymes commonly used in an ELISA (e.g., horseradish peroxidase, beta-galactosidase, luciferase, alkaline phosphatase), chemiluminescent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

One general method for real time PCR uses fluorescent probes such as the TaqMan® probes, molecular beacons, and Scorpions. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

TaqMan® probes (Heid, et al., Genome Res 6: 986-994, 1996) use the fluorogenic 5'exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi, et al., 16 Nature Biotechnology 49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

In a preferred embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes.

Suitable fluorescent moieties include but are not limited to the following fluorophores working individually or in combination: 4-acetamido-4'-isothiocyanatostilbene-2,2'disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rhodamine isothiocyanate (TRITC).

Detection of Nucleic Acid by Size

Methods for detecting the presence or amount of polynucleotides are well known in the art and any of them can be used in the methods described herein so long as they are capable of separating individual polynucleotides by the difference in size of the amplicons. The separation technique used should permit resolution of nucleic acid as long as they differ from one another by at least one nucleotide. The separation can be performed under denaturing or under non-denaturing or native conditions—i.e., separation can be performed on single- or double-stranded nucleic acids. It is preferred that the separation and detection permits detection of length differences as small as one nucleotide. It is further preferred that the separation and detection can be done in a high-throughput format that permits real time or contemporaneous determination of amplicon abundance in a plurality of reaction aliquots taken during the cycling reaction. Useful methods for the separation and analysis of the amplified products include, but are not limited to, electrophoresis (e.g., agarose gel electrophoresis, capillary electrophoresis (CE)), chromatography (HPLC), and mass spectrometry.

In one embodiment, CE is a preferred separation means because it provides exceptional separation of the polynucleotides in the range of at least 10-1,000 base pairs with a resolution of a single base pair. CE can be performed by methods well known in the art, for example, as disclosed in U.S. Pat. Nos. 6,217,731; 6,001,230; and 5,963,456, which are incorporated herein by reference. High-throughput CE apparatuses are available commercially, for example, the HTS9610 High throughput analysis system and SCE 9610 fully automated 96-capillary electrophoresis genetic analysis system from Spectrumedix Corporation (State College, Pa.); P/ACE 5000 series and CEQ series from Beckman Instruments Inc (Fullerton, Calif.); and ABI PRISM 3100 genetic analyzer (Applied Biosystems, Foster City, Calif.). Near the end of the CE column, in these devices the amplified DNA fragments pass a fluorescent detector which measures signals of fluorescent labels. These apparatuses provide automated high throughput for the detection of fluorescence-labeled PCR products.

The employment of CE in the methods described herein permits higher productivity compared to conventional slab gel electrophoresis. By using a capillary gel, the separation speed is increased about 10 fold over conventional slab-gel systems.

With CE, one can also analyze multiple samples at the same time, which is essential for high-throughput. This is achieved, for example, by employing multi-capillary systems. In some instances, the detection of fluorescence from DNA bases may be complicated by the scattering of light from the porous matrix and capillary walls. However, a confocal fluorescence scanner can be used to avoid problems due to light scattering (Quesada et al., Biotechniques (1991), 10:616-25).

In some embodiments, nucleic acid may be analyzed and detected by size using agarose gel electrophoresis. Methods of performing agarose gel electrophoresis are well known in the art. See Sambrook et al., Molecular Cloning: A Laboratory Manual (2nd Ed.) (1989), Cold Spring Harbor Press, N.Y.

DNA Sequencing

In some embodiments, detection of nucleic acid is by DNA sequencing. Sequencing may be carried out by the dideoxy chain termination method of Sanger et al. (Proceedings of the National Academy of Sciences USA (1977), 74, 5463-5467) with modifications by Zimmermann et al. (Nucleic Acids Res. (1990), 18:1067). Sequencing by dideoxy chain termination method can be performed using Thermo Sequenase (Amersham Pharmacia, Piscataway, NJ), Sequenase reagents from US Biochemicals or Sequatherm sequencing kit (Epicenter Technologies, Madison, Wis.). Sequencing may also be carried out by the "RR dRhodamine Terminator Cycle Sequencing Kit" from PE Applied Biosystems (product no. 403044, Weiterstadt, Germany), Taq DyeDeoxy™ Terminator Cycle Sequencing kit and method (Perkin-Elmer/Applied Biosystems) in two directions using an Applied Biosystems Model 373A DNA or in the presence of dye terminators CEQ™ Dye Terminator Cycle Sequencing Kit, (Beckman 608000). Alternatively, sequencing can be performed by a method known as Pyrosequencing (Pyrosequencing, Westborough, Mass.). Detailed protocols for Pyrosequencing can be found in: Alderborn et al., Genome Res. (2000), 10:1249-1265.

Genetically Modifying Host Cells by Introducing Recombinant Nucleic Acid

The recombinant nucleic acid (e.g., cDNA or genomic DNA) encoding at least a portion of bcr-abl or its variants may be introduced into host cells thereby genetically modifying the host cell. Host cells may be used for cloning and/or for expression of the recombinant nucleic acid. Host cells can be prokaryotic, for example bacteria. Host cell can be also be eukaryotic which includes but not limited to yeast, fungal cell, insect cell, plant cell and animal cell. In preferred embodiment, the host cell can be a mammalian cell. In another preferred embodiment host cell can be human cell. In one preferred embodiment, the eukaryotic host cell may be K562 cell. K562 cells were the first human immortalized myelogenous leukemia line to be established and are a bcr-abl positive erythroleukemia line derived from a CML patient in blast crisis (Lozzio & Lozzio, Blood. 1975; 45(3): 321-334; Drexler, H. G. The Leukemia-Lymphoma Cell Line Factsbook. (2000), Academic Press.

Host cells may comprise wild-type genetic information. The genetic information of the host cells may be altered on purpose to allow it to be a permissive host for the recombinant DNA. Examples of such alterations include mutations, partial or total deletion of certain genes, or introduction of non-host nucleic acid into host cell. Host cells may also comprise mutations which are not introduced on purpose.

Several methods are known in the art to introduce recombinant DNA in bacterial cells that include but are not limited to transformation, transduction, and electroporation, see Sambrook, et al., Molecular Cloning: A Laboratory Manual (1989), Second Edition, Cold Spring Harbor Press, Plainview, NY. Non limiting examples of commercial kits and bacterial host cells for transformation include NovaBlue Singles™ (EMD Chemicals Inc, NJ, USA), Max Efficiency® DH5α™, One Shot® BL21 (DE3) *E. coli* cells, One Shot® BL21 (DE3) pLys *E. coli* cells (Invitrogen Corp., Carlsbad, CA, USA), XL1-Blue competent cells (Stratagene, CA, USA). Non limiting examples of commercial kits and bacterial host cells for electroporation include Zappers™ electrocompetent cells (EMD Chemicals Inc, NJ, USA), XL1-Blue Electroporation-competent cells (Stratagene, CA, USA), ElectroMAX™ A. tumefaciens LBA4404 Cells (Invitrogen Corp., Carlsbad, CA, USA).

Several methods are known in the art to introduce recombinant nucleic acid in eukaryotic cells. Exemplary methods include transfection, electroporation, liposome mediated delivery of nucleic acid, microinjection into to the host cell, see Sambrook, et al., Molecular Cloning: A Laboratory Manual (1989), Second Edition, Cold Spring Harbor Press, Plainview, NY. Non limiting examples of commercial kits and reagents for transfection of recombinant nucleic acid to eukaryotic cell include Lipofectamine™ 2000, Optifect™ Reagent, Calcium Phosphate Transfection Kit (Invitrogen Corp., Carlsbad, CA, USA), GeneJammer® Transfection Reagent, LipoTAXI® Trasfection Reagent (Stratagene, CA, USA). Alternatively, recombinant nucleic acid may be introduced into insect cells (e.g. sf9, sf21, High Five™) by using baculo viral vectors.

In one preferred embodiment, an exemplary vector comprising the cDNA sequence of bcr-abl splice variant (pCMV/GFP/35INS bcr-abl, shown in FIG. 5B) may be transfected into K562 cells. Stable transfected K 562 cells may be developed by transfecting the cells with varying amounts of the pCMV/GFP/35INS bcr-abl vector (0 ng-500 ng) using various methods known in the art. In one exemplary method, The ProFection® Mammalian Transfection System—Calcium Phosphate (Promega Corporation, WI, USA) may be used. This is a simple system containing two buffers: CaCl2 and HEPES-buffered saline. A precipitate containing calcium phosphate and DNA is formed by slowly mixing a HEPES-buffered phosphate solution with a solution containing calcium chloride and DNA. These DNA precipitates are then distributed onto eukaryotic cells and enter the cells through an endocytic-type mechanism. This transfection method has been successfully used by others (Hay et al. J. Biol. Chem. 2004; 279: 1650-58). The transfected K562 cells can be selected from the non-transfected cells by using the antibiotics Neomycin and Ampicillin. Expression of the spliced variant of bcr-abl can assessed from the co-expression of the reporter gene GFP.

Alternatively, in a 24-well format complexes are prepared using a DNA (μg) to Lipofectamine™ 2000 (Invitrogen Corporation, Carlsbad, CA, USA) (μl) ratio of 1:2 to 1:3. Cells are transfected at high cell density for high efficiency, high expression levels, and to minimize cytotoxicity. Prior to preparing complexes, 4-8×10$^5$ cells are plated in 500 μl of growth medium without antibiotics. For each transfection sample, complexes are prepared as follows: a. DNA is diluted in 50 μl of Opti-MEM® I Reduced Serum Medium without serum (Invitrogen Corporation, Carlsbad, CA, USA) or other medium without serum and mixed gently. b. Lipofectamine™ 2000 is mixed gently before use and the mixture is diluted to appropriate amount in 50 μl of Opti-MEM® I Medium. The mixture is incubated for 5 minutes at room temperature. c. After 5 minute incubation, the diluted DNA is combined with diluted Lipofectamine™ 2000 (total volume=100 μl) and is mixed gently. The mixture is incubated for 20 minutes at room temperature. 100 μl of complexes is added to each well containing cells and medium. The contents are mixed gently by rocking the plate back and forth. Cells are incubated at 37° C. in a CO2 incubator for 18-48 hours prior to testing for transgene expression. Medium may be changed after 4-6 hours. Cells are passaged at a 1:10 (or higher dilution) into fresh growth medium 24 hours after transfection. Selective medium (containing Neomycin and Ampicillin) is added the following day.

Antibody Production and Screening

Various procedures known in the art may be used for the production of antibodies to epitopes of the BCR-ABL protein and the insertion truncation mutant of BCR-ABL protein. Such antibodies include but are not limited to polyclonal, monoclonal, chimeric, single chain, Fab fragments and fragments produced by a Fab expression library. Antibodies that specifically bind to an epitope of SEQ ID NO: 2 are useful for detection and diagnostic purposes.

In preferred embodiments, the antibodies may bind specifically to an epitope comprising at least 15 contiguous amino acids of SEQ ID NO: 2 from amino acid positions 34 to 48 and represented as SEQ ID NO: 12. In another embodiment, antibodies may specifically bind to an epitope comprising the amino acid sequences of SEQ ID NO: 10. Antibodies specifically binding to an epitope comprising SEQ ID NO: 12 or SEQ ID NO: 10 will specifically detect and distinguish insertion truncation mutant of BCR-ABL protein from other BCR-ABL proteins without such insertion/truncation mutation. Antibodies specifically binding to an epitope comprising SEQ ID NO: 12 or SEQ ID NO: 10 may be monoclonal or polyclonal. Such antibodies are useful for detection and diagnostic purposes.

Monoclonal antibodies that bind BCR-ABL protein and the insertion truncation mutant of BCR-ABL protein may be radioactively labeled allowing one to follow their location and distribution in the body after injection. Radioactivity tagged antibodies may be used as a non-invasive diagnostic tool for imaging de novo cells of tumors and metastases.

Immunotoxins may also be designed which target cytotoxic agents to specific sites in the body. For example, high affinity BCR-ABL protein and insertion truncation mutant of BCR-ABL protein specific monoclonal antibodies may be covalently complexed to bacterial or plant toxins, such as diphtheria toxin, abrin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate BCR-ABL protein and insertion truncation mutant of BCR-ABL protein expressing cells.

For the production of antibodies, various host animals may be immunized by injection with the full length or fragment of BCR-ABL protein and the insertion truncation mutant of BCR-ABL protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to BCR-ABL protein and the insertion truncation mutant of BCR-ABL protein may be prepared by using any technique which provides for the production of antibody molecules by continuous cell lines in culture. These include but are not limited to the hybridoma technique originally described by Kohler and Milstein, (Nature (1975), 256:495-497), the human B-cell hybridoma technique (Kosbor et al., Immunology Today (1983), 4:72; Cote et al. Proc. Natl. Acad. Sci. (1983), 80:2026-2030) and the EBV-hybridoma technique (Cole et al., Monoclonal Antibodies and Cancer Therapy (1985), Alan R. Liss, Inc., pp. 77-96). In addition, techniques developed for the production of "chimeric antibodies" (Morrison et al., Proc. Natl. Acad. Sci. USA (1984), 81:6851-6855; Neuberger et al., Nature (1984), 312:604-608; Takeda et al., Nature (1985), 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce BCR-ABL protein and insertion truncation mutant of BCR-ABL protein-specific single chain antibodies.

Antibody fragments which contain specific binding sites of BCR-ABL protein and insertion truncation mutant of BCR-ABL protein may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., Science. 1989; 246: 1275-1281) to allow rapid and easy identification of monoclonal Fab fragments with the desired specificity to BCR-ABL protein and insertion truncation mutant of BCR-ABL protein.

Kits

The present inventions also contemplate diagnostic systems in kit form. A diagnostic system of the present inventions may include a kit which contains, in an amount sufficient for at least one assay, any of the hybridization assay probes, amplification primers, and/or antibodies against BCR-ABL wild type and insertion/truncation mutant in a packaging material. Typically, the kits will also include instructions recorded in a tangible form (e.g., contained on paper or an electronic medium) for using the packaged probes, primers, and/or antibodies in a detection assay for determining the presence or amount of bcr-abl splice variant mRNA or BCR-ABL insertion/truncation mutant protein in a test sample.

The various components of the diagnostic systems may be provided in a variety of forms. For example, the required enzymes, the nucleotide triphosphates, the probes, primers, and/or antibodies may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present inventions may contain a reconstitution reagent for reconstituting the lyophilized reagents of the kit. In preferred kits for amplifying target nucleic acid derived from a CML patients, the enzymes, nucleotide triphosphates and required cofactors for the enzymes are provided as a single lyophilized reagent that, when reconstituted, forms a proper reagent for use in the present amplification methods.

In one embodiment, the kit may comprise at least three lyophilized oligonucleotides: a primer pair to amplify a portion of bcr-abl mRNA comprising exons 8 and 9, and a detectably labeled probe capable of hybridizing to the amplicon generated. In some preferred kits, at least three lyophilized oligonucleotides: the detectably labeled probe, and the primer pair for amplification of at least a portion of bcr-abl mRNA may have sequences of SEQ ID NO: 4, 5, 6 or complements and fragments thereof respectively. In some preferred kits, at least four lyophilized oligonucleotide reagents may be of provided having sequences of SEQ ID NO: 5, 6, 7, and 8 or complements and fragments thereof. In some preferred kits at least five lyophilized oligonucleotide reagents may be of provided having sequences of SEQ ID NO: 4, 5, 6, 7, and 8 or complements and fragments thereof.

Some preferred kits may further comprise to a solid support for anchoring the nucleic acid of interest on the solid support. The target nucleic acid may be anchored to the solid support directly or indirectly through a capture probe anchored to the solid support and capable of hybridizing to the nucleic acid of interest. Examples of such solid support include but are not limited to beads, microparticles (for example, gold and other nano particles), microarray, microwells, multiwell plates. The solid surfaces may comprise a first member of a binding pair and the capture probe or the target nucleic acid may comprise a second member of the binding pair. Binding of the binding pair members will anchor the capture probe or the target nucleic acid to the solid surface. Examples of such binding pairs include but are not limited to biotin/streptavidin, hormone/receptor, ligand/receptor, antigen/antibody.

In other preferred kits, lyophilized antibodies against BCR-ABL wild type and insertion/truncation mutant protein are provided. In some preferred kits a primary/secondary antibody pair may be provided. Some preferred kits may further comprise to a solid support for anchoring the BCR-ABL wild type and insertion/truncation mutant protein. Such anchoring of the BCR-ABL wild type and insertion/truncation mutant protein may be through biotin/streptavidin, antigen/antibody interactions.

Typical packaging materials would include solid matrices such as glass, plastic, paper, foil, micro-particles and the like, capable of holding within fixed limits hybridization assay probes, and/or amplification primers of the present invention. Thus, for example, the packaging materials can include glass vials used to contain sub-milligram (e.g., picogram or nanogram) quantities of a contemplated probe, primer, or antibodies or they can be microtiter plate wells to which probes, primers, or antibodies of the present inventions have been operatively affixed, i.e., linked so as to be capable of participating in an amplification and/or detection method of the present invention.

The instructions will typically indicate the reagents and/or concentrations of reagents and at least one assay method parameter which might be, for example, the relative amounts of reagents to use per amount of sample. In addition, such specifics as maintenance, time periods, temperature, and buffer conditions may also be included.

The diagnostic systems of the present inventions contemplate kits having any of the hybridization assay probes, amplification primers, or antibodies described herein, whether provided individually or in one of the preferred combinations described above, for use in determining the presence or amount of bcr-abl splice variant mRNA or BCR-ABL insertion/truncation mutant protein in a test sample.

Identifying a Compound for Treating CML Patients

In one preferred embodiment, cell lines expressing BCR-ABL (both wild-type and/or mutant) proteins may be utilized to screen compounds for treating CML patients. In preferred embodiments, the compounds may be targeting BCR-ABL protein. In some embodiments, the compounds may be inhibitor of Abl kinase activity. Non-limiting examples of kinase inhibitors include but not limited to imatinib, dasatinib, nilotinib, Bosutinib (SKI-606) and Aurora kinase inhibitor VX-680. In other embodiments, the compounds may not be an inhibitor of Abl kinase activity.

The effect of the compounds on the cells may be assessed. Several parameters may be assessed for identifying the compounds that may be beneficial for treatment of CML patients. Non-limiting examples of the parameters that may be assessed includes cell viability, cell proliferation, apoptosis, kinase activity of BCR-ABL protein, additional mutations in BCR-ABL protein, additional mutation in Abl protein.

In one embodiment, human chronic myeloid leukemia (CML) cell lines expressing BCR-ABL (both wild-type and/or mutant) proteins may be used to study the effect of such compounds on their effect on the cells. Non-limiting examples of human chronic myeloid leukemia (CML) cell lines include BV173, K562, KCL-22, and KYO-1, LAMA84, EM2, EM3, BV173, AR230, and KU812 (Mahon, F. X., Blood. 2000; 96: 1070-1079; Lerma et al. Mol. Cancer Ther. 2007; 6(2): 655-66).

In other embodiments, non-CML cells may be transfected with expression vectors comprising bcr-abl gene or variants of bcr-abl gene including splice variants of bcr-abl gene resulting in genetically modified cells comprising the recombinant polynucleotide. Thus, the transfected cells will be able to express BCR-ABL protein or its variants. The genetically modified cells can be used to screen compounds for treating CML patients.

In yet other embodiments, CML cell lines, for example BV173, K562, KCL-22, and KYO-1, LAMA84, EM2, EM3, BV173, AR230, and KU812 may be transfected with expression vectors comprising splice variants of bcr-abl gene resulting in genetically modified cells comprising the recombinant polynucleotide. The gene product of the splice variants of bcr-abl gene, the insertion/truncation mutant of BCR-ABL may impart partial or total resistance to Abl kinase inhibitors to these genetically modified cells. The genetically modified cells may be used to screen compounds for treating CML. The compounds may be inhibitors of Abl kinase activity or these compounds may have other mechanism of action.

The CML cell lines and the genetically modified cell lines as discussed above may be grown in appropriate growth medium and using appropriate selective antibiotics. Methods for cell culture is well known in the art (Sambrook, et al., Molecular Cloning: A Laboratory Manual (1989), Second Edition, Cold Spring Harbor Press, Plainview, NY). Several growth media for cell culture are commercially available. Non-limiting examples include GIBCO® RPMI Media 1640, Dulbecco's Modified Eagle Medium (DMEM), DMEM: Nutrient Mixture F-12 (DMEM/F12), Minimum Essential Media (Invitrogen Corp., Carlsbad, CA, USA), RF-10 medium. Non-limiting examples of selective antibiotics include ampicillin, neomycin, Geneticin®, Hygromycin B.

In one preferred embodiment, K562 cells (ATCC catalog no: CCL-243) may be genetically modified by transfecting with different amounts of the expression vector pCMV/GFP/35INS bcr-abl. In one embodiment, the amount the expression vector pCMV/GFP/35INS bcr-abl used for transfection can be 0 ng, or can be at least about: 1 ng, 2ng, 5ng, 7.5ng, 10 ng, 12.5 ng, 15 ng, 20 ng, 25 ng, 30 ng, 40 ng, 50 ng, 60 ng, 75 ng, 100 ng, 125 ng, 200 ng, 500 ng, 750 ng, or 1 µg. The transfected cells may be grown in RF-10 medium with neomycin/and or ampicillin.

Assessing the Effect of a Compound for Treatment of CML on Genetically Modified Cells Several parameters may be assessed for identifying the compounds that may be beneficial for treatment of CML patients. Non-limiting examples of the parameters that may be assessed includes cell viability, cell proliferation, apoptosis, kinase activity of BCR-ABL protein, additional mutations in BCR-ABL protein, additional mutation in Abl protein.

Kinase Activity of BCR-ABL

The effect of a compound on the kinase activity of the BCR-ABL is assessed by monitoring tyrosine phosphorylation profile of the cellular proteins. CrlkL is a substrate of BCR-ABL tyrosine kinase (Ren et al. Genes Dev. 1994; 8(7): 783-95). Genetically modified cells comprising recombinant bcr-abl or variant so of bcr-abl including the splice variant are grown in presence of various amounts of a compound for treating CML patients. In a preferred embodiment, the compounds are Abl tyrosine kinase inhibitors. Non-limiting examples of kinase inhibitors include imatinib, nilotinib, dasatinib, Bosutinib (SKI-606) and Aurora kinase inhibitor VX-680. Amount of phosphorylated CrkL protein can be measured by using detectably labeled anti-phospho CrkL antibody. In one embodiment, the detectable label is phycoerythrin. The signal can be detected by Flow cytometer. Alternatively, the signal can be detected by Fluorescent Microtiter plate reader.

Sequencing of the Abl Kinase Domain

To further investigate the reason for some cells that do not overexpress BCR-ABL but that have higher resistance to a compound that target the ATP-binding site of the Abl kinase domain (such as imatinib, nilotinib, dasatinib, and Aurora kinase inhibitor VX-680) than their sensitive counterparts, the entire kinase domain of K562-sensitive and -resistant cells can be sequenced. Sequencing can be performed using ABI prism 377 automated DNA sequencer (PE Applied Biosystems; USA). Sequence analysis can performed using the GCG version 10 software.

Prediction of the Likelihood of Drug Resistance in CML Patients or Subjects Suspected of Having CML Methods of the invention can be used for predicting the likelihood that a CML patient or a subject suspected of having CML with a BCR/Abl translocation will be resistant to treatment with one or more BCR-ABL kinase inhibitors. In an embodiment, a sample from a CML patient or a subject suspected of having CML is assessed for the presence or absence of a polynucleotide sequence comprising at least 40 contiguous nucleotides of SEQ ID NO: 9 or a complement thereof. Methods for detecting the presence or absence of said sequence are provided above. The presence of the polynucleotide sequence or a complement thereof in bcr-abl mRNA indicates that the patient has an increased likelihood of being resistant to treatment with one or more BCR-ABL kinase inhibitors relative to a patient not having the polynucleotide sequence.

In another embodiment, bcr-abl mRNA of a CML patient or a subject suspected of having CML is assessed for the presence or absence of a polynucleotide sequence comprising at least 40 contiguous nucleotides of SEQ ID NO: 9 or a complement thereof; and further assessing for the presence or absence of at least one mutation in the abl portion of the bcr-abl gene. Methods for detecting the presence or absence of a polynucleotide sequence comprising at least 40 contiguous nucleotides of SEQ ID NO: 9 or a complement thereof, are provided above. Methods for detecting at least one mutation in the abl portion of the bcr-abl gene are provided above and generally known in the art. The presence of the polynucleotide sequence or a complement thereof in bcr-abl mRNA and presence of at least one mutation in the abl portion of the bcr-abl gene indicates that the patient has an increased likelihood of being resistant to treatment with one or more BCR-ABL kinase inhibitors relative to a CML patent having the mutation alone.

In another embodiment, a sample from a CML patient or a subject suspected of having CML is assessed for the increased likelihood of drug resistance by measuring the amount of RNA encoding a full length BCR-ABL and the amount of RNA encoding a BCR-ABL insertion/truncation splice variant encoded by at least 40 contiguous nucleotides of SEQ ID NO: 9 or a complement thereof; wherein the likelihood of resistance increases with increasing amounts of BCR-ABL mRNA insertion/truncation splice variant relative to full length BCR-ABL encoding mRNA. The percentage of BCR-ABL that is insertion/truncation variant mRNA can be 5, 10, 20, 30, 40, 50, 60, 70, 80, 90, or 100% of the total BCR-ABL corresponding mRNA.

In another embodiment, a sample from a CML patient or a subject suspected of having CML is assessed for the presence or absence of a polypeptide sequence having an amino acid sequence of SEQ ID NO: 10 or SEQ ID NO: 12 or an epitope thereof. Methods for detecting the absence or presence of such polypeptides are discussed above. The presence of the polypeptide sequence or a epitope thereof indicates that the patient has an increased likelihood of being resistant to treatment with one or more BCR-ABL kinase inhibitors relative to a patient not having the polynucleotide sequence.

In another embodiment, a sample from a CML patient or a subject suspected of having CML is assessed for the increased likelihood of drug resistance by measuring the amount of full length BCR-ABL polypeptide and the amount of BCR-ABL truncation mutant polypeptide; wherein the likelihood of resistance increases with increasing amounts of BCR-ABL truncation mutant polypeptide relative to full length BCR-ABL polypeptide. In another embodiment, a sample from a CML patient or a subject suspected of having CML is assessed for the amount of a polypeptide sequence having an amino acid sequence of SEQ ID NO: 10 or SEQ ID NO: 12 or an epitope thereof and the amount of full length BCR-ABL polypeptide. The percentage of BCR-ABL that is insertion/truncation variant polypeptide, can be 5, 10, 20, 30, 40, 50, 60, 70, 80, 90, or 100% of the total BCR-ABL corresponding polypeptide.

Drug Dosage Adjustment and Combination Drug Therapy

Patients expressing BCR-ABL insertion/truncation splice variant mRNA or polypeptide (i.e., having increased likelihood of resistance) are candidates for treatment using higher doses of BCR-ABL kinase inhibitors, relative to the dosage administered to patients expressing lower amounts (or no) BCR-ABL insertion/truncation splice variant or can be candidates for combination therapy using two or more kinase inhibitors.

In an embodiment, a patient found to have an increased likelihood of resistance by any of the methods disclosed above is administered an increased dosage of BCR-ABL kinase inhibitor. In another embodiment, a patient found to have an increased likelihood of resistance by any of the methods disclosed above is administered a combination of two or more BCR-ABL kinase inhibitors. In another embodiment, one of the kinase inhibitors is not a tyrosine kinase inhibitor. The BCR-ABL kinase inhibitor can be imatinib, nilotinib, dasatinib, Bosutinib (SKI-606) or Aurora kinase inhibitor VX-680. The BCR-ABL kinase inhibitor can be homoharringtonine (HHT) or MK0457. The two or more BCR-ABL kinase inhibitors can act synergistically. At least two of the inhibitors can be imatinib and nilotinib. At least two of the inhibitors can be imatinib and HHT. The patient or subject can be drug resistant or not drug resistant. The patient or subject can be treatment-naïve.

While not wishing to be bound by theory, it is believed that by administering a combination of inhibitors before a CML patient demonstrates drug resistance, drug resistance progression can be delayed or prevented.

The invention will now be described in greater detail by reference to the following non-limiting examples.

Example 1

Sample Collection

Patients: Peripheral blood samples were collected from CML patients with or without imatinib resistance. Some of imatinib resistant patients were also resistant to nilotinib and dasatinib. The diagnosis of CML was established based on the examination of bone marrow morphology, cytogenetic, FISH, and molecular studies. The majority of tested samples were fresh, but a significant number used cells frozen in freezing mix and stored at −70° C.

Peripheral Blood Samples: Venous blood (5-8 ml) was collected from patients diagnosed with CML using BD Vacutainer™ CPT™ tubes (Beckton Dickenson, NJ, USA, Catalog number: 362760) by venous puncture. Peripheral mononuclear cells and platelets were isolated using manufacturer's protocol. Briefly, venous blood collected into the CPT™ tube was mixed with the anticoagulant present in the tube by inversion. The blood sample was centrifuged at 1500-1800 RCF for 20 min at room temperature (18° C.-25° C.). Plasma was removed from the top by aspiration without disturbing the white cell layer containing peripheral mononuclear cells and platelets. The peripheral mononuclear cells and platelets were carefully removed with a Pasteur pipette and collected in a separate tube.

RNA Extraction: Total RNA was isolated from the isolated peripheral mononuclear blood cells and platelets using MagNA Pure Compact RNA Isolation Kit (Roche Applied Sciences, Indianapolis, Indiana, Catalog number: 04802993001). Briefly, the prefilled cartridges provided in the kit were penetrated by the disposable piercing tool. Samples were lysed by incubation in lysis buffer containing chaotropic salt and Proteinase K. RNA was bound to the surfaces of the added Magnetic Glass Particles and DNA was degraded by incubation with DNase. After several washing steps to remove unbound substances, the purified RNA was eluted and transferred to the Elution Tubes. RNA was dissolved in 50 µl of water and was used in subsequent RT/PCR reaction.

cDNA Synthesis: One (1) to five (5) micrograms of RNA in 13 µl of DEPC-treated water was added to a clean microcentrifuge tube. One microliter of either oligo $(dT)_{18}$ (0.5 µg/µl) or random hexamer solution (50 ng/µl) was added and mixed gently. The mixture was heated to 70° C. for 10 min, followed by incubation on ice for one minute. The reaction mixture was centrifuged briefly, followed by the addition of 2 µl of 10× Synthesis buffer (200 mM Tris-HCl, pH 8.4, 500 mM KCl, 25 mM Magnesium chloride, 1 mg/ml of BSA), one µl of 10 mM each of dNTP mix, 2 µl of 0.1 M DTT, one µl of SuperScript II RT (200 U/µl) (Life Technologies, GIBCO BRL, Gaithersburg, MD). After gentle mixing, the reaction mixture was subjected to brief centrifugation, and incubated at room temperature for 10 min. The reaction mixture was further incubated at 42° C. for 50 minutes. The reaction was terminated by incubating at 70° C. for 15 min, and then placing it on ice. The reaction mixture was briefly centrifuged, and 1 µl of RNase H (2 Units) was added followed by incubation at 37° C. for 20 min.

Example 2

Bcr-Abl Mutation Detection and Analysis

Amplification of the kinase domain of bcr-abl gene: The kinase domain of the bcr-abl gene was amplified by polymerase chain reaction (PCR) using the cDNA derived from CML patient's mRNA as template. The abl kinase domain was further amplified by hemi-nested PCR to generate an 863 bp amplicon.

The primers used for the first round of PCR are as follows:

```
BCR-Forward:
                                     (SEQ ID NO: 5)
5'-TGA CCA ACT CGT GTG TGA AAC TC-3'

ABL-R2 Reverse:
                                     (SEQ ID NO: 6)
5'-TCC ACT TCG TCT GAG ATA CTG GAT T-3'
```

The primers for the hemi-nested PCR are as follows:

```
ABL-F1 Forward:
                                     (SEQ ID NO: 7)
5'-CGC AAC AAG CCC ACT GTC T-3'

ABL-R2 Reverse:
                                     (SEQ ID NO: 6)
5'-TCC ACT TCG TCT GAG ATA CTG GAT T-3'
```

The forward primer, BCR-Forward (SEQ ID NO: 5) annealed to bcr exon b2 and the reverse primer having a sequence of ABL-R2 (SEQ ID NO: 6) annealed to the junction of abl exon 9 and 10. This primer pair will not amplify cDNA with the normal abl gene.

To the reaction mixture comprising cDNA (2 µg), 8 µl of 10× synthesis buffer (200 mM Tris-HCl, pH 8.4, 500 mM KCl, 25 mM magnesium chloride, 1 mg/ml of BSA), 68 µl sterile double-distilled water, 1 µl amplification primer SEQ ID NO: 5 (10 µM), 1 µl amplification primer SEQ ID NO: 6 (10 µM), 1 µl Taq DNA polymerase (2-5 U/µl) were added. The reaction mixture was mixed gently and the reaction mixture was overlayed with mineral oil. The reaction mixture was heated to 94° C. for 5 minutes to denature remaining RNA/cDNA hybrids. PCR amplification was then performed in an automated thermal-cycler for 15-50 cycles, at 94° C. for 1 minute, 55° C. for 30 to 90 seconds, and 72° C. for 2 minutes.

The inner forward primer, ABL-F1 Forward (SEQ ID NO: 7) and the same reverse primer ABL-R2 (SEQ ID NO: 6) were both labeled with Cy5®. The reaction mixture (50 µl) comprised a 5 µl of the product from the first PCR, 20 pmol of each primer and was amplified using the PCR reaction conditions as before.

Sequencing of PCR products: The nested (863 bp) PCR product was sequenced with 4 sequencing primers to ensure that the entire Abl kinase domain was 2× covered by dye terminator chemistry and ABI sequencer (Applied Biosystems, Foster City, CA). The 4 sequencing primers used are as follows:

```
ABL-F1 Forward:
                                     (SEQ ID NO: 7)
5'-CGC AAC AAG CCC ACT GTC T-3'

ABL-F2 Forward:
                                     (SEQ ID NO: 8)
5'-TGG TAG GGG AGA ACC ACT TG-3'

ABL-R1 Reverse:
                                     (SEQ ID NO: 21)
5'-CAA GTG GTT CTC CCC TAC CA-3'

ABL-R2 Reverse:
                                     (SEQ ID NO: 6)
5'-TCC ACT TCG TCT GAG ATA CTG GAT T-3'
```

Sequencing indicated a 35 bp insertion mutation in 27 patients (1.5%). Most of these samples showed a mixture of mutant and wild-type transcripts (mixed genotype). Rare samples (N=4) showed 100% alternatively spliced transcript without residual wild-type transcript. Sequence analysis showed that the 35 bp insert is a portion of normal sequence in the abl intron 8 that is inserted at the junction of abl exon 8 and exon 9 as shown in FIG. 2.

Nested PCR: The overall sensitivity of direct sequencing is approximately 20%. Therefore, low level transcript of the alternatively spliced bcr-abl transcript would not be detected by sequencing. To increase sensitivity of detecting 35 INS BCR-ABL, RT/PCR coupled with hemi-nested PCR was employed. RT/PCR provided the first round amplification of the fusion transcript. The RT/PCR reaction containing the bcr-abl kinase domain enriched amplicon was used as a template for a nested PCR reaction targeting abl exon 8-9 splice junction where the 35 bp insertion of abl introns 8 occurs. The expected size of the amplicon with 35 bp insertion is 253 bp and without the insertion is 218 bp.

Nested PCR was carried out with the following primers:

```
35 ins-Fwd:
                                     (SEQ ID NO: 22)
(6-Fam)5'-CGT CTG GGC ATT TGG AGT AT-3'

35 ins-Rev:
                                     (SEQ ID NO: 23)
5'-TCA AAG GCT TGG TGG ATT TC-3'
```

Analysis of Nested PCR Products: Nested PCR products were analyzed by ABI PRISM® 3100 Genetic analyzer (Applied Biosystems, Foster City, CA) by capillary electrophoresis. The size of the PCR fragments was analyzed by GeneScan® analysis software. The sizes were found to be 253 bp with the 35 bp insert and 218 bp without the insert. The percent of amplicons with insertion was assessed by measuring the ratio of the peak height of the 253 bp fragment to that of the total peak height (253 bp and 218 bp). Only samples having a 253 bp fragment peak >5% of the total peak were considered to be positive for the insertion/truncation mutation.

The percentage of the alternatively spliced of the total bcr-abl transcript is calculated (Table 1). As shown in Table 1, the highest rate of expression of the alternatively spliced bcr-abl is in the imatinib-resistant chronic phase CML (73%). Patients resistant to imatinib in Acc/blast phase have a lower rate of expression (21%). In contrast, newly diagnosed patients, in general, do not express the alternatively spliced bcr-abl mRNA. The alternatively spliced bcr-abl transcript detected in one untreated patient from 29 newly diagnosed patients. This patient had primary resistance and died within one year of diagnosis. Stored samples from patients treated with interferon-a but were resistant to therapy were also tested and only 20% of these patients expressed the alternatively spliced bcr-abl, albeit at low levels. The levels of the expression of the alternatively spliced bcr-abl varied between samples (Table 1). Only 20% of the patients in the chronic phase who expressed the alternatively spliced bcr-abl had a point mutation in the abl gene.

TABLE 1

Frequency of alternatively spliced bcr-abl transcript in CML patients.

| Patients | N tested | Positive (%) | % Median (range) | Association with abl point mutation (%) |
|---|---|---|---|---|
| Resistant Chronic Phase | 288 | 210 (73) | 16 (1-100) | 42 of 168 (25) |
| Resistant, Accelerated/Blast phase | 38 | 8 (21) | 17 (12-100) | 5 of 8 (63) |
| Newly Diagnosed | 29 | 1 (3) | 10 | None |
| Previously treated with INF-α | 25 | 5 (20) | 7 (5-20) | Not Available |

The results show that there is more association between kinase therapy resistance and the expression of the alternatively spliced bcr-abl in patients in the chronic phase. The frequency of the expression of the alternatively spliced bcr-abl in newly diagnosed patients or in patients treated by therapy other than imatinib is low and suggests that imatinib therapy selects for subclones that are capable of expressing the clones that express the alternatively spliced bcr-abl.

Sequence Confirmation: All samples with 253 bp fragment peak >20% of the total peak were confirmed by sequencing. Sequencing was performed in both forward and reverse direction using by dye terminator chemistry and ABI sequencer (Applied Biosystems, Foster City, CA) and using the primers below:

```
ABL-F1 Forward:
                              (SEQ ID NO: 7)
5'-CGC AAC AAG CCC ACT GTC T-3'

ABL-F2 Forward:
                              (SEQ ID NO: 8)
5'-TGG TAG GGG AGA ACC ACT TG-3'

ABL-R1 Reverse:
                              (SEQ ID NO: 21)
5'-CAA GTG GTT CTC CCC TAC CA-3'

ABL-R2 Reverse:
                              (SEQ ID NO: 6)
5'-TCC ACT TCG TCT GAG ATA CTG GAT T-3'
```

Translated amino acid sequence data of the bcr-abl insertion mutant was aligned with the wild type sequence c-abl oncogene (GenBank cDNA clone NM_005157) using ClustalW software (EMBL). Alignment results indicated that the insertion of 35 bp sequence of abl intron 8 at the splice junction of abl exon 8 and 9 in bcr-abl mRNA created a BCR-ABL protein with 10 novel amino acids inserted after amino acid 474 and a premature stop codon after 10 intron encoded amino acids (amino acid 484) (FIG. 3).

Example 3

Splice Variant Prediction

To understand the mechanism of insertion of the 35 bp abl intron 8 sequence into the junction of abl exons 8 and 9 in the bcr-abl gene, sequences of abl introns 8 and 9, and exons 8 and 9 were analyzed by GrailExp (Computational Biology at Oak Ridge National Laboratory, Oak Ridge, TN, USA) and FGENES (Softberry Inc., Mount Kisco, NY, USA) softwares for possible exon sites. Both softwares predicted that an insertion of 35 bp sequence from abl intron 8 between exon 8 and 9 will create an alternatively spliced bcr-abl mRNA with a new exon between exons 8 and 9 resulting in an insertion/truncation mutation (Table 2). Thus, the possible mechanism of the 35 bp insertion is aberrant RNA splicing.

Table 2. The predicted exon regions by two pattern-matching based programs. The numbers are the beginning and the end positions of the predicted exons ("GrailExp" and "FGENES"), and the observed exon positions ("abl exon 8" and 35 nucleotide insertion region). The numbering is based on the GenBank NC_000009.

| 35NT | GrailExp | FGENES | ABL exon 8 | 35NT insertion region |
|---|---|---|---|---|
| Predicted exon region 1 | 132743694 132743861 | 132743773 132743865 | 132743623 132743775 | |
| Predicted exon region 2 | 132744926 132745072 | 132744926 132745072 | | 132744926 132745072 |

Example 4

Homology Modeling

To understand the effect of the 35 bp insertion mutation on the activity of the BCR-ABL protein, the 3-D structure of the complex of the kinase domain of the mutated BCR-ABL protein with imatinib was compared to the kinase domain of wild-type Abl protein complexed with imatinib.

A homology model of BCR-ABL insertion/truncation mutant complexed with imatinib was generated using homology modeling software MODELLER, version 9v2 (Fiser, A. & Sali, A., Methods Enzymol. (2003), 374: 461-491) and using the crystal structure of BCR-ABL complexed with imatinib (chain A, PDB code: 1IEP, Nagar et al., Cancer Res. (2002), 62: 4236-4243) as template. The mutated and wild-type protein sequences of BCR-ABL were aligned using ClustalW software (EMBL). The aligned sequences were used as the input alignment to the MODELLER software and a global energy minimization was performed.

The modeled structure of the insertion/truncation mutant BCR-ABL protein obtained by the MODELLER software was similar to template wild type BCR-ABL structure. There was a slight conformational change after residue 475 and cutoff after residue 484. No global effect on the structure of BCR-ABL protein was observed due to the mutation despite a global energy minimization was performed in the homology modeling process.

Example 5

Molecular Dynamics Simulation

To further understand the effect of the 35 bp insertion mutation, molecular dynamic simulation of the insertion/truncation mutant BCR-ABL protein was performed using the three dimensional model of the insertion/truncation mutant BCR-ABL protein generated by the MODELLER software as the initial structure.

The simulated system contains 28,597 atoms (ABL: 4,207; imatinib: 68; water: 24,291; sodium ion: 19; chloride ion: 12). All preparation steps were done using the Visual Molecular Dynamics software package version 1.8.6 (Humphrey et al., J. Mol. Graphics (1996), 14:33-38). All molecular dynamics (MD) simulations were performed using the NAMD package, version 2.6 (Larkin et al., Bioinformatics (2007), 23:2947-2948) with the CHARMM27 force field (Mackerell et al., Encyclopedia of Computational Chemistry (1998), Vol. 1 (ed. Schreiner, P. R.) 271-277 (John Wiley & Sons, Chichester) and Brooks et al., J. Comput. Chem. (1983), 4:187-217). Full periodic boundary conditions were used along with the smooth particle mesh Ewald (PME) method (Essman et al., J. Chem. Phys. (1995), 103:8577-8593). Totally, a 20 ns MD production simulation was performed after a 10 ns solvent/ion equilibration simulation.

Molecular dynamic simulation showed that after 20 ns, the insertion/truncation mutant BCR-ABL protein exhibited major conformational changes in many regions of the Abl domain. Not only the insertion region (after residue 474) but also almost every alpha-helix of C-loop have significantly different conformations compared the homology model. In N-loop, the C-Helix moved into a different orientation and a position shift relative to the imatinib. Long-time simulations were necessary for studying the mutants of BCR-ABL to catch these global conformational movements.

The reduction of the interaction between C-helix and imatinib is the main reason of T315I imatinib resistance. The relative movement of C-Helix and nearby residues for T315I, insertion/truncation mutant, and E286K (as a control comparison) was evident. The patterns of C-helix movement were different for these three mutants: T315I showed larger movement for the whole C-helix; while the insertion/truncation mutant showed large movements scattered in different regions; and E286K had larger movement at E286 residue. The different movement patterns of C-helix may suggest that the cause of the movement is due to the packing changes near-T315 in the case of T315I; while in the case of the insertion/truncation mutant, the movement is due to the global conformational changes in many regions.

To further quantitatively identify the possible effect on the imatinib resistance of the insertion/truncation mutant of BCR-ABL protein, the interaction energy between imatinib and each residue of C-helix is calculated and shown in FIG. 4. In the case of T315I, the interaction energy changes of E286 and M290 are the main contributions of T315I drug resistance. Although the relative position changes of C-helix for the insertion/truncation mutant seem smaller than the changes of T315I, the insertion/truncation mutant in fact exhibited larger interaction changes due to the movement of C-helix and the binding between the imatinib and C-helix is weakened significantly. The calculated relative (to wide-type Abl protein) interaction energies change between C-helix (residues 278 to 290) and imatinib are 3.79 and 5.05 kcal/mole for T315I and 35INS, respectively; while the total binding energies of imatinib are 6.84 and 7.65 kcal/mole higher than wild-type for T315I and the insertion/truncation mutant respectively.

In the case of T315I, the binding energy losses of T315I/imatinib were mainly due to the relative position changes of residues E286 and M290 to imatinib, T315I mutation caused significant movement (over 40% on residue 280) of the whole C-helix (278-290). Another Abl tyrosine kinase inhibitor drug, nilotinib has close contact with E286, similar to imatinib (Weisberg et al., Br. J. Cancer (2006), 94:1765-1769). Another Abl tyrosine kinase inhibitor drug, dasatinib did not seem to interact directly with E286 residue; however T315I mutation still causes resistance to dasatinib (Weisberg et al., Br. J. Cancer (2006), 94:1765-1769). The resistance to dasatinib is most likely due to the effects of the T315I on whole C-helix and preventing the formation of an active Src site.

The interaction between residue M290 and imatinib is not reduced for the insertion/truncation mutant. Based on the simulation results, it seems likely that the insertion/truncation mutant will exhibit similar drug-resistance. The shift of the whole C-helix may suggest that a new drug with significant different binding mode, probably with much less interaction with C-helix but still with the ability to block the direct contact between the C-helix and the activation loop, is needed to overcome the resistance due to T315I and the insertion/truncation mutation.

Example 6

Cloning of a cDNA Encoding 35 INS BCR-ABL.

Plasmid pMIG-p210-BCR-ABL was obtained from Owen N. Witte (Howard Hughes Medical Institute/UCLA). This vector is a mammalian retroviral expression vector having high copy ampicillin resistance (modified pMSCV 2.2). The insertion/mutation construct pMIG-35INS-BCR-ABL was made by site-directed mutagenesis using the QuickChange Kit (Stratagene, La Jolla, CA) using the primers: BCR/ABL/35INS F1l: GAACTCATGCGAGCATACTTTGA-TAACCGTGAAGAAAGAACAAGATAGAAGGTT GGCAGTGGAATC (SEQ ID NO: 27). BCR/ABL/35INS R1: GATTCCACTGCCAACCTTCTATCTTGTTCTT TCTTCACGGTTATCAAAGTATGCTCGCATGAGTTC (SEQ ID NO: 28). Authenticity of all constructs was confirmed by DNA sequencing. The vector map is shown in FIGS. 5A-5B.

Example 7

Transfection of pMIG/35 INS Bcr-Abl into K562 Cells

K562 cells were cultured in RPMI 1640 medium supplemented with 10% heat-inactivated fetal bovine serum. Transfection of K562 cells was accomplished using Fugene™ 6 transfection reagent (Roche, Indianapolis, IN) protocol, holding total DNA content constant, and was performed according to the method described in Zhang et al., J. Biol. Chem. 283: 24047-24060, 2008.

Example 8

Figure 7:
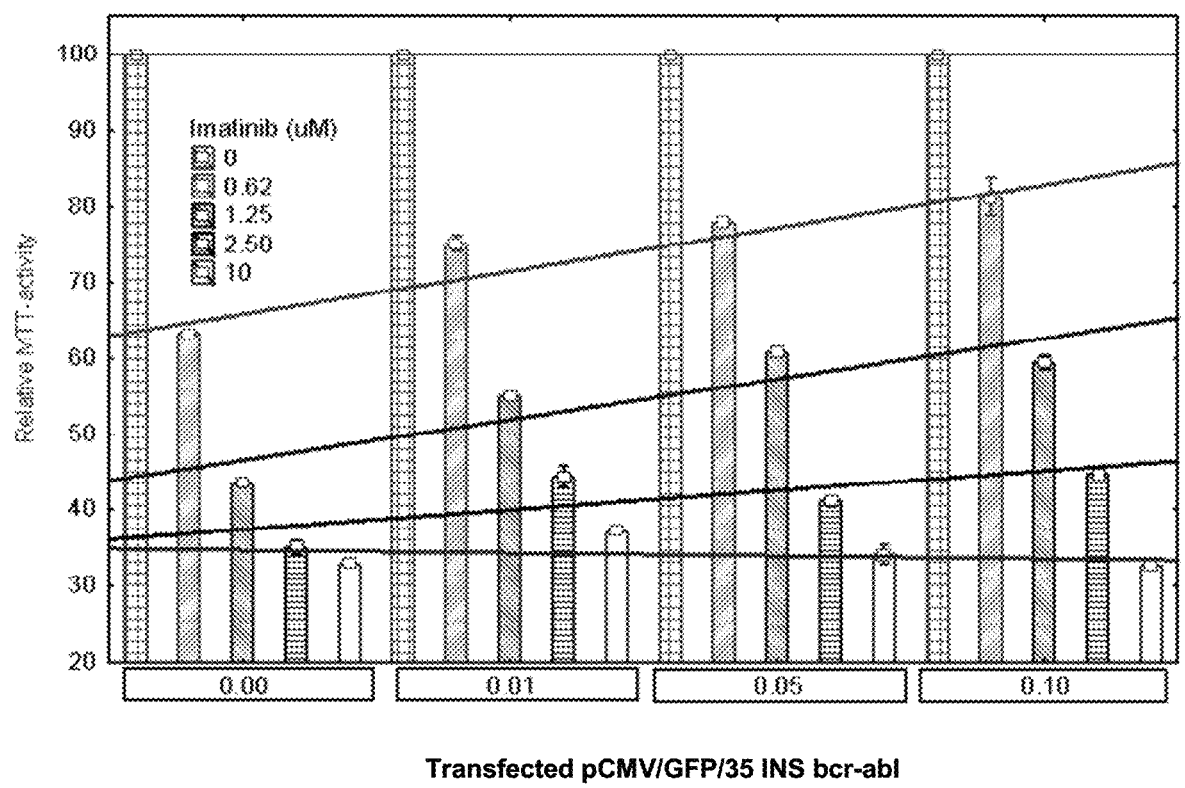
FIG. 7 shows the effect of imatinib concentration on the viability of cells transfected with increasing amounts of a vector encoding the 35 INS BCR-ABL spice variant (vector shown in FIG. 5B). The concentrations of imatinib range from zero to 10 ⊠ M are shown from left to right, respectively, for each cell transfection dose. The lines illustrate the trend of MTT activity as a function of increasing vector concentration.

Viability of K562 Cells Transfected with pCMV/GFP/35 INS Bcr-Abl at Increasing Concentration of Imatinib K562 cells transfected with the indicated amounts of pMIG/35 INS bcr-abl plasmid (0, 0.01, 0.05 or 0.10 μg), holding total vector concentration constant by adding pMIG "empty vector", were cultured for 48 hours with imatinib (0, 0.62, 1.25, 2.5 and 10 μM) 24 hours post-transfection as indicated in FIG. 7. The viability of the cells determined by MTT value for each pMIG/35 INS bcr-abl plasmid transfection level is shown in FIG. 7. Cell viability was observed to increase linearly with increasing amounts of pMIG/35 INS bcr-abl plasmid used to transfect the cells. These results demonstrate that the 35 INS bcr-abl gene product provides a dose dependent resistance to imatinib sensitivity.

Example 9

Detection of the Level of Phosphorylation of CrkL at Increasing Concentration of Imatinib.

Figure 8:
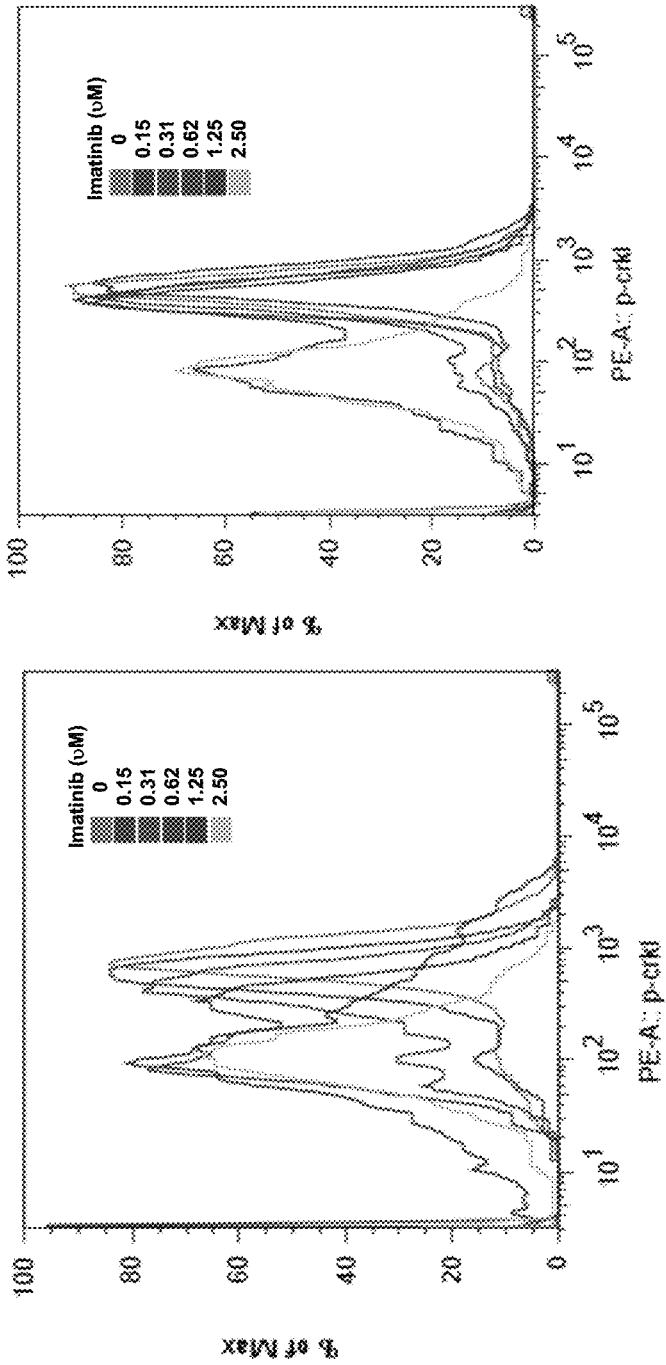
FIG. 8 shows the effect of imatinib concentration on phosphorylation of CrkL protein in K562 cells transfected with control (empty) pMIG vector (left panel) or transfected with 35 INS BCR-ABL splice variant (right panel)

K562 cells untransfected or transfected with pMIG/35 INS bcr-abl (0.10 µg) were incubated with various concentrations of imatinib (0, 0.15, 0.31, 0.62, 1.25 and 2.50 µM) and evaluated for the kinase activity of BCR-ABL demonstrated by phosphorylation of CrkL as described (Chan, et al., Methods Mol. Biol. 2007, 387:83). As shown in FIG. 8, the amount of phosphorylated CrkL in untransfected cells was reduced with increasing imatinib concentration showing that sensitivity of the expressed endogenous full length BCR-ABL to the activity of the drug. In contrast, K562 cells transfected with pMIG/35 INS bcr-abl, and which express both full length and the insertion/truncation 35 INS BCR-ABL gene product, showed little impact on CrkL phosphorylation at the lower doses of imatinib. Thus, expression of 35 INS BCR-ABL gene product in K562 cells conferred resistance to imatinib as evidenced by sustained CrkL phosphorylation at all but the highest doses of imatinib.

Example 10

Proliferation of K562 Cells Transfected with pMIG/35 INS Bcr-Abl in Presence of Imatinib.

Figure 9:
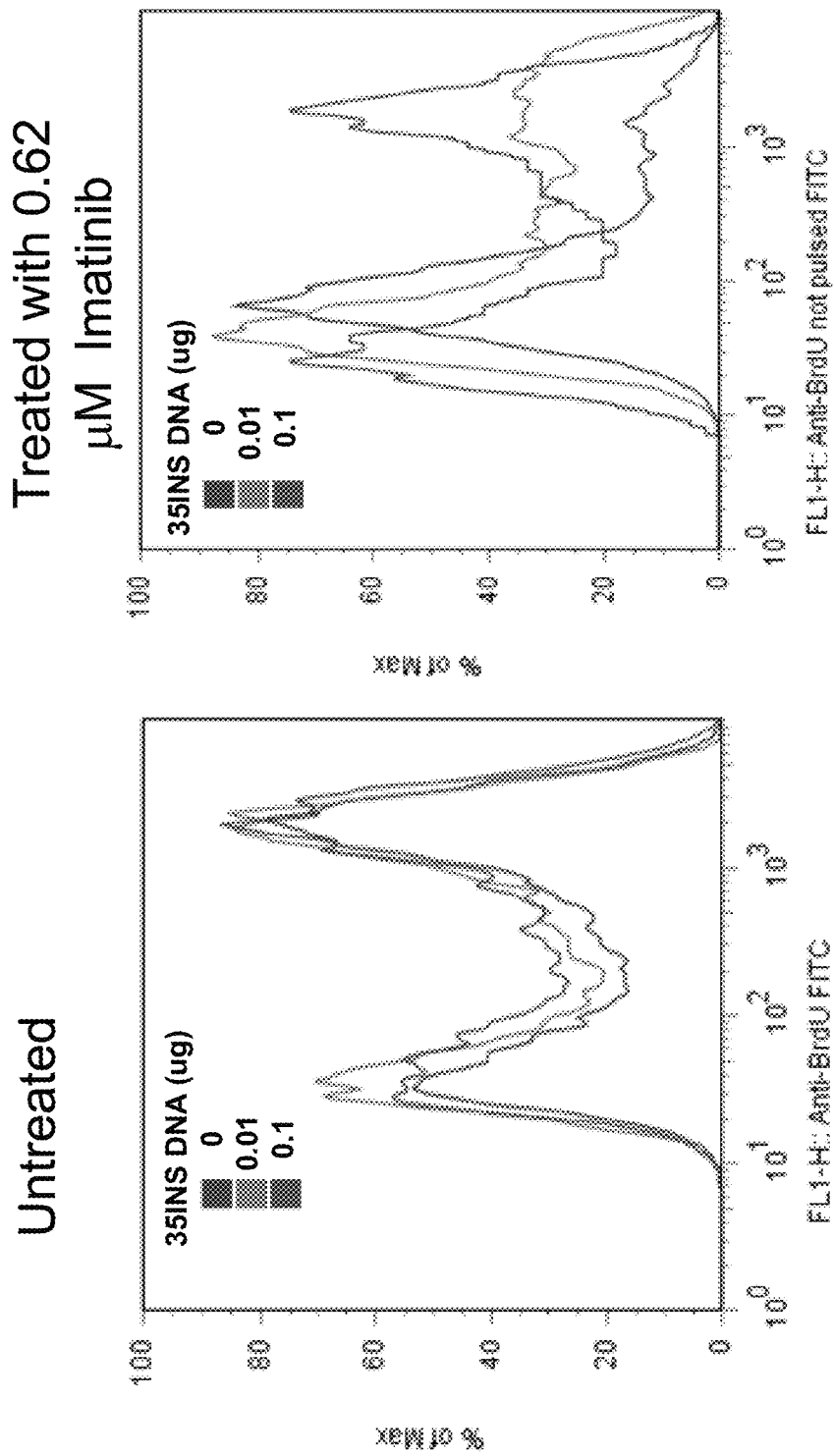
FIG. 9 shows the effect of increasing concentrations of vector encoding 35 INS BCR-ABL splice variant (vector shown in FIGS. 5A-5B) on proliferation of K562 cells either untreated (left panel) or treated with imatinib (right panel). Proliferation was measured as incorporation of BrdU into DNA.

K562 cells transfected with varying amounts of pMIG/35 INS bcr-abl (0, 0.01, 0.10 µg) were cultured with (0.62 µM) or without imatinib and evaluated for cell proliferation by measuring BrdU incorporation as described (Lin et al., Leuk Res. 2002, 26(6):551-9). As shown in FIG. 9, left panel, the fraction of cells synthesizing DNA (right hand peak) was not impacted by the amounts of vector used for transfection. Treatment with imatinib showed a reduction in cell proliferation except when the highest amounts of pMIG/35 INS bcr-abl vector (0.10 µg) was used for transfection. Thus, expression of 35 INS BCR-ABL gene product in K562 cells made them resistant to the cell growth inhibitory effects of imatinib.

Example 11

Detection of Expression of BCR-ABL and the Insertion/Truncation Mutant of 35 INS BCR-ABL Gene Product in CML Patients.

The percentages of 35 INS BCR-ABL relative to full length BCR-ABL gene product in patient samples was determined by RT/PCR coupled with semi-nested PCR as described in Example 2. Lysates prepared from the human cell line K562 and a patient cell sample containing 82.3% of BCR-ABL as 35 INS splice variant were subjected to western blotting to evaluate the relative protein concentration of the 35 INS BCR-ABL mutant. The lysates were immunoprecipitated with either anti-BCR antibody (7c6) (Santa Cruz Biotechnology) or anti-IgG antibody as indicated. The resulting immune-complexes were analyzed by western blotting developed using antibodies to different epitopes of Abl. The ABL K12 antibody (Santa Cruz Biotechnology) is directed against the kinase domain while the H300 antibody (Santa Cruz Biotechnology) is directed against the C-terminus of Abl. The lysates were also analyzed by western blotting with anti-actin antibody as a loading control. The results shown in FIG. 10A identify full length (210 kD) BCR-ABL in K562 cells and both full length (210 kD) and 35 INS truncated BCR-ABL (145 kD) in the patient sample. The H300 Abl C-terminal specific antibody failed to detect the BCR-ABL 35 INS product confirming that the native C-terminus of the Abl portion of the BCR-ABL 35 INS product was missing as predicted by the encoding sequence from the splice variant.

Figure 10B:
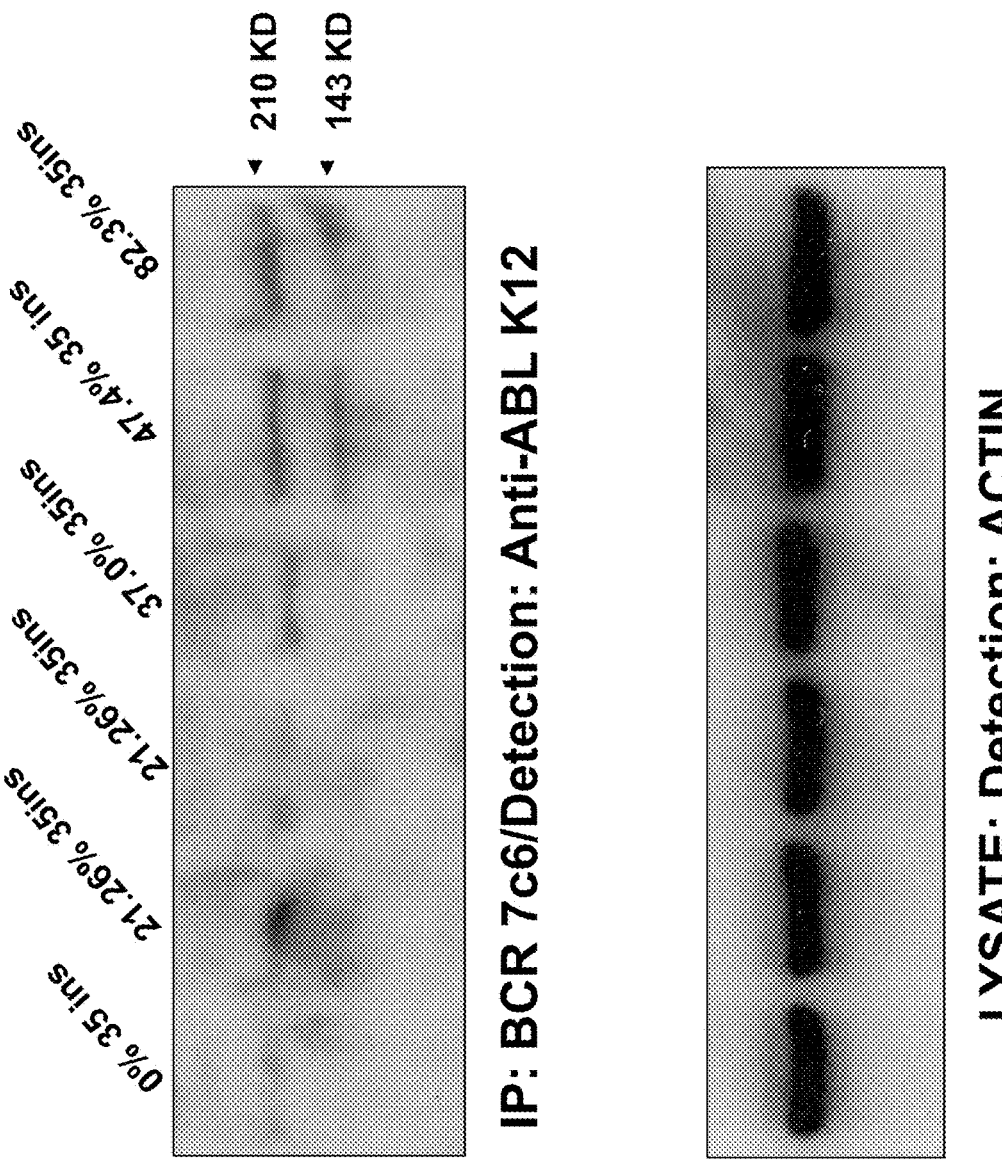
FIGS. 10A-10B show the detection of BCR-ABL and 35 INS BCR-ABL splice variant in CML patient samples. Lysates prepared from the human cell line K562 and a patient cell sample containing 82.3% of BCR-ABL as 35 INS splice variant were subjected to immunoprecipitation (IP) with anti-BCR antibody (7c6) or anti-IgG antibody. The resulting immune-complexes were analyzed by Western blotting developed using antibodies specific to different epitopes of Abl (ABL K12 is directed against kinase domain and H300 is directed to the C-terminus). The lysates were also analyzed by Western blotting with anti-actin antibody.
Figure 10A:
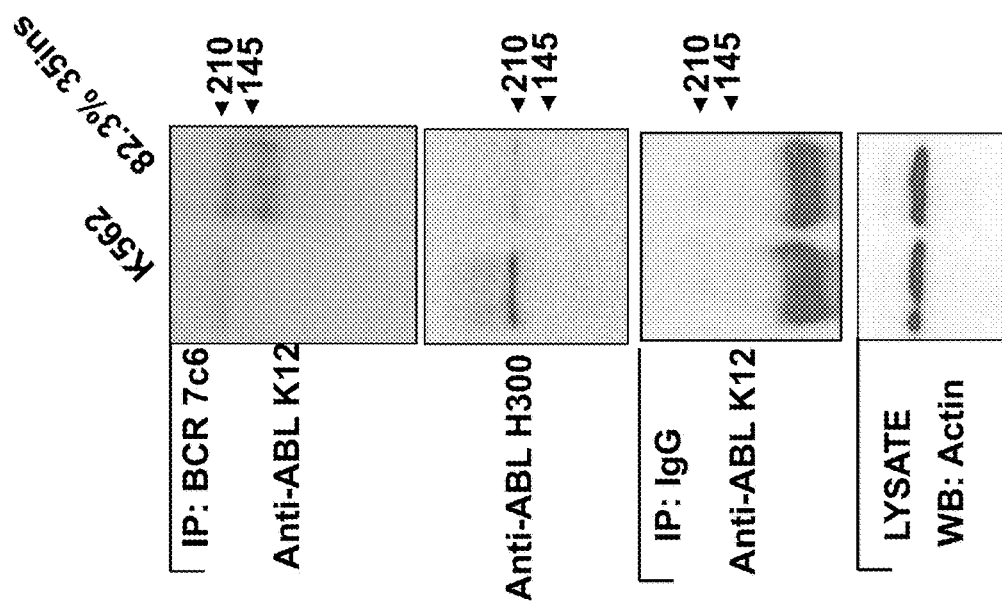

FIG. 10B shows six patient samples with various percentages of 35 INS BCR-ABL splice variant evaluated by western blotting using BCR 7c6 antibody for immunoprecipation and ABL K12 for the developing antibody. The truncated BCR-ABL 35 INS product was visualized in most patient samples.

Example 12

Determination of the Effect of BCR-ABL Kinase Inhibitors on Proliferation and Caspase 3 Activation of K562 Cells Transfected with BCR-ABL135INS.

Figure 18A:
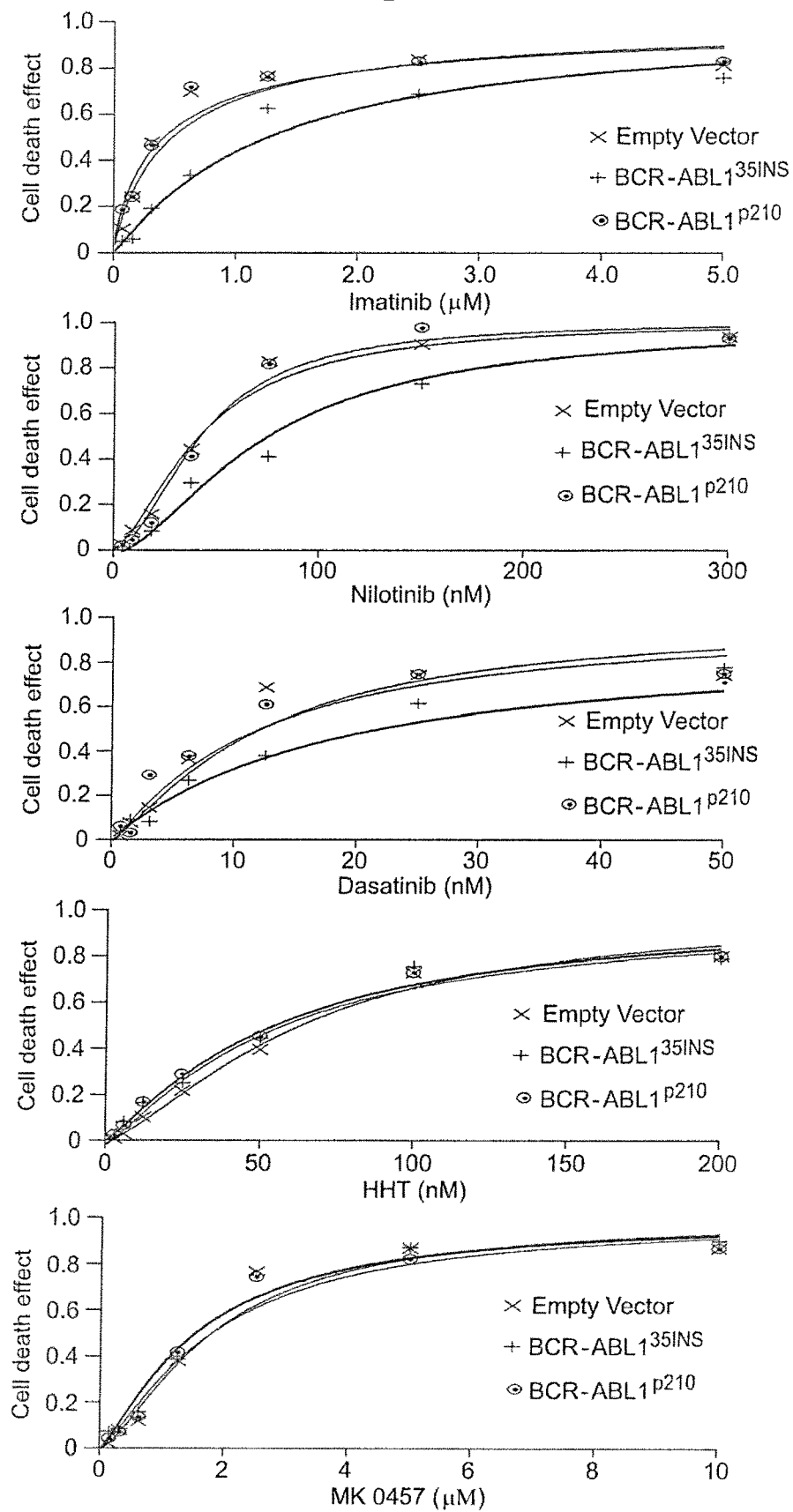

K562 cells were cotransfected with an increasing amount (0 to 100 ng) of plasmid pMIG/35 INS BCR-ABL and 100 ng of either pMIG/BCR-ABL1p210 or empty plasmid (pMIG). At 24 h after transfection, cells were treated for 48 h with various inhibitors: 1.2 µM imatinib, 5 nM nilotinib, 5 nM dasatinib, 100 nM HHT, or 2 µM MK0457. The effect of the drugs on cell proliferation was measured by MTT assay (FIG. 18A, right panel; mean±S.D; n=3). Dose response to cell death curves of K562 cells exposed to drugs were generated with the CalcuSyn® software package (Biosoft, Ferguson, MO) for each of at least three experiments. The doses that inhibited proliferation by 50% (IC50) were determined by the median-effect method.

To perform caspase assays, K562 cells were transiently transfected in 6-well dishes using the above procedure. At 24 h post-transfection, cells were suspended in caspase lysis buffer (10 mM HEPES [pH 7.4], 25 mM NaCl, 0.25% Triton X-100, 1 mM EDTA, and 5 mM dithiothreitol) and normalized for protein content. Typically, 15-25 µg of lysates were analyzed for protease activity by continuously measuring the release of fluorogenic substrate Ac-DEVD-aminofluoromethylcoumarin product from EMD (San Diego, CA) at 37° C., as described (Capdeville et al., Nat. Rev. Drug Discov. 2002, 1:493).

Imatinib, nilotinib, and dasatinib induced cell death in K562 cells, whereas transfection with the pMIG/35 INS bcr-abl construct induced resistance to cellular death. This pattern of resistance was dose dependent (see Table 3), in that the IC50 increased proportionally with the amount of pMIG/35 INS bcr-abl plasmid transfected into the CML cells. Relative to empty vector (pMIG) or wild-type pMIG/BCR-ABL1p210 vector, transfection with pMIG/35 INS bcr-abl vector yielded markedly increased IC50 values for imatinib (2.6-fold), nilotinib (1.7-fold), and dasatinib (1.4-fold). In contrast, 35 INS BCR-ABL expression did not induce resistance to Aurora kinase inhibitor MK0457 or to HHT, an inhibitor of protein synthesis. Therefore, the resistance caused by 35 INS BCR-ABL expression appear to be specific to Abl kinase inhibitors, and not to HHT or Aurora inhibitors. The effect of pCMV/GFP/BCR-ABL1p210 transfection in K562 CML cells was also tested. Expression of wild-type BCR-ABL1p210 did not induce resistance to imatinib, dasatinib, nilotinib, MK0457, or HHT.

TABLE 3

Effect of pMIG/35 INS bcr-abl transfection on $IC_{50}$ values of various drugs in K562 CML cells

| | $IC_{50 (nM)}$ | | | | |
|---|---|---|---|---|---|
| | Empty vector | pMIG/35 INS bcr-abl | | | pMIG/BCR-ABL1p210 |
| Drug | pCMV/ GFP | 0.01 µg DNA | 0.05 µg DNA | 0.1 µg DNA | 0.1 µg DNA |
| Imatinib | 474 | 503 | 920 | 1261 | 407 |
| Nilotinib | 42 | 52 | 54 | 71 | 42 |
| Dasatinib | 12 | 12 | 14 | 14 | 11 |
| HHT | 63 | 61 | 49 | 54 | 54 |
| MK-0457 | 1809 | 1998 | 1985 | 1536 | 1792 |

*$IC_{50}$ values indicate the median-effect dose in K562 cells carrying the wild-type BCR-ABL1 gene transfected with varying amounts of plasmid containing mutant BCR-ABL1, as determined by MTT assay.

Figure 18B:
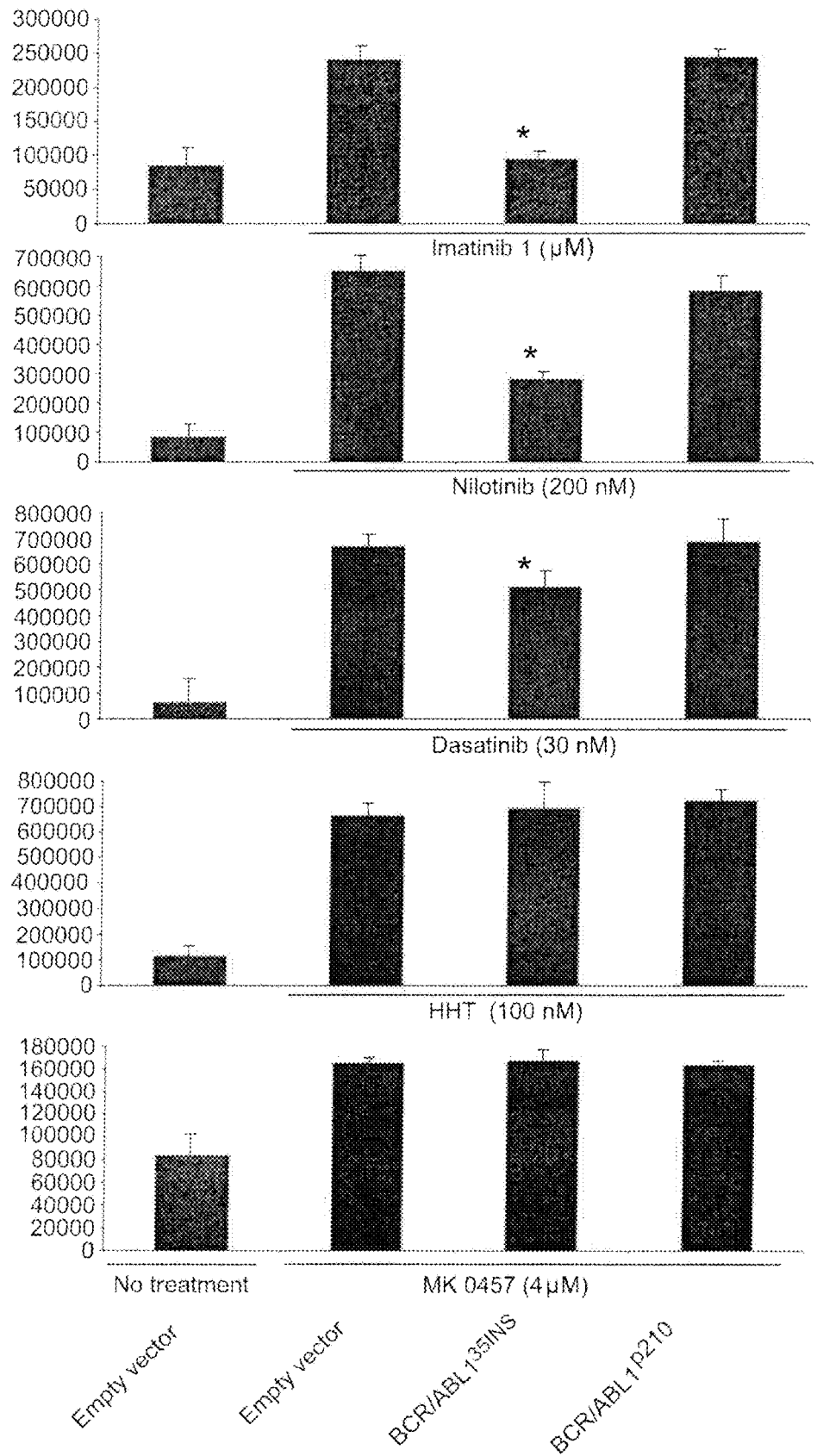

Induction of apoptosis measured by caspase-3 activation (mean [SD]; n=3) in K562 cells transfected with the different plasmids as described above and shown in FIG. 18B. Nilotinib and dasatinib are more potent than imatinib. Gene transfer of 35 INS BCR-ABL induced resistance to imatinib, nilotinib, and dasatinib, inhibiting caspase-3 activity, but did not affect the rate of caspase-3 activation in cells treated with MK0457 or HHT. In contrast, control transfection of BCR-ABL1p210 and empty vector did not affect the efficiency of the drugs.

Example 13

Determination of the Effect of BCR-ABL Kinase Inhibitors on Tyrosine Kinase Activity of K562 Cells Transfected with pMIG/35 INS Bcr-Abl.

K562 cells were cotransfected with increasing amounts of plasmid encoding pMIG/35 INS bcr-abl and either 100 ng of pMIG/BCR-ABL1p210 or the same amount of control vector (empty vector plasmid). At 24 h after transfection, cells were treated for 48 h with 1.2 µM imatinib mesylate and subjected to FACS analysis as described (Chan, et al., Methods Mol. Biol. 2007, 387:83). Rabbit polyclonal IgG anti-Lyn, anti-Aurora A, and anti-Aurora B were obtained from Santa Cruz Biotechnology, (Santa Cruz, CA); rabbit polyclonal IgG anti-p-Src, anti-p-StatS, and anti-p-Crkl were obtained from Cell Signaling (Danvers, MA). Goat anti-rabbit PE (Santa Cruz Biotechnology) was used as the secondary antibody. LYN, p-CRKL, p-SRC, p-STATS, and Aurora A and B status were monitored. All experiments were repeated at least three times. Asterisk indicates p<0.05 relative to Control (empty vector). Results are shown in FIG. 18C.

Tyrosine kinase assay was performed using the Universal Tyrosine Kinase Assay Kit (GenWay Biotech, San Diego, CA) according to the manufacturer's instruction. The universal protein tyrosine kinase substrate peptide, Poly (Glu-Tyr) (4:1, 20-50 kDa) was pre-coated onto 96-well microtiter plates. Serial dilutions of prepared cell extract and 5-point standards (with known tyrosine kinase activities) were added to the plate in triplicates along with an ATP-containing kinase buffer. After incubation at 37° C. for 30 min to allow phosphorylation of tyrosine residues, the sample solution was removed and the wells washed with Washing buffer (PBS with 0.05% Tween-20) and blocked with Blocking solution. Anti-phosphotyrosine (PY20)-horse radish peroxidase (HRP) conjugate was then added to the plate. After incubation at 37° C. for 30 min, the PY20-HRP solution was replaced by HRP substrate solution (TMBZ).

For colorimetric determination of PTK activity, the sample's specific absorbance at 450 nm was calculated from the standard curve. The results are shown in Table 4.

TABLE 4

Effect of transfection with mutant BCR-ABL1$^{35INS}$ allele on tyrosine kinase (TK) activity in K562 cells exposed to various TK inhibitors

| | Relative tyrosine kinase activity (%) | | |
|---|---|---|---|
| Drug treatment | Empty vector | BCR-ABL1$^{P210}$ | BCR-ABL1$^{35INS}$ |
| None | 100 | 100 | 100 |
| Imatinib (1.2 µM) | 57.3 | 87.7 | 100 |
| Nilotinib (5 nM) | 23.4 | 33.1 | 76.2 |
| Dasatinib (5 nM) | 15.6 | 20.6 | 42.7 |
| MK 0457 (2 µM) | 87.3 | 96.7 | 100 |
| Homoharringtonine (X µM) | 59.8 | 79.2 | 75.4 |

Experiments were performed in triplicate. TK data are expressed as activity relative to the no-drug control for each group.

Figure 19:
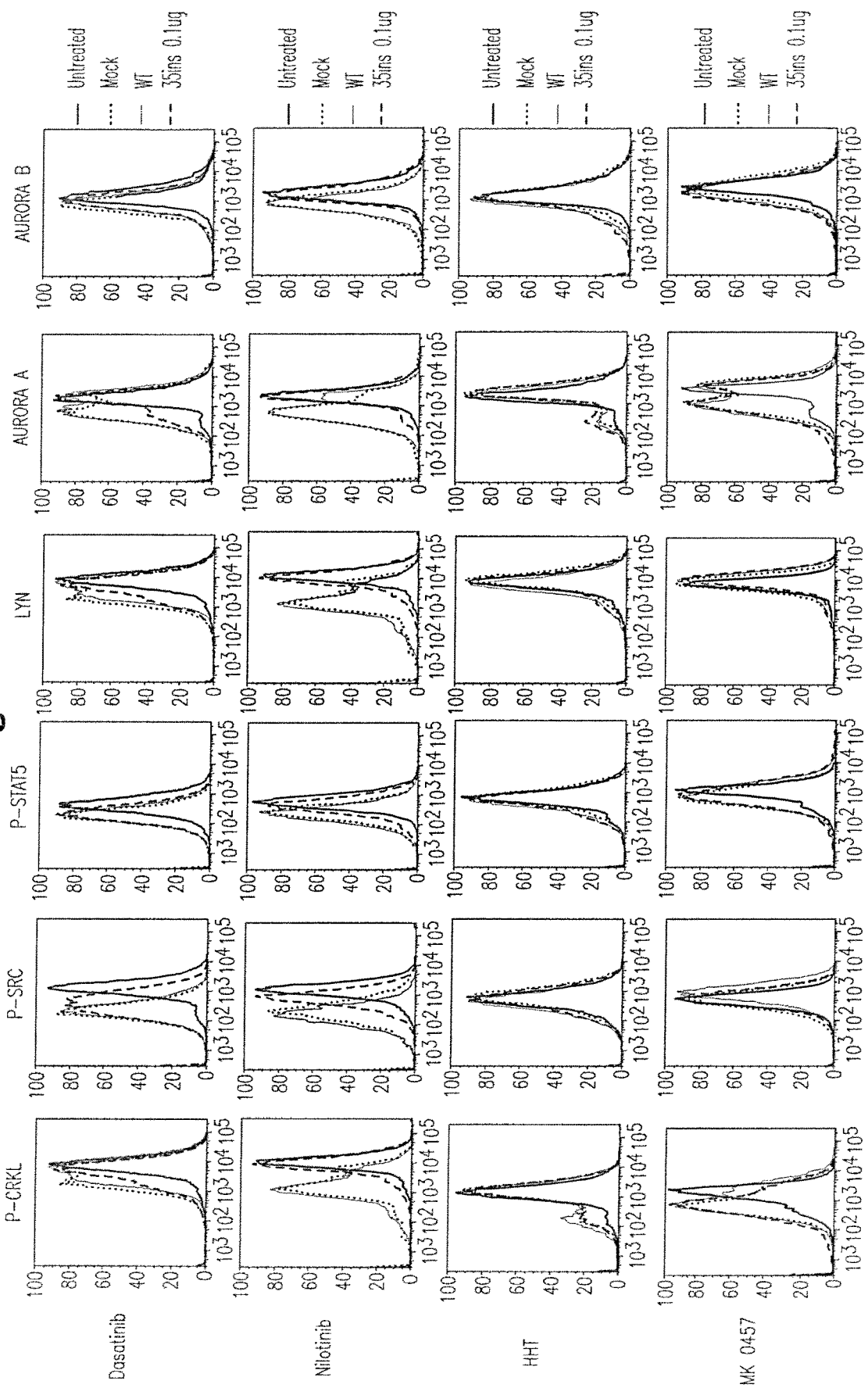
FIG. 19 shows the effects of BCR-ABL kinase inhibitors on various phosphorylation substrates in the absence and presence of 35 INS BCR-ABL expression in a CML cell line.

The effect of BCR-ABL kinase inhibitors on phosphorylation state of various substrates (CrkL, LYN, pSRC, pSTAT5, and Aurora A and B) in K562 cells transfected with pMIG/35 INS bcr-abl was also investigated (see FIG. 19) using the methods described in Example 9. Imatinib, nilotinib, and dasatinib inhibited phosphorylation of CrkL, a substrate of BCR-ABL kinase, as well as LYN, pSRC, and pSTAT5, but had no effect on Aurora A and B. However, transfection with pMIG/35 INS bcr-abl conferred dose-dependent resistance of kinases to inhibition by imatinib. 35 INS BCR-ABL expression had no effect on inhibition by HTT or MK 0457. In a control experiment, transfecting these cells with wild-type pMIG/BCR-ABL1p210 had no effect on the dephosphorylation effects of the various kinases.

Example 14

The Effect of BCR-ABL Kinase Inhibitor Combinations on Caspase-3 Activity and Cell Death of K562 Cells Transfected with BCR-ABL135INS.

Figure 20A:
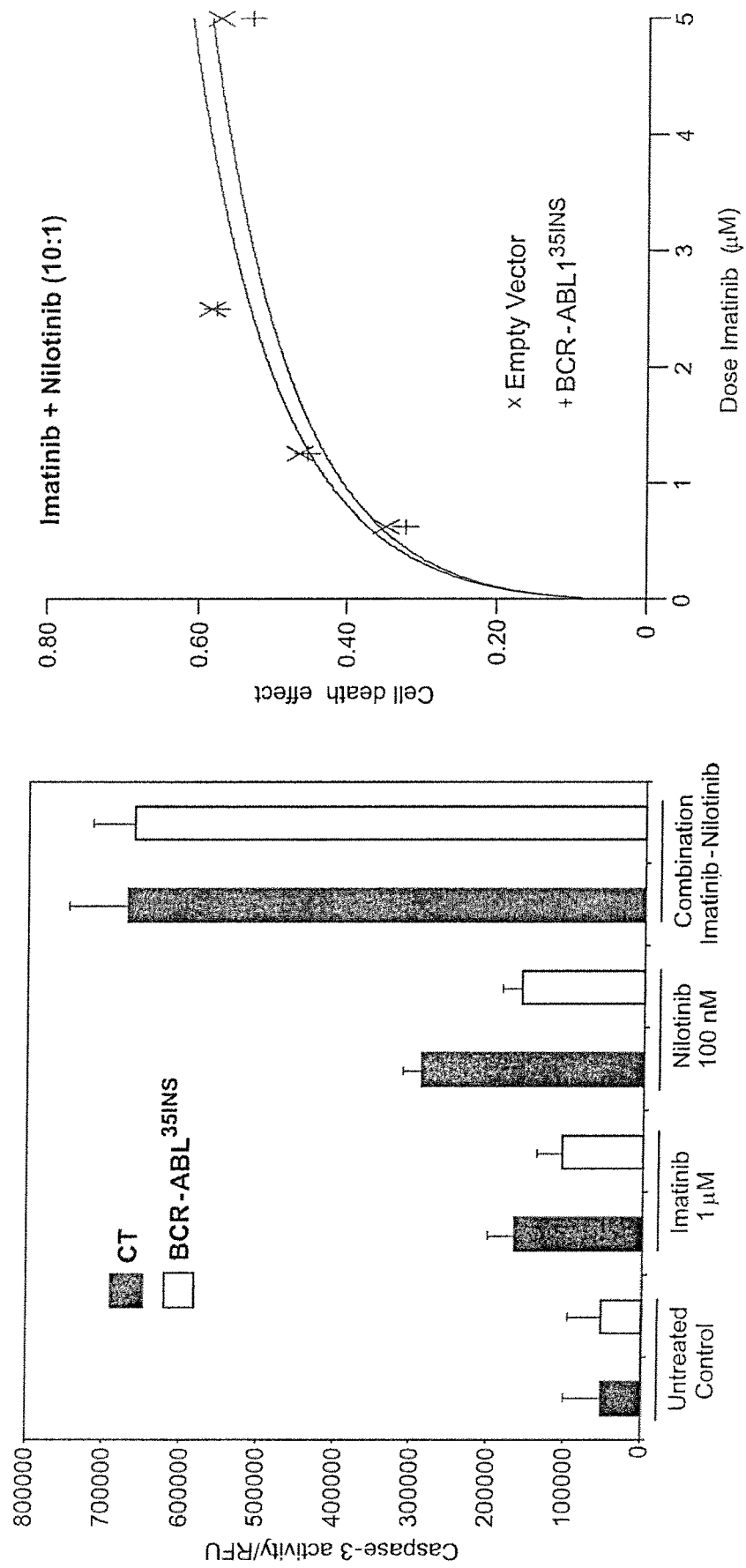
FIGS. 20A-20C show the effects of combinations of imatinib mesylate with nilotinib or HHT on BCR-ABL135INS kinase activity in a CML cell line. The effects of drug combinations were assessed by caspase-3 assay (left) and proliferation assay (right).
Figure 20B:
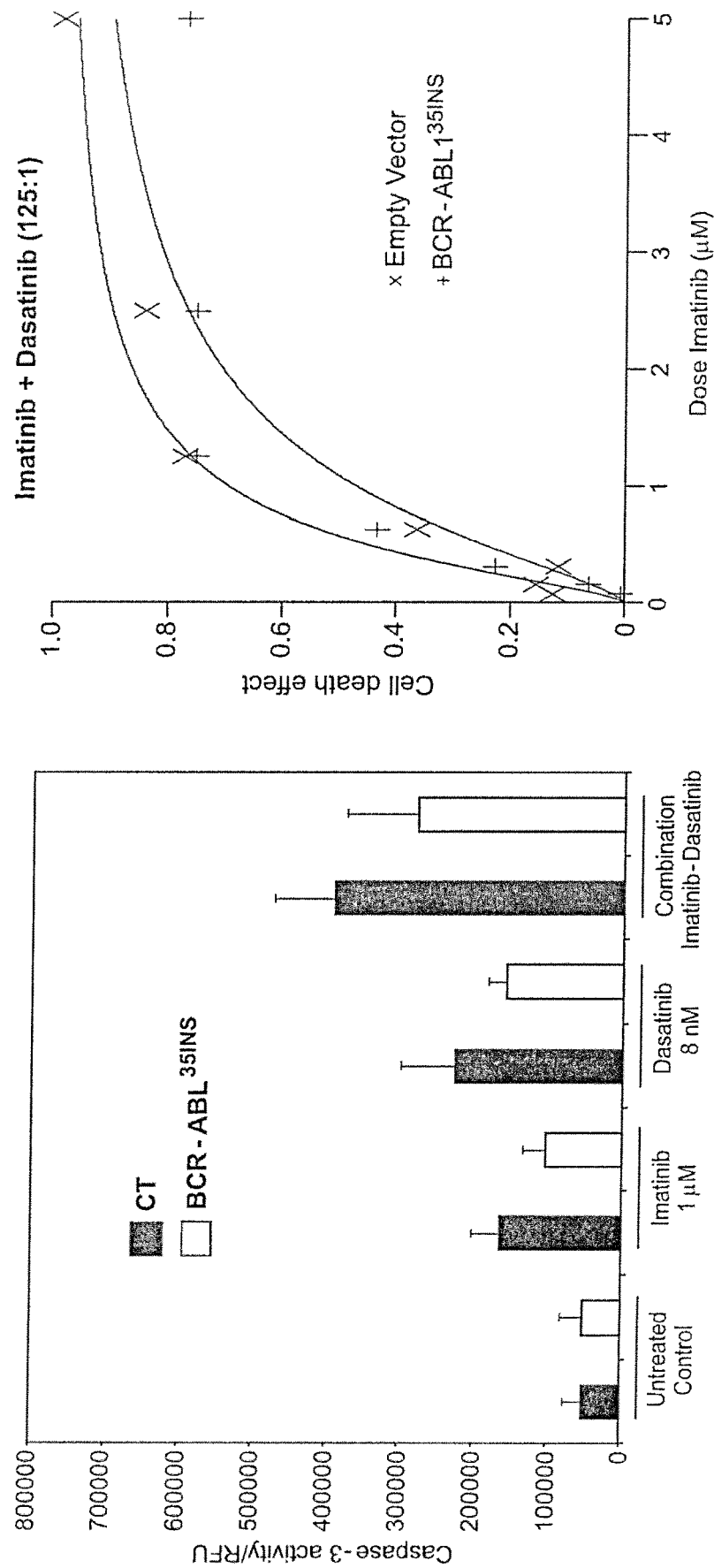
Figure 20C:
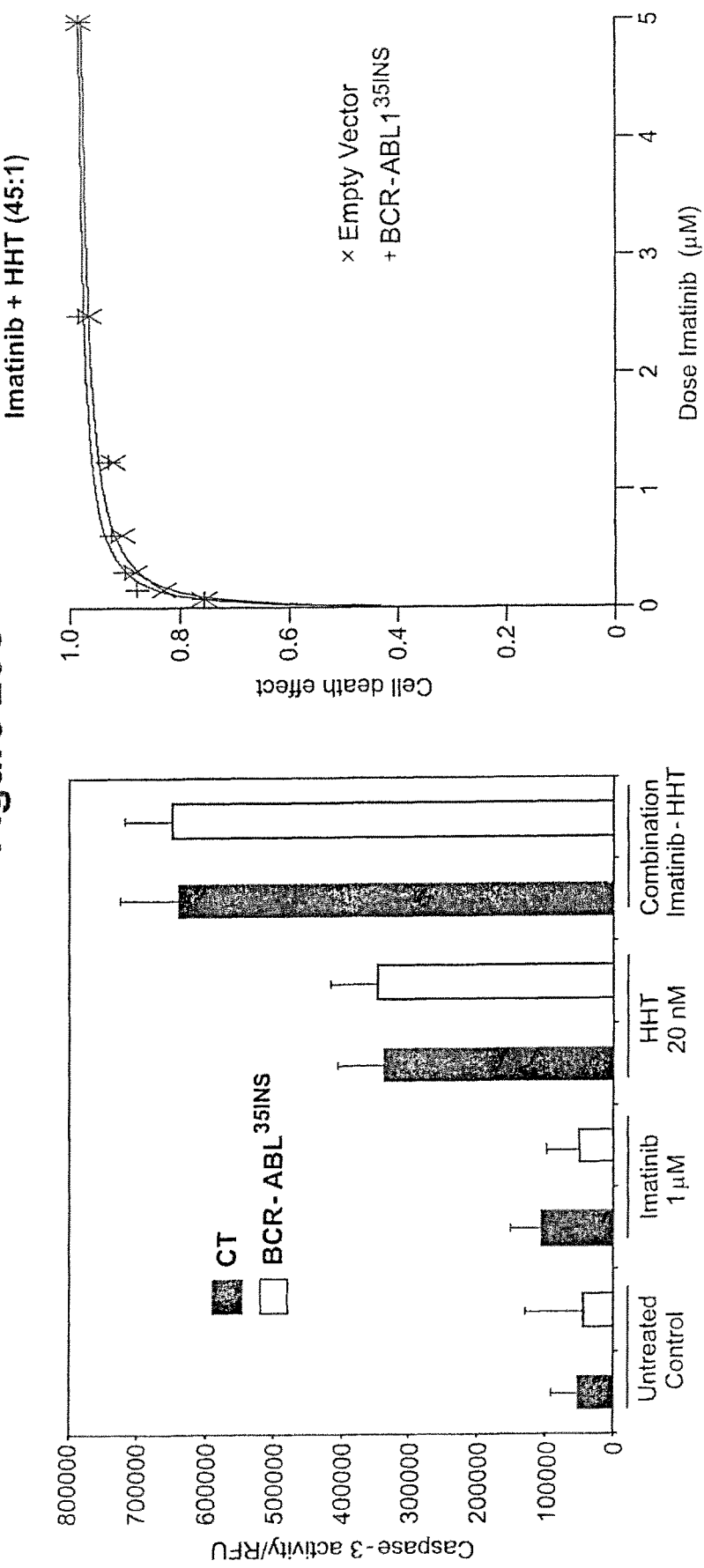
Figure 21A:
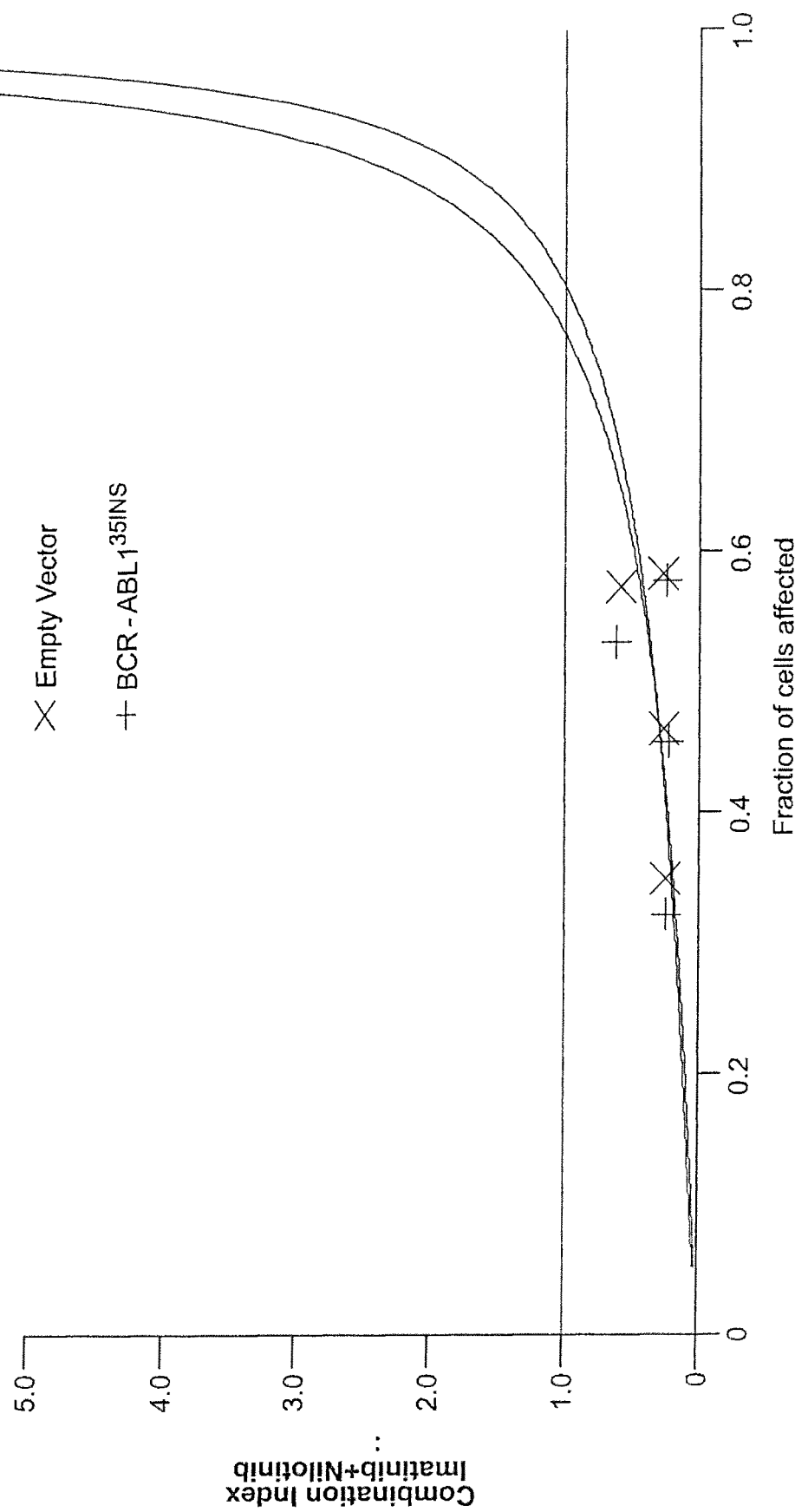
FIGS. 21A-21C show the effects of combinations of imatinib with nilotinib or HHT on 35 INS BCR-ABL kinase activity in a CML cell line. Isobolograms depict combination index (CI) values plotted against fraction of cells affected for (A) imatinib and nilotinib, (B) imatinib and dasatinib, and (C) imatinib and HTT.
Figure 21B:
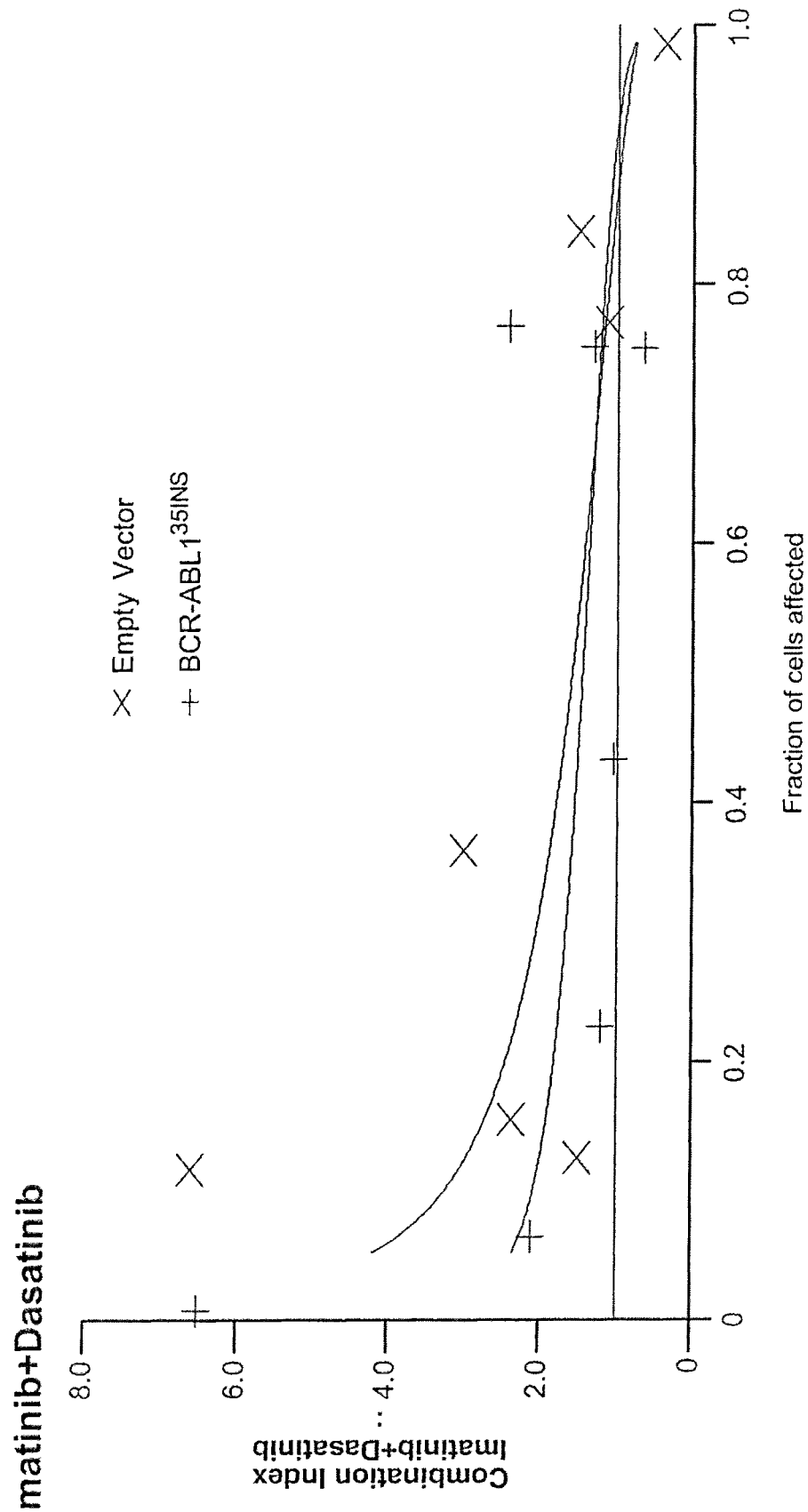
Figure 21C:
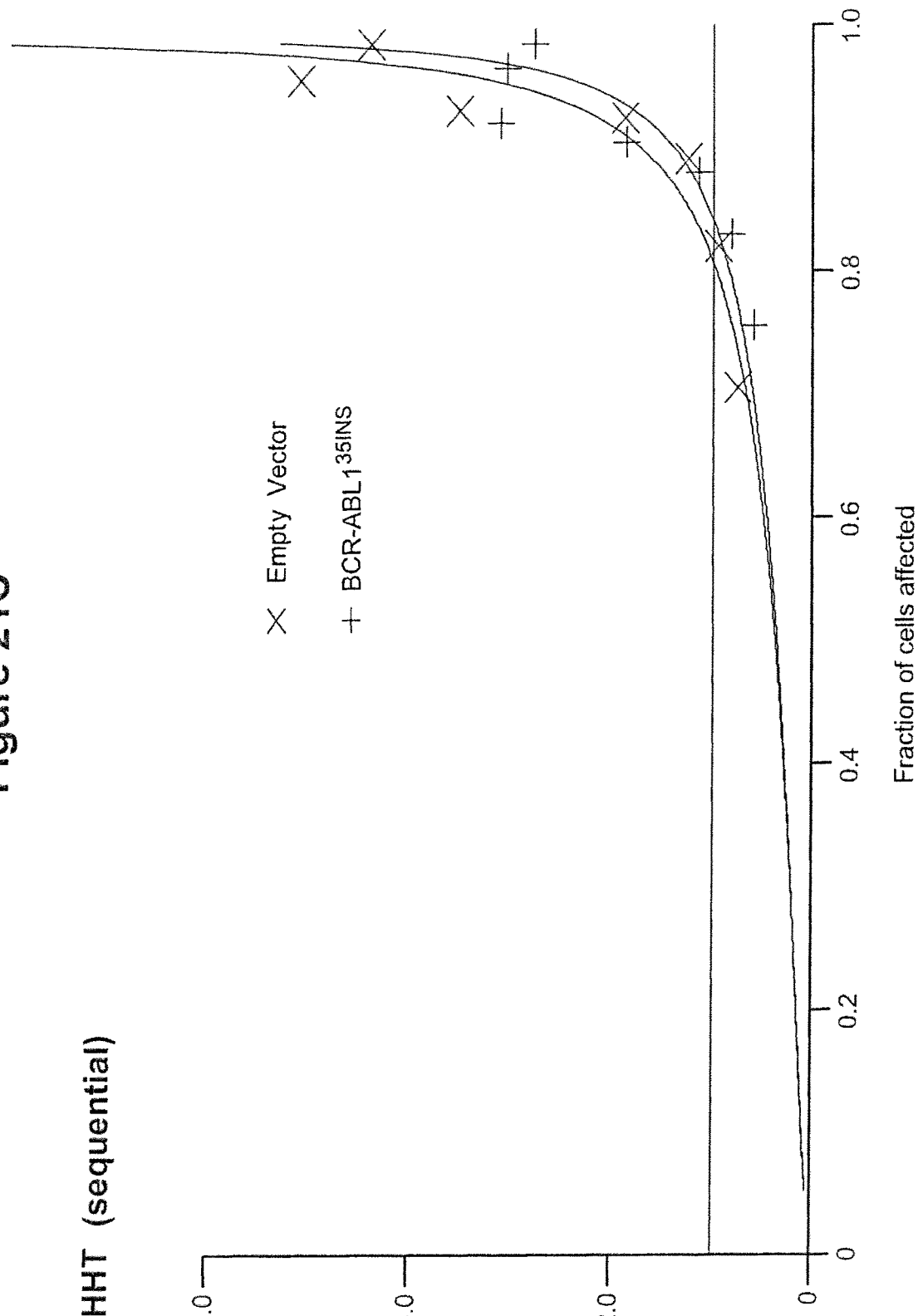

The effects of drug combinations were assessed by caspase-3 assay and proliferation assay and the results are shown in FIGS. 20A-20C. K562 cells transfected with either pMIG/35 INS bcr-abl construct or control (empty) vector (CT) were incubated with (A) imatinib and nilotinib or (B) imatinib and dasatinib for 48 hours. The combinations were in a fixed molar ratio (imatinib:nilotinib, 10:1; imatinib:dasatinib, 125:1) based on the IC50 values from Table 3. To assess the effect of imatinib in combination with HTT (molar ratio=45:1), cells were incubated for 24 hours with HHT and then for another 24 hours with HHT and imatinib. The results are shown in Table 5.

TABLE 5

Drug combination index values in K562 CML cells with or without K562 BCR-ABL$^{35INS}$-expression

| Drug Combination (ratio) | Combination Index Values | | |
|---|---|---|---|
| Cell Line | $ED_{50}$ | $ED_{75}$ | $ED_{90}$ |
| Imatinib:Nilotinib (10:1) | | | |
| K562 | 0.33 | 0.78 | 1.84 |
| K562 BCR-ABL$^{35INS}$ | 0.34 | 0.92 | 2.48 |

TABLE 5-continued

Drug combination index values in K562 CML cells with or without K562 BCR-ABL$^{35INS}$-expression

| Drug Combination (ratio) | Combination Index Values | | |
|---|---|---|---|
| Cell Line | ED$_{50}$ | ED$_{75}$ | ED$_{90}$ |
| Imatinib:Dasatinib (125:1) | | | |
| K562 | 1.59 | 1.19 | 0.92 |
| K562 BCR-ABL$^{35INS}$ | 1.45 | 1.23 | 1.04 |
| Imatinib:HHT (45:1)* | | | |
| K562 | 0.37 | 0.79 | 1.69 |
| K562 BCR-ABL$^{35INS}$ | 0.35 | 0.69 | 1.37 |

*Drug added sequentially.
ED$_{50}$, median effective dose (as opposed to concentration) at which 50% of individuals exhibit the specified quantal effect.

The effects of drug combinations on cell proliferation were assessed by MTT assays after incubation of cells for 24 hours with each individual drug and drug combination. The combinations were done either in a fixed molar ratio based on the median effect dose (Dm; drug dose required for 50% inhibition of survival) of each single drug, or in a matrix using five concentrations for each drug that achieve 10% to 50% inhibition alone. The effects of drug combinations were estimated using CalcuSyn software, which was developed based on the median-effect method created by Chou and Talalay (Adv. Enzyme Regul. 1984, 22:27). A calculated combination index (CI) of <1 indicates synergy; a CI of 1 indicates an additive effect; and a CI of >1 indicates antagonism. Isobolograms in FIGS. 20A-20C show combination index (CI) values plotted against fraction of cells affected. K562 CML cells were transfected either with BCR-ABL135INS construct or empty control vector (CT) after incubation with imatinib and nilotinib (A), imatinib and dasatinib (B) together for 48 hours or (C) Imatinib and HTT combination at a 45:1 molar ratio. Cells were incubated 24 hours with HHT and then for another 24 hours with HHT together with imatinib.

The combination of imatinib with nilotinib resulted strong synergy. Apoptosis demonstrated by the caspase-3 assay confirmed this synergy. This combination killed BCR-ABL135INS-expressing cells, resistant to imatinib and nilotinib separately, at the same rate as control cells. The combination of imatinib and dasatinib had an additive effect in caspase assays and slightly antagonist to slightly additive as shown in the isobologram. Synergy was observed when imatinib was given 24 hours after HHT. This result was confirmed by apoptosis assay.

Example 15

Kinetics of BIM Induction after Treatment with Imatinib Versus Combination of Imatinib Plus HHT.

Figure 22A:
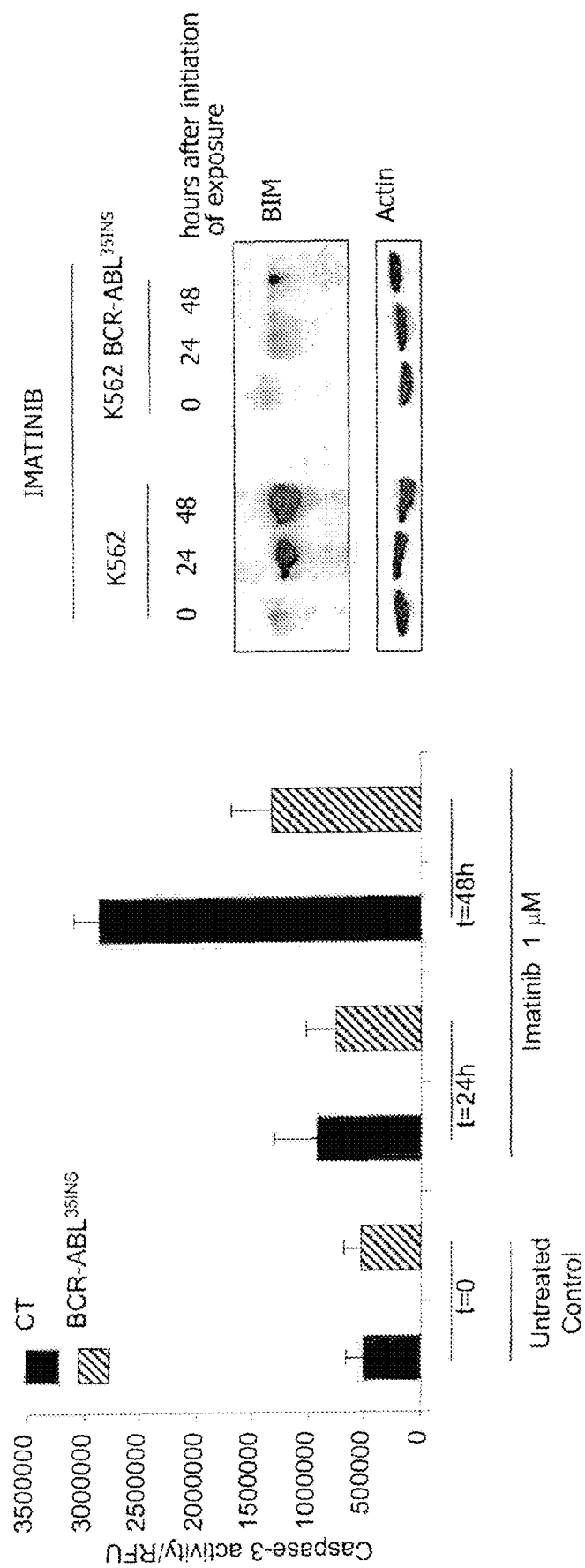
FIGS. 22A-22B show the kinetics of BIM induction after treatment with imatinib (FIG. 22A) and imatinib+HHT (FIG. 22B) continuously.
Figure 22B:
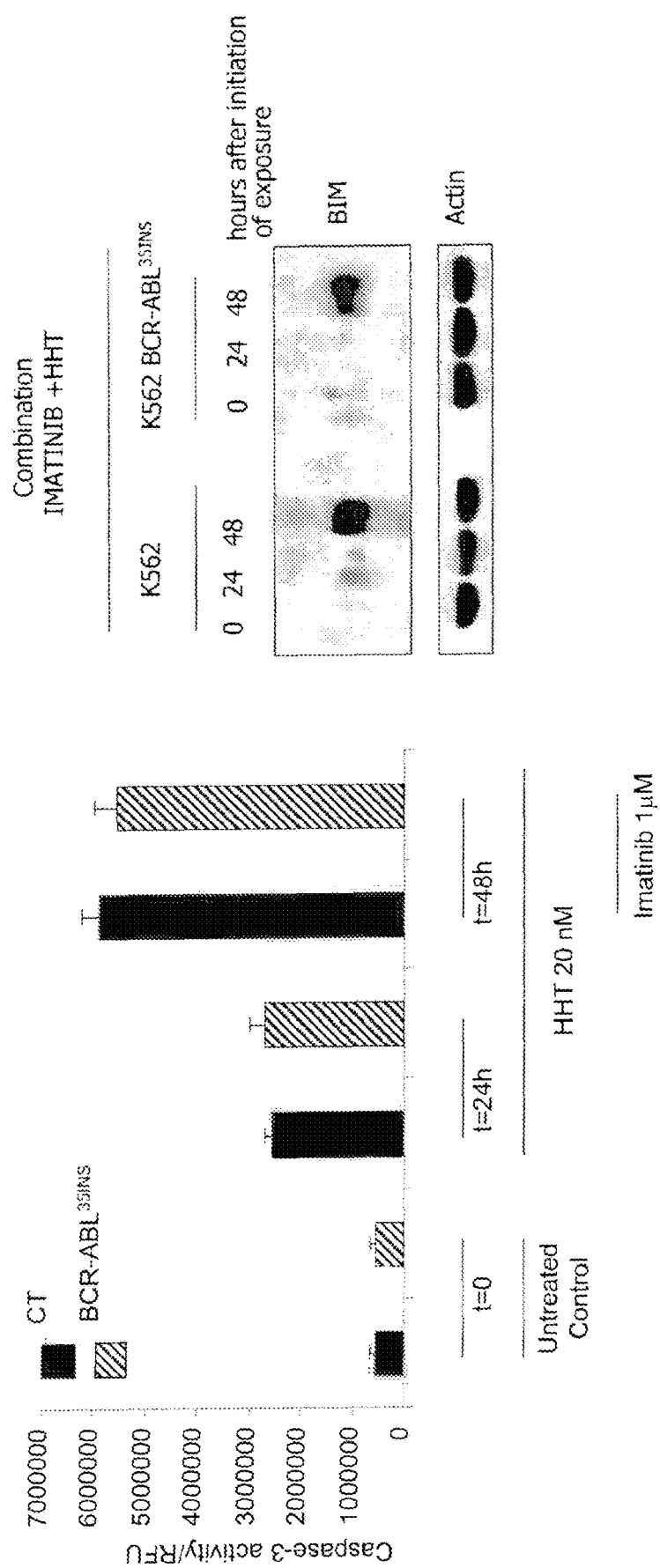

Upregulation of prosurvival Bcl-2 like proteins has been shown to influence response to cancer therapy. Imatinib enhances transcription of several proapoptotic proteins, including BIM (Kuroda et al., Proc. Natl. Acad. Sci. 2006, U.S.A. 103:14097). K562 cells transfected with empty control (CT) vector or pCMV/GFP/35 INS bcr-abl were treated with imatinib (22A) or imatinib+HHT (22B) continuously. Lysates were prepared at the times indicated and examined by caspase-3 assay (left) or by immunoblots using specific antibodies for BIM and actin (right) (see FIGS. 22A-22B).

Caspase-3 activation in CML K562 cells increased with time after continuous treatment with imatinib, and this increase was inhibited in cells transfected with the BCR-ABL135INS construct. For caspase-3 induction after sequential addition of HHT and imatinib, at 24 hours, HHT induced apoptosis at the same rate in both cell types. BIM was expressed at increased levels and migrated with faster mobility (due to dephosphorylation) after 24 to 48 hours' incubation with imatinib. K562 cells transfected with pMIG/35 INS bcr-abl exhibited reduced BIM expression relative to K562 parental cells. Surprisingly, the level of BIM induced by the combination of drugs was similar in the 2 different cell types. BIM was not induced by HHT treatment at 24 hours.

While not wishing to be bound by theory, given the requirement of dimerization for kinase activation, it may be that the truncated mutant 35 INS BCR-ABL has a dominant-negative effect on the native BCR-ABL via formation of heterodimers with decreased transphosphorylation. Along with BAD, BIM appears to be an integral component of imatinib-mediated CML cell killing (Id.). While not wishing to be bound by theory, the finding that 35 INS BCR-ABL expression reduces BIM overexpression, and that the loss of overexpression can be overcome by cotreatment with imatinib plus HHT, suggests an additional mechanistic reason that BCR-ABL135INS causes resistance to kinase inhibitors.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for predicting the likelihood for resistance of a chronic myelogenous leukemia (CML) patient with one or more BCR-ABL kinase inhibitors comprising:
   (a) obtaining a sample comprising a BCR-ABL protein from a patient diagnosed as having CML;
   (b) detecting the presence or absence of a polypeptide by contacting the sample with an antibody, wherein the antibody binds to an epitope comprising at least 15 contiguous amino acids of SEQ ID NO: 12 or at least 10 contiguous amino acids of SEQ ID NO: 10; and
   (c) indicating that the patient has an increased likelihood of being resistant to treatment with one or more BCR-ABL kinase inhibitors when the polypeptide is present.

2. The method of claim 1, wherein the antibody binds to an insertion/truncation mutant of BCR-ABL protein and not to a BCR-ABL protein without the mutation.

3. The method of claim 2, wherein the presence or absence of the polypeptide is determined by assessing the size of the protein.

4. The method of claim 3, wherein the antibody is a monoclonal or polyclonal antibody.

5. The method of claim 1, wherein one or more kinase inhibitors are selected from the group consisting of imatinib, nilotinib, bosutinib, and dasatinib.

6. The method of claim 5, wherein at least one kinase inhibitor is imatinib.

* * * * *

SEQUENCE LISTING

<160> NUMBER OF SEQ ID NOS: 30

<210> SEQ ID NO 1
<211> LENGTH: 278
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
catttggagt attgctttgg gaaattgcta cctatggcat gtccccttac ccgggaattg      60
acctgtccca ggtgtatgag ctgctagaga aggactaccg catggagcgc ccagaaggct     120
gcccagagaa ggtctatgaa ctcatgcgag catactttga taaccgtgaa gaaagaacaa     180
gatagaaggt tggcagtgga atccctctga ccggccctcc tttgctgaaa tccaccaagc     240
ctttgaaaca atgttccagg aatccagtat ctcagacg                             278
```

<210> SEQ ID NO 2
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Pro Tyr Pro Gly Ile Asp Leu Ser Gln Val Tyr Glu Leu Leu
1               5                   10                  15

Glu Lys Asp Tyr Arg Met Glu Arg Pro Glu Gly Cys Pro Glu Lys Val
            20                  25                  30

Tyr Glu Leu Met Arg Ala Tyr Phe Asp Asn Arg Glu Glu Arg Thr Arg
        35                  40                  45

<210> SEQ ID NO 3
<211> LENGTH: 1737
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
catttggagt attgctttgg gaaattgcta cctatggcat gtccccttac ccgggaattg      60
acctgtccca ggtgtatgag ctgctagaga aggactaccg catggagcgc ccagaaggct     120
gcccagagaa ggtctatgaa ctcatgcgta agccttcctc agcctgttct cacgagtata     180
tgtgggcatt ccaggaaatt caactgtgca ggagtgtgta cacaaagttg aaagtttttc     240
catgagctct ctccattcca gttcttcaga tgcagctaat gtagccattt gctacctatt     300
gacctttatt tacagataaa tagtatgtgc gtgacttgtc ttttaaagca aaaatggtat     360
tgatagatac caaacctggg tgtattccta aatacagatt cctgggccct gctttcacag     420
acattctgct atagtagcta agctcatgag gtgattttt ttttttttt ttttgagacg     480 gagtttcgct cttgtcgccc aggctggagt acaatggcgc aatgttggct cacttcaacc     540
tccacctccc tggttcaagc gattctcctg cctcagcctc ccaagtagct gggattacag     600
gcatgcacca ccacgcccgg ctaattttgt attttagta gagatggggt ttctccatgt     660
tagtcaggct ggtctccaac tcccaacctc aggtgatctg cctgcctcgg cctcccaaag     720
tgctgcgatt acaggcgtga gccaccacgc ccagctgcga ggtgattttt atctggtcgt     780
```

-continued

```
tttatactga ttacatatgt gttatctgta ctatgcacac acaggatgtt ttcatatatc    840
ttataaggta tttatatggc catttcttac actgttttcc cacacatgtc tttccacgtc    900
catatattca gatctctccc tctccctacc tcttatttat gtatagctgc ccagtactcc    960
atttcactca ttcatccggt cctcttttga tgtgcatttg gttgttttac acatttgttt   1020 ggttttttgcc cttataaaca aagcagaaac aaatattcat gtacacgaat ctctgggcac   1080
tttggctggt atttctaaaa gttgaactgt tggttccaag aactgtgtgg gttttaaatt   1140
ttgatacatt ttaccaaact gttaaaaaag gttgtgccat tgtatgctcc agtcagacgc   1200
atatgggagt gactgttcct ggtccccagt actaggcttt gtcagtctgt ttagtcctca   1260
tgttagtctc attttcatga gaatttcttt acttcagact ttgataaccg tgaagaaaga   1320
acaagataga aggtgagctg tttggcttag taattttcta cacctactag agcgggactg   1380
ggaaaaatat atttgtaaat gcagttcttg ctgtcactgt ctctctgggg ttttacaatc   1440
catattcctg ccagcatcta acgtcttttc aaattcttaa tgtctataac aggacatgat   1500
gacattcatc gttttgactt gttgcagcaa aagatggtta gcaggattgg aatgttgctt   1560
tcattctaga cttttccttg agaactgcta gccccgtatt gctagccaga tctcatggat   1620
gatctgactt gggtttcatc tgtccaggtt ggcagtggaa tccctctgac cggccctcct   1680
ttgctgaaat ccaccaagcc tttgaaacaa tgttccagga atccagtatc tcagacg     1737

<210> SEQ ID NO 4
<211> LENGTH: 35
<212> TYPE: DNA
<213> ORGANISM: Homo sapiens

<400> SEQUENCE: 4
actttgataa ccgtgaagaa agaacaagat agaag                                35

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgaccaactc gtgtgtgaaa ctc                                             23

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tccacttcgt ctgagatact ggatt                                           25

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```

```
cgcaacaagc ccactgtct                                                19
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
tggtagggga gaaccacttg                                               20
```

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
gagcatactt tgataaccgt gaagaaagaa caagatagaa ggttggc                  47
```

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Phe Asp Asn Arg Glu Glu Arg Thr Arg
1               5                   10

<210> SEQ ID NO 11
<211> LENGTH: 1644
<212> TYPE: PRT
<213> ORGANISM: Homo sapiens

<400> SEQUENCE: 11

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
                20                  25                  30

Gln Glu Leu Glu Arg Cys Lys Ala Ser Ile Arg Arg Leu Glu Gln Glu
            35                  40                  45

Val Asn Gln Glu Arg Phe Arg Met Ile Tyr Leu Gln Thr Leu Leu Ala
        50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
                100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ala Ser Gly Glu Arg Asp Asp
        130                 135                 140

Arg Gly Pro Pro Ala Ser Val Ala Ala Leu Arg Ser Asn Phe Glu Arg

-continued

```
145                 150                 155                 160
Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
                180                 185                 190

Asp Lys Glu Val Ser Asp Arg Ile Ser Ser Leu Gly Ser Gln Ala Met
                195                 200                 205

Gln Met Glu Arg Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
                260                 265                 270

Pro Leu Glu Tyr Gln Pro Tyr Gln Ser Ile Tyr Val Gly Gly Met Met
                275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
                340                 345                 350

Val Ser Pro Ser Pro Thr Thr Tyr Arg Met Phe Arg Asp Lys Ser Arg
                355                 360                 365

Ser Pro Ser Gln Asn Ser Gln Gln Ser Phe Asp Ser Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Gly Glu Gly Ala Phe His Gly Asp Ala Asp Gly Ser Phe Gly Thr
                420                 425                 430

Pro Pro Gly Tyr Gly Cys Ala Ala Asp Arg Ala Glu Glu Gln Arg Arg
                435                 440                 445

His Gln Asp Gly Leu Pro Tyr Ile Asp Ser Pro Ser Ser Ser Pro
    450                 455                 460

His Leu Ser Ser Lys Gly Arg Gly Ser Arg Asp Ala Leu Val Ser Gly
465                 470                 475                 480

Ala Leu Glu Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
                500                 505                 510

Tyr Leu Ser His Leu Gln Met Leu Thr Asn Ser Cys Val Lys Leu Gln
                515                 520                 525

Thr Val His Ser Ile Pro Leu Thr Ile Asn Lys Glu Glu Ala Leu Gln
                530                 535                 540

Arg Pro Val Ala Ser Asp Phe Glu Pro Gln Gly Leu Ser Glu Ala Ala
545                 550                 555                 560

Arg Trp Asn Ser Lys Glu Asn Leu Leu Ala Gly Pro Ser Glu Asn Asp
                565                 570                 575
```

```
Pro Asn Leu Phe Val Ala Leu Tyr Asp Phe Val Ala Ser Gly Asp Asn
            580                 585                 590

Thr Leu Ser Ile Thr Lys Gly Glu Lys Leu Arg Val Leu Gly Tyr Asn
        595                 600                 605

His Asn Gly Glu Trp Cys Glu Ala Gln Thr Lys Asn Gly Gln Gly Trp
    610                 615                 620

Val Pro Ser Asn Tyr Ile Thr Pro Val Asn Ser Leu Glu Lys His Ser
625                 630                 635                 640

Trp Tyr His Gly Pro Val Ser Arg Asn Ala Ala Glu Tyr Leu Leu Ser
                645                 650                 655

Ser Gly Ile Asn Gly Ser Phe Leu Val Arg Glu Ser Glu Ser Ser Pro
            660                 665                 670

Gly Gln Arg Ser Ile Ser Leu Arg Tyr Glu Gly Arg Val Tyr His Tyr
        675                 680                 685

Arg Ile Asn Thr Ala Ser Asp Gly Lys Leu Tyr Val Ser Ser Glu Ser
    690                 695                 700

Arg Phe Asn Thr Leu Ala Glu Leu Val His His Ser Thr Val Ala
705                 710                 715                 720

Asp Gly Leu Ile Thr Thr Leu His Tyr Pro Ala Pro Lys Arg Asn Lys
                725                 730                 735

Pro Thr Val Tyr Gly Val Ser Pro Asn Tyr Asp Lys Trp Glu Met Glu
            740                 745                 750

Arg Thr Asp Ile Thr Met Lys His Lys Leu Gly Gly Gly Gln Tyr Gly
        755                 760                 765

Glu Val Tyr Glu Gly Val Trp Lys Lys Tyr Ser Leu Thr Val Ala Val
    770                 775                 780

Lys Thr Leu Lys Glu Asp Thr Met Glu Val Glu Glu Phe Leu Lys Glu
785                 790                 795                 800

Ala Ala Val Met Lys Glu Ile Lys His Pro Asn Leu Val Gln Leu Leu
                805                 810                 815

Gly Val Cys Thr Arg Glu Pro Pro Phe Tyr Ile Ile Thr Glu Phe Met
            820                 825                 830

Thr Tyr Gly Asn Leu Leu Asp Tyr Leu Arg Glu Cys Asn Arg Gln Glu
        835                 840                 845

Val Asn Ala Val Val Leu Leu Tyr Met Ala Thr Gln Ile Ser Ser Ala
    850                 855                 860

Met Glu Tyr Leu Glu Lys Lys Asn Phe Ile His Arg Asp Leu Ala Ala
865                 870                 875                 880

Arg Asn Cys Leu Val Gly Glu Asn His Leu Val Lys Val Ala Asp Phe
                885                 890                 895

Gly Leu Ser Arg Leu Met Thr Gly Asp Thr Tyr Thr Ala His Ala Gly
            900                 905                 910

Ala Lys Phe Pro Ile Lys Trp Thr Ala Pro Glu Ser Leu Ala Tyr Asn
        915                 920                 925

Lys Phe Ser Ile Lys Ser Asp Val Trp Ala Phe Gly Val Leu Leu Trp
    930                 935                 940

Glu Ile Ala Thr Tyr Gly Met Ser Pro Tyr Pro Gly Ile Asp Leu Ser
945                 950                 955                 960

Gln Val Tyr Glu Leu Leu Glu Lys Asp Tyr Arg Met Glu Arg Pro Glu
                965                 970                 975

Gly Cys Pro Glu Lys Val Tyr Glu Leu Met Arg Ala Cys Trp Gln Trp
            980                 985                 990
```

```
Asn Pro Ser Asp Arg Pro Ser Phe Ala Glu Ile His Gln Ala Phe Glu
            995                 1000                1005

Thr Met Phe Gln Ser Ser Ile Ser Asp Glu Val Glu Lys Glu
    1010                1015                1020

Leu Gly Lys Gln Gly Val Arg Gly Ala Val Ser Thr Leu Leu Gln
    1025                1030                1035

Ala Pro Glu Leu Pro Thr Lys Thr Arg Thr Ser Arg Arg Ala Ala
    1040                1045                1050

Glu His Arg Asp Thr Thr Asp Val Pro Glu Met Pro His Ser Lys
    1055                1060                1065

Gly Gln Gly Glu Ser Asp Pro Leu Asp His Glu Pro Ala Val Ser
    1070                1075                1080

Pro Leu Leu Pro Arg Lys Glu Arg Gly Pro Pro Glu Gly Gly Leu
    1085                1090                1095

Asn Glu Asp Glu Arg Leu Leu Pro Lys Asp Lys Lys Thr Asn Leu
    1100                1105                1110

Phe Ser Ala Leu Ile Lys Lys Lys Lys Lys Thr Ala Pro Thr Pro
    1115                1120                1125

Pro Lys Arg Ser Ser Ser Phe Arg Glu Met Asp Gly Gln Pro Glu
    1130                1135                1140

Arg Arg Gly Ala Gly Glu Glu Gly Arg Asp Ile Ser Asn Gly
    1145                1150                1155

Ala Leu Ala Phe Thr Pro Leu Asp Thr Ala Asp Pro Ala Lys Ser
    1160                1165                1170

Pro Lys Pro Ser Asn Gly Ala Gly Val Pro Asn Gly Ala Leu Arg
    1175                1180                1185

Glu Ser Gly Gly Ser Gly Phe Arg Ser Pro His Leu Trp Lys Lys
    1190                1195                1200

Ser Ser Thr Leu Thr Ser Ser Arg Leu Ala Thr Gly Glu Glu Glu
    1205                1210                1215

Gly Gly Gly Ser Ser Ser Lys Arg Phe Leu Arg Ser Cys Ser Ala
    1220                1225                1230

Ser Cys Val Pro His Gly Ala Lys Asp Thr Glu Trp Arg Ser Val
    1235                1240                1245

Thr Leu Pro Arg Asp Leu Gln Ser Thr Gly Arg Gln Phe Asp Ser
    1250                1255                1260

Ser Thr Phe Gly Gly His Lys Ser Glu Lys Pro Ala Leu Pro Arg
    1265                1270                1275

Lys Arg Ala Gly Glu Asn Arg Ser Asp Gln Val Thr Arg Gly Thr
    1280                1285                1290

Val Thr Pro Pro Pro Arg Leu Val Lys Lys Asn Glu Glu Ala Ala
    1295                1300                1305

Asp Glu Val Phe Lys Asp Ile Met Glu Ser Ser Pro Gly Ser Ser
    1310                1315                1320

Pro Pro Asn Leu Thr Pro Lys Pro Leu Arg Arg Gln Val Thr Val
    1325                1330                1335

Ala Pro Ala Ser Gly Leu Pro His Lys Glu Glu Ala Gly Lys Gly
    1340                1345                1350

Ser Ala Leu Gly Thr Pro Ala Ala Ala Glu Pro Val Thr Pro Thr
    1355                1360                1365

Ser Lys Ala Gly Ser Gly Ala Pro Gly Gly Thr Ser Lys Gly Pro
    1370                1375                1380

Ala Glu Glu Ser Arg Val Arg Arg His Lys His Ser Ser Glu Ser
```

-continued

```
            1385               1390              1395

Pro Gly Arg Asp Lys Gly Lys Leu Ser Arg Leu Lys Pro Ala Pro
    1400              1405              1410

Pro Pro Pro Pro Ala Ala Ser Ala Gly Lys Ala Gly Gly Lys Pro
    1415              1420              1425

Ser Gln Ser Pro Ser Gln Glu Ala Ala Gly Glu Ala Val Leu Gly
    1430              1435              1440

Ala Lys Thr Lys Ala Thr Ser Leu Val Asp Ala Val Asn Ser Asp
    1445              1450              1455

Ala Ala Lys Pro Ser Gln Pro Gly Glu Gly Leu Lys Lys Pro Val
    1460              1465              1470

Leu Pro Ala Thr Pro Lys Pro Gln Ser Ala Lys Pro Ser Gly Thr
    1475              1480              1485

Pro Ile Ser Pro Ala Pro Val Pro Ser Thr Leu Pro Ser Ala Ser
    1490              1495              1500

Ser Ala Leu Ala Gly Asp Gln Pro Ser Ser Thr Ala Phe Ile Pro
    1505              1510              1515

Leu Ile Ser Thr Arg Val Ser Leu Arg Lys Thr Arg Gln Pro Pro
    1520              1525              1530

Glu Arg Ile Ala Ser Gly Ala Ile Thr Lys Gly Val Val Leu Asp
    1535              1540              1545

Ser Thr Glu Ala Leu Cys Leu Ala Ile Ser Arg Asn Ser Glu Gln
    1550              1555              1560

Met Ala Ser His Ser Ala Val Leu Glu Ala Gly Lys Asn Leu Tyr
    1565              1570              1575

Thr Phe Cys Val Ser Tyr Val Asp Ser Ile Gln Gln Met Arg Asn
    1580              1585              1590

Lys Phe Ala Phe Arg Glu Ala Ile Asn Lys Leu Glu Asn Asn Leu
    1595              1600              1605

Arg Glu Leu Gln Ile Cys Pro Ala Thr Ala Gly Ser Gly Pro Ala
    1610              1615              1620

Ala Thr Gln Asp Phe Ser Lys Leu Leu Ser Ser Val Lys Glu Ile
    1625              1630              1635

Ser Asp Ile Val Gln Arg
    1640

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Leu Met Arg Ala Tyr Phe Asp Asn Arg Glu Glu Arg Thr Arg
1               5                   10                  15

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gagcatactt tg                                                        12
```

```
<210> SEQ ID NO 14
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tagaaggttg gc                                                            12

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aactcatgcg agcatacttt gataaccgtg                                         30

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgcgagcat actttgataa                                                    20

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agaacaagat agaaggttgg cagtggaatc                                         30

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gaaggttggc agtggaatcc                                                    20

<210> SEQ ID NO 19
<211> LENGTH: 4902
<212> TYPE: DNA
<213> ORGANISM: Homo sapiens

<400> SEQUENCE: 19
atggtggacc cggtgggctt cgcggaggcg tggaaggcgc agttcccgga ctcagagccc        60
ccgcgcatgg agctgcgctc agtgggcgac atcgagcagg agctgagcg ctgcaaggcc       120 tccattcggc gcctggagca ggaggtgaac caggagcgct tccgcatgat ctacctgcag       180
```

```
acgttgctgg ccaaggaaaa gaagagctat gaccggcagc gatgggcctt ccggcgcgcg    240
gcgcaggccc ccgacggcgc ctccgagccc cgagcgtccg cgtcgcgccc gcagccagcg    300
cccgccgacg gagccgaccc gccgcccgcc gaggagcccg aggcccggcc cgacggcgag    360
ggttctccgg gtaaggccag gcccgggacc gcccgcaggc ccggggcagc cgcgtcgggg    420
gaacgggacg accggggacc ccccgccagc gtggcggcgc tcaggtccaa cttcgagcgg    480
atccgcaagg gccatggcca gcccggggcg gacgccgaga agcccttcta cgtgaacgtc    540
gagtttcacc acgagcgcgg cctggtgaag gtcaacgaca agaggtgtc ggaccgcatc     600 agctccctgg gcagccaggc catgcagatg gagcgcaaaa agtcccagca cggcgcgggc    660
tcgagcgtgg gggatgcatc caggcccct taccggggac gctcctcgga gagcagctgc     720
ggcgtcgacg gcgactacga ggacgccgag ttgaacccc gcttcctgaa ggacaacctg      780
atcgacgcca atggcggtag caggcccct tggccgcccc tggagtacca gccctaccag      840
agcatctacg tcgggggcat gatggaaggg gagggcaagg gcccgctcct cgcgcagccag    900 agcacctctg agcaggagaa gcgccttacc tggccccgca ggtcctactc ccccggagt     960 tttgaggatt gcggaggcgg ctatacccg gactgcagct ccaatgagaa cctcacctcc     1020
agcgaggagg acttctcctc tggccagtcc agccgcgtgt ccccaagccc caccacctac    1080
cgcatgttcc gggacaaaag ccgctctccc tcgcagaact cgcaacagtc cttcgacagc    1140
agcagtcccc ccacgccgca gtgccataag cggcaccggc actgcccggt tgtcgtgtcc    1200
gaggccacca tcgtgggcgt ccgcaagacc gggcagatct ggcccaacga tggcgagggc    1260
gccttccatg gagacgcaga tggctcgttc ggaacaccac ctggatacgg ctgcgctgca    1320
gaccgggcag aggagcagcg ccggcaccaa gatgggctgc cctacattga tgactcgccc    1380
tcctcatcgc cccacctcag cagcaagggc aggggcagcc gggatgcgct ggtctcggga    1440
gccctggagt ccactaaagc gagtgagctg gacttggaaa agggcttgga gatgagaaaa    1500
tgggtcctgt cgggaatcct ggctagcgag gagacttacc tgagccacct ggaggcactg    1560
ctgctgccca tgaagccttt gaaagccgct gccaccacct tcagccggt gctgacgagt     1620 cagcagatcg agaccatctt cttcaaagtg cctgagctct acgagatcca caaggagttc    1680 tatgatggc tcttccccg cgtgcagcag tggagccacc agcagcgggt gggcgacctc      1740
ttccagaagc tggccagcca gctggtgtgt accgggtct taggctataa tcacaatggg     1800
gaatggtgtg aagcccaaac caaaatggc caaggctggg tcccaagcaa ctacatcacg     1860
ccagtcaaca gtctggagaa acactcctgg taccatgggc ctgtgtcccg caatgccgct    1920
gagtatctgc tgagcagcgg gatcaatggc agcttcttgg tgcgtgagag tgagagcagt    1980
cctggccaga ggtccatctc gctgagatac gaagggaggg tgtaccatta caggatcaac    2040
actgcttctg atggcaagct ctacgtctcc tccgagagcc gcttcaacac cctggccgag    2100
ttggttcatc atcattcaac ggtggccgac gggctcatca ccacgctcca ttatccagcc    2160
ccaaagcgca caagcccac tgtctatggt gtgtccccca actacgacaa gtgggagatg    2220
gaacgcacgg acatcaccat gaagcacaag ctgggcgggg ccagtacgg ggaggtgtac     2280 gagggcgtgt ggaagaaata cagcctgacg gtggccgtga agaccttgaa ggaggacacc    2340
atggaggtgg aagagttctt gaaagaagct gcagtcatga aagagatcaa acaccctaac    2400
ctggtgcagc tccttgggt ctgcacccgg gagcccccgt tctatatcat cactgagttc    2460
atgacctacg ggaacctcct ggactacctg agggagtgca accggcagga ggtgaacgcc    2520
```

```
gtggtgctgc tgtacatggc cactcagatc tcgtcagcca tggagtacct ggagaagaaa   2580
aacttcatcc acagagatct tgctgcccga aactgcctgg tagggagaa ccacttggtg    2640 aaggtagctg attttggcct gagcaggttg atgacagggg acacctacac agcccatgct   2700
ggagccaagt tccccatcaa atggactgca cccgagagcc tggcctacaa caagttctcc   2760
atcaagtccg acgtctgggc atttggagta ttgctttggg aaattgctac ctatggcatg   2820
tccccttacc cgggaattga cctgtcccag gtgtatgagc tgctagaaa ggactaccgc    2880 atggagcgcc agaaggctg cccagagaag gtctatgaac tcatgcgagc atgttggcag    2940
tggaatccct ctgaccggcc ctcctttgct gaaatccacc aagcctttga acaatgttc    3000 caggaatcca gtatctcaga cgaagtggaa aaggagctgg ggaaacaagg cgtccgtggg   3060
gctgtgagta ccttgctgca ggccccagag ctgcccacca agacgaggac ctccaggaga   3120
gctgcagagc acagagacac cactgacgtg cctgagatgc tcactccaa gggccaggga    3180 gagagcgatc ctctggacca tgagcctgcc gtgtctccat tgctccctcg aaaagagcga   3240 ggtccccgg agggcggcct gaatgaagat gagcgccttc tccccaaaga caaaaagacc    3300
aacttgttca gcgccttgat caagaagaag aagaagacag ccccaacccc tcccaaacgc   3360
agcagctcct tccgggagat ggacggccag ccggagcgca gaggggccgg cgaggaagag   3420
ggccgagaca tcagcaacgg ggcactggct ttcacccccct tggacacagc tgacccagcc   3480
aagtccccaa agcccagcaa tggggctggg gtccccaatg gagccctccg ggagtccggg   3540
ggctcaggct tccggtctcc ccacctgtgg aagaagtcca gcacgctgac cagcagccgc   3600
ctagccaccg cgcaggagga gggcggtggc agctccagca gcgcttcct gcgctcttgc   3660 tccgcctcct gcgttcccca tggggccaag gacacggagt ggaggtcagt cacgctgcct   3720
cgggacttgc agtccacggg aagacagttt gactcgtcca catttggagg gcacaaaagt   3780
gagaagccgg ctctgcctcg gaagagggca ggggagaaca ggtctgacca ggtgacccga   3840
ggcacagtaa cgcctccccc caggctggtg aaaaagaatg aggaagctgc tgatgaggtc   3900
ttcaaagaca tcatggagtc cagcccgggc tccagcccgc caacctgac tccaaaaccc   3960 ctccggcgga aggtcaccgt ggcccctgcc tcgggcctcc cccacaagga agaagctgga   4020
aagggcagtg ccttagggac ccctgctgca gctgagccag tgaccccccac cagcaaagca   4080 ggctcaggtg caccaggggg caccagcaag ggccccgccg aggagtccag agtgaggagg   4140
cacaagcact cctctgagtc gccagggagg acaagggga aattgtccag gctcaaacct   4200
gccccgccgc ccccaccagc agcctctgca gggaaggctg gaggaaagcc ctcgcagagc   4260
ccgagccagg aggcggccgg ggaggcagtc ctgggcgcaa agacaaaagc cacgagtctg   4320
gttgatgctg tgaacagtga cgctgccaag cccagccagc cggagagggg cctcaaaaag   4380
cccgtgctcc cggccactcc aaaagccacag tccgccaagc cgtcggggac ccccatcagc   4440
ccagcccccg ttccctccac gttgccatca gcatcctcgg ccctggcagg gaccagccg    4500 tcttccaccg ccttcatccc tctcatatca acccgagtgt ctcttcggaa aacccgccag   4560
cctccagagc ggatcgccag cggcgccatc accaagggcg tggtcctgga cagcaccgag   4620
gcgctgtgcc tcgccatctc taggaactcc gagcagatgg ccagccacag cgcagtgctg   4680
gaggccggca aaaacctcta cacgttctgc gtgagctatg tggattccat ccagcaaatg   4740
aggaacaagt ttgccttccg agaggccatc aacaaactgg agaataatct ccgggagctt   4800
cagatctgcc cggcgacagc aggcagtggt ccggcggcca ctcaggactt cagcaagctc   4860
ctcagttcgg tgaaggaaat cagtgacata gtgcagaggt ag                      4902
```

<210> SEQ ID NO 20
<211> LENGTH: 998
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ser Gly Glu Arg Asp Asp
130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Met Met
        275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Gly Gln Ser Ser Arg
            340                 345                 350

Val Ser Pro Ser Pro Thr Thr Tyr Arg Met Phe Arg Asp Lys Ser Arg
```

```
              355                 360                 365
Ser Pro Ser Gln Asn Ser Gln Gln Ser Phe Asp Ser Ser Pro Pro
    370                 375                 380
Thr Pro Gln Cys His Lys Arg His Arg His Cys Pro Val Val Ser
385                 390                 395                 400
Glu Ala Thr Ile Val Gly Val Arg Lys Thr Gly Gln Ile Trp Pro Asn
                    405                 410                 415
Asp Gly Glu Gly Ala Phe His Gly Asp Ala Asp Gly Ser Phe Gly Thr
                420                 425                 430
Pro Pro Gly Tyr Gly Cys Ala Ala Asp Arg Ala Glu Glu Gln Arg Arg
            435                 440                 445
His Gln Asp Gly Leu Pro Tyr Ile Asp Asp Ser Pro Ser Ser Ser Pro
    450                 455                 460
His Leu Ser Ser Lys Gly Arg Gly Ser Arg Asp Ala Leu Val Ser Gly
465                 470                 475                 480
Ala Leu Glu Ser Thr Lys Ala Ser Glu Leu Asp Leu Glu Lys Gly Leu
                485                 490                 495
Glu Met Arg Lys Trp Val Leu Ser Gly Ile Leu Ala Ser Glu Glu Thr
            500                 505                 510
Tyr Leu Ser His Leu Gln Met Leu Thr Asn Ser Cys Val Lys Leu Gln
        515                 520                 525
Thr Val His Ser Ile Pro Leu Thr Ile Asn Lys Glu Glu Ala Leu Gln
530                 535                 540
Arg Pro Val Ala Ser Asp Phe Glu Pro Gln Gly Leu Ser Glu Ala Ala
545                 550                 555                 560
Arg Trp Asn Ser Lys Glu Asn Leu Leu Ala Gly Pro Ser Glu Asn Asp
                565                 570                 575
Pro Asn Leu Phe Val Ala Leu Tyr Asp Phe Val Ala Ser Gly Asp Asn
            580                 585                 590
Thr Leu Ser Ile Thr Lys Gly Glu Lys Leu Arg Val Leu Gly Tyr Asn
        595                 600                 605
His Asn Gly Glu Trp Cys Glu Ala Gln Thr Lys Asn Gly Gln Gly Trp
    610                 615                 620
Val Pro Ser Asn Tyr Ile Thr Pro Val Asn Ser Leu Glu Lys His Ser
625                 630                 635                 640
Trp Tyr His Gly Pro Val Ser Arg Asn Ala Ala Glu Tyr Leu Leu Ser
                645                 650                 655
Ser Gly Ile Asn Gly Ser Phe Leu Val Arg Glu Ser Glu Ser Ser Pro
            660                 665                 670
Gly Gln Arg Ser Ile Ser Leu Arg Tyr Glu Gly Arg Val Tyr His Tyr
        675                 680                 685
Arg Ile Asn Thr Ala Ser Asp Gly Lys Leu Tyr Val Ser Ser Glu Ser
    690                 695                 700
Arg Phe Asn Thr Leu Ala Glu Leu Val His His Ser Thr Val Ala
705                 710                 715                 720
Asp Gly Leu Ile Thr Thr Leu His Tyr Pro Ala Pro Lys Arg Asn Lys
                725                 730                 735
Pro Thr Val Tyr Gly Val Ser Pro Asn Tyr Asp Lys Trp Glu Met Glu
                740                 745                 750
Arg Thr Asp Ile Thr Met Lys His Lys Leu Gly Gly Gly Gln Tyr Gly
            755                 760                 765
Glu Val Tyr Glu Gly Val Trp Lys Lys Tyr Ser Leu Thr Val Ala Val
        770                 775                 780
```

-continued

Lys Thr Leu Lys Glu Asp Thr Met Glu Val Glu Glu Phe Leu Lys Glu
785                 790                 795                 800

Ala Ala Val Met Lys Glu Ile Lys His Pro Asn Leu Val Gln Leu Leu
            805                 810                 815

Gly Val Cys Thr Arg Glu Pro Pro Phe Tyr Ile Ile Thr Glu Phe Met
        820                 825                 830

Thr Tyr Gly Asn Leu Leu Asp Tyr Leu Arg Glu Cys Asn Arg Gln Glu
    835                 840                 845

Val Asn Ala Val Val Leu Leu Tyr Met Ala Thr Gln Ile Ser Ser Ala
850                 855                 860

Met Glu Tyr Leu Glu Lys Lys Asn Phe Ile His Arg Asp Leu Ala Ala
865                 870                 875                 880

Arg Asn Cys Leu Val Gly Glu Asn His Leu Val Lys Val Ala Asp Phe
                885                 890                 895

Gly Leu Ser Arg Leu Met Thr Gly Asp Thr Tyr Thr Ala His Ala Gly
            900                 905                 910

Ala Lys Phe Pro Ile Lys Trp Thr Ala Pro Glu Ser Leu Ala Tyr Asn
        915                 920                 925

Lys Phe Ser Ile Lys Ser Asp Val Trp Ala Phe Gly Val Leu Leu Trp
    930                 935                 940

Glu Ile Ala Thr Tyr Gly Met Ser Pro Tyr Pro Gly Ile Asp Leu Ser
945                 950                 955                 960

Gln Val Tyr Glu Leu Leu Glu Lys Asp Tyr Arg Met Glu Arg Pro Glu
                965                 970                 975

Gly Cys Pro Glu Lys Val Tyr Glu Leu Met Arg Ala Tyr Phe Asp Asn
            980                 985                 990

Arg Glu Glu Arg Thr Arg
        995

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caagtggttc tccccctacca                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgtctgggca tttggagtat                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
tcaaaggctt ggtggatttc                                                    20
```

<210> SEQ ID NO 24
<211> LENGTH: 1130
<212> TYPE: PRT
<213> ORGANISM: Homo sapiens

<400> SEQUENCE: 24

| Met | Leu | Glu | Ile | Cys | Leu | Lys | Leu | Val | Gly | Cys | Lys | Ser | Lys | Lys | Gly |
|---|---|---|---|---|---|---|---|---|---|---|---|---|---|---|---|
| 1 | | | | 5 | | | | | 10 | | | | | 15 | |

| Leu | Ser | Ser | Ser | Ser | Cys | Tyr | Leu | Glu | Glu | Ala | Leu | Gln | Arg | Pro |
|---|---|---|---|---|---|---|---|---|---|---|---|---|---|---|
| | | | 20 | | | | | 25 | | | | | 30 | |

| Val | Ala | Ser | Asp | Phe | Glu | Pro | Gln | Gly | Leu | Ser | Glu | Ala | Ala | Arg | Trp |
|---|---|---|---|---|---|---|---|---|---|---|---|---|---|---|---|
| | | | 35 | | | | | 40 | | | | | 45 | | |

| Asn | Ser | Lys | Glu | Asn | Leu | Leu | Ala | Gly | Pro | Ser | Glu | Asn | Asp | Pro | Asn |
|---|---|---|---|---|---|---|---|---|---|---|---|---|---|---|---|
| | 50 | | | | | 55 | | | | | 60 | | | | |

| Leu | Phe | Val | Ala | Leu | Tyr | Asp | Phe | Val | Ala | Ser | Gly | Asp | Asn | Thr | Leu |
|---|---|---|---|---|---|---|---|---|---|---|---|---|---|---|---|
| 65 | | | | | 70 | | | | | 75 | | | | | 80 |

| Ser | Ile | Thr | Lys | Gly | Glu | Lys | Leu | Arg | Val | Leu | Gly | Tyr | Asn | His | Asn |
|---|---|---|---|---|---|---|---|---|---|---|---|---|---|---|---|
| | | | | 85 | | | | | 90 | | | | | 95 | |

| Gly | Glu | Trp | Cys | Glu | Ala | Gln | Thr | Lys | Asn | Gly | Gln | Gly | Trp | Val | Pro |
|---|---|---|---|---|---|---|---|---|---|---|---|---|---|---|---|
| | | | 100 | | | | | 105 | | | | | 110 | | |

| Ser | Asn | Tyr | Ile | Thr | Pro | Val | Asn | Ser | Leu | Glu | Lys | His | Ser | Trp | Tyr |
|---|---|---|---|---|---|---|---|---|---|---|---|---|---|---|---|
| | | | 115 | | | | | 120 | | | | | 125 | | |

| His | Gly | Pro | Val | Ser | Arg | Asn | Ala | Ala | Glu | Tyr | Pro | Leu | Ser | Ser | Gly |
|---|---|---|---|---|---|---|---|---|---|---|---|---|---|---|---|
| | 130 | | | | | 135 | | | | | 140 | | | | |

| Ile | Asn | Gly | Ser | Phe | Leu | Val | Arg | Glu | Ser | Glu | Ser | Ser | Pro | Ser | Gln |
|---|---|---|---|---|---|---|---|---|---|---|---|---|---|---|---|
| 145 | | | | | 150 | | | | | 155 | | | | | 160 |

| Arg | Ser | Ile | Ser | Leu | Arg | Tyr | Glu | Gly | Arg | Val | Tyr | His | Tyr | Arg | Ile |
|---|---|---|---|---|---|---|---|---|---|---|---|---|---|---|---|
| | | | | 165 | | | | | 170 | | | | | 175 | |

| Asn | Thr | Ala | Ser | Asp | Gly | Lys | Leu | Tyr | Val | Ser | Ser | Glu | Ser | Arg | Phe |
|---|---|---|---|---|---|---|---|---|---|---|---|---|---|---|---|
| | | | 180 | | | | | 185 | | | | | 190 | | |

| Asn | Thr | Leu | Ala | Glu | Leu | Val | His | His | Ser | Thr | Val | Ala | Asp | Gly |
|---|---|---|---|---|---|---|---|---|---|---|---|---|---|---|
| | | 195 | | | | | 200 | | | | | 205 | | |

| Leu | Ile | Thr | Thr | Leu | His | Tyr | Pro | Ala | Pro | Lys | Arg | Asn | Lys | Pro | Thr |
|---|---|---|---|---|---|---|---|---|---|---|---|---|---|---|---|
| | 210 | | | | | 215 | | | | | 220 | | | | |

| Val | Tyr | Gly | Val | Ser | Pro | Asn | Tyr | Asp | Lys | Trp | Glu | Met | Glu | Arg | Thr |
|---|---|---|---|---|---|---|---|---|---|---|---|---|---|---|---|
| 225 | | | | | 230 | | | | | 235 | | | | | 240 |

| Asp | Ile | Thr | Met | Lys | His | Lys | Leu | Gly | Gly | Gln | Tyr | Gly | Glu | Val |
|---|---|---|---|---|---|---|---|---|---|---|---|---|---|---|
| | | | | 245 | | | | | 250 | | | | | 255 |

| Tyr | Glu | Gly | Val | Trp | Lys | Lys | Tyr | Ser | Leu | Thr | Val | Ala | Val | Lys | Thr |
|---|---|---|---|---|---|---|---|---|---|---|---|---|---|---|---|
| | | | 260 | | | | | 265 | | | | | 270 | | |

| Leu | Lys | Glu | Asp | Thr | Met | Glu | Val | Glu | Glu | Phe | Leu | Lys | Glu | Ala | Ala |
|---|---|---|---|---|---|---|---|---|---|---|---|---|---|---|---|
| | | | 275 | | | | | 280 | | | | | 285 | | |

| Val | Met | Lys | Glu | Ile | Lys | His | Pro | Asn | Leu | Val | Gln | Leu | Leu | Gly | Val |
|---|---|---|---|---|---|---|---|---|---|---|---|---|---|---|---|
| | 290 | | | | | 295 | | | | | 300 | | | | |

| Cys | Thr | Arg | Glu | Pro | Pro | Phe | Tyr | Ile | Ile | Thr | Glu | Phe | Met | Thr | Tyr |
|---|---|---|---|---|---|---|---|---|---|---|---|---|---|---|---|
| 305 | | | | | 310 | | | | | 315 | | | | | 320 |

| Gly | Asn | Leu | Leu | Asp | Tyr | Leu | Arg | Glu | Cys | Asn | Arg | Gln | Glu | Val | Asn |
|---|---|---|---|---|---|---|---|---|---|---|---|---|---|---|---|
| | | | | 325 | | | | | 330 | | | | | 335 | |

| Ala | Val | Val | Leu | Leu | Tyr | Met | Ala | Thr | Gln | Ile | Ser | Ser | Ala | Met | Glu |
|---|---|---|---|---|---|---|---|---|---|---|---|---|---|---|---|
| | | | 340 | | | | | 345 | | | | | 350 | | |

| Tyr | Leu | Glu | Lys | Lys | Asn | Phe | Ile | His | Arg | Asp | Leu | Ala | Ala | Arg | Asn |
|---|---|---|---|---|---|---|---|---|---|---|---|---|---|---|---|
| | | | 355 | | | | | 360 | | | | | 365 | | |

```
Cys Leu Val Gly Glu Asn His Leu Val Lys Val Ala Asp Phe Gly Leu
    370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415

Ser Ile Lys Ser Asp Val Trp Ala Phe Gly Val Leu Leu Trp Glu Ile
                420                 425                 430

Ala Thr Tyr Gly Met Ser Pro Tyr Pro Gly Ile Asp Arg Ser Gln Val
            435                 440                 445

Tyr Glu Leu Leu Glu Lys Asp Tyr Arg Met Lys Arg Pro Glu Gly Cys
    450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
                485                 490                 495

Phe Gln Glu Ser Ser Ile Ser Asp Glu Val Glu Lys Glu Leu Gly Lys
                500                 505                 510

Gln Gly Val Arg Gly Ala Val Thr Thr Leu Leu Gln Ala Pro Glu Leu
            515                 520                 525

Pro Thr Lys Thr Arg Thr Ser Arg Arg Ala Ala Glu His Arg Asp Thr
530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
            580                 585                 590

Lys Asp Lys Lys Thr Asn Leu Phe Ser Ala Leu Ile Lys Lys Lys Lys
    595                 600                 605

Lys Thr Ala Pro Thr Pro Pro Lys Arg Ser Ser Ser Phe Arg Glu Met
610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
            660                 665                 670

Leu Arg Glu Ser Gly Gly Ser Gly Phe Arg Ser Pro His Leu Trp Lys
    675                 680                 685

Lys Ser Ser Thr Leu Thr Ser Ser Arg Leu Ala Thr Gly Glu Glu Glu
690                 695                 700

Gly Gly Gly Ser Ser Lys Arg Phe Leu Arg Ser Cys Ser Val Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
            740                 745                 750

Gly Gly His Lys Ser Glu Lys Pro Ala Leu Pro Arg Lys Arg Ala Gly
    755                 760                 765

Glu Asn Arg Ser Asp Gln Val Thr Arg Gly Thr Val Thr Pro Pro Pro
770                 775                 780
```

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
            805                 810                 815

Pro Leu Arg Arg Gln Val Thr Val Ala Pro Ala Ser Gly Leu Pro His
        820                 825                 830

Lys Glu Glu Ala Trp Lys Gly Ser Ala Leu Gly Thr Pro Ala Ala Ala
    835                 840                 845

Glu Pro Val Thr Pro Thr Ser Lys Ala Gly Ser Gly Ala Pro Arg Gly
850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Lys Leu Lys
                885                 890                 895

Pro Ala Pro Pro Pro Pro Ala Ala Ser Ala Gly Lys Ala Gly Gly
                    900                 905                 910

Lys Pro Ser Gln Arg Pro Gly Gln Glu Ala Ala Gly Glu Ala Val Leu
        915                 920                 925

Gly Ala Lys Thr Lys Ala Thr Ser Leu Val Asp Ala Val Asn Ser Asp
930                 935                 940

Ala Ala Lys Pro Ser Gln Pro Ala Glu Gly Leu Lys Lys Pro Val Leu
945                 950                 955                 960

Pro Ala Thr Pro Lys Pro His Pro Ala Lys Pro Ser Gly Thr Pro Ile
                965                 970                 975

Ser Pro Ala Pro Val Pro Leu Ser Thr Leu Pro Ser Ala Ser Ser Ala
            980                 985                 990

Leu Ala Gly Asp Gln Pro Ser Ser  Thr Ala Phe Ile Pro  Leu Ile Ser
            995                 1000                 1005

Thr Arg  Val Ser Leu Arg Lys  Thr Arg Gln Pro Pro  Glu Arg Ala
    1010                  1015                  1020

Ser Gly  Ala Ile Thr Lys Gly  Val Val Leu Asp Ser  Thr Glu Ala
    1025                  1030                  1035

Leu Cys  Leu Ala Ile Ser Gly  Asn Ser Glu Gln Met  Ala Ser His
    1040                  1045                  1050

Ser Ala  Val Leu Glu Ala Gly  Lys Asn Leu Tyr Thr  Phe Cys Val
    1055                  1060                  1065

Ser Tyr  Val Asp Ser Ile Gln  Gln Met Arg Asn Lys  Phe Ala Phe
    1070                  1075                  1080

Arg Glu  Ala Ile Asn Lys Leu  Glu Asn Asn Leu Arg  Glu Leu Gln
    1085                  1090                  1095

Ile Cys  Pro Ala Ser Ala Gly  Ser Gly Pro Ala Ala  Thr Gln Asp
    1100                  1105                  1110

Phe Ser  Lys Leu Leu Ser Ser  Val Lys Glu Ile Ser  Asp Ile Val
    1115                  1120                  1125

Gln Arg
    1130

<210> SEQ ID NO 25
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Met Leu Glu Ile Cys Leu Lys Leu Val Gly Cys Lys Ser Lys Lys Gly
1               5                   10                  15

Leu Ser Ser Ser Ser Cys Tyr Leu Glu Ala Leu Gln Arg Pro
            20                  25              30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
        50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
                100                 105                 110

Ser Asn Tyr Ile Thr Pro Val Asn Ser Leu Glu Lys His Ser Trp Tyr
            115                 120                 125

His Gly Pro Val Ser Arg Asn Ala Ala Glu Tyr Pro Leu Ser Ser Gly
        130                 135                 140

Ile Asn Gly Ser Phe Leu Val Arg Glu Ser Glu Ser Ser Pro Ser Gln
145                 150                 155                 160

Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
            195                 200                 205

Leu Ile Thr Thr Leu His Tyr Pro Ala Pro Lys Arg Asn Lys Pro Thr
        210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gly Gln Tyr Gly Glu Val
                245                 250                 255

Tyr Glu Gly Val Trp Lys Lys Tyr Ser Leu Thr Val Ala Val Lys Thr
                260                 265                 270

Leu Lys Glu Asp Thr Met Glu Val Glu Glu Phe Leu Lys Glu Ala Ala
            275                 280                 285

Val Met Lys Glu Ile Lys His Pro Asn Leu Val Gln Leu Leu Gly Val
        290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
            340                 345                 350

Tyr Leu Glu Lys Lys Asn Phe Ile His Arg Asp Leu Ala Ala Arg Asn
        355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
                405                 410                 415
```

Ser Ile Lys Ser Asp Val Trp Ala Phe Gly Val Leu Leu Trp Glu Ile
              420                 425                 430

Ala Thr Tyr Gly Met Ser Pro Tyr Pro Gly Ile Asp Arg Ser Gln Val
          435                 440                 445

Tyr Glu Leu Leu Glu Lys Asp Tyr Arg Met Lys Arg Pro Glu Gly Cys
      450                 455                 460

Pro Glu Lys Val Tyr Glu Leu Met Arg Ala Tyr Phe Asp Asn Arg Glu
465                 470                 475                 480

Glu Arg Thr Arg

<210> SEQ ID NO 26
<211> LENGTH: 4937
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

| | | | | | |
|---|---|---|---|---|---|
| atggtggacc | cggtgggctt | cgcggaggcg | tggaaggcgc | agttcccgga | ctcagagccc | 60 |
| ccgcgcatgg | agctgcgctc | agtgggcgac | atcgagcagg | agctgagcg | ctgcaaggcc | 120 |
| tccattcggc | gcctggagca | ggaggtgaac | caggagcgct | tccgcatgat | ctacctgcag | 180 |
| acgttgctgg | ccaaggaaaa | gaagagctat | gaccggcagc | gatggggctt | ccggcgcgcg | 240 |
| gcgcaggccc | ccgacggcgc | ctccgagccc | cgagcgtccg | cgtcgcgccc | gcagccagcg | 300 |
| cccgccgacg | gagccgaccc | gccgcccgcc | gaggagcccg | aggccggcc | cgacggcgag | 360 |
| ggttctccgg | gtaaggccag | gcccgggacc | gcccgcaggc | ccggggcagc | cgcgtcgggg | 420 |
| gaacgggacg | accggggacc | ccccgccagc | gtggcggcgc | tcaggtccaa | cttcgagcgg | 480 |
| atccgcaagg | ccatggcca | gccgggggcg | gacgccgaga | gcccttcta | cgtgaacgtc | 540 |
| gagtttcacc | acgagcgcgg | cctggtgaag | gtcaacgaca | agaggtgtc | ggaccgcatc | 600 |
| agctccctgg | gcagccaggc | catgcagatg | gagcgcaaaa | agtcccagca | cggcgcgggc | 660 |
| tcgagcgtgg | gggatgcatc | caggcccccct | taccggggac | gctcctcgga | gagcagctgc | 720 |
| ggcgtcgacg | gcgactacga | ggacgccgag | ttgaacccc | gcttcctgaa | ggacaacctg | 780 |
| atcgacgcca | atggcggtag | caggcccccct | tggccgcccc | tggagtacca | gccctaccag | 840 |
| agcatctacg | tcgggggcat | gatggaaggg | gagggcaagg | gcccgctcct | gcgcagccag | 900 |
| agcacctctg | agcaggagaa | gcgccttacc | tggccccgca | ggtcctactc | cccccggagt | 960 |
| tttgaggatt | gcggaggcgg | ctataccccg | gactgcagct | ccaatgagaa | cctcacctcc | 1020 |
| agcgaggagg | acttctcctc | tggccagtcc | agccgcgtgt | ccccaagccc | caccacctac | 1080 |
| cgcatgttcc | gggacaaaag | ccgctctccc | tcgcagaact | cgaacagtc | cttcgacagc | 1140 |
| agcagtcccc | ccacgccgca | gtgccataag | cggcaccggc | actgcccggt | tgtcgtgtcc | 1200 |
| gaggccacca | tcgtgggcgt | ccgcaagacc | gggcagatct | ggcccaacga | tggcgagggc | 1260 |
| gccttccatg | gagacgcaga | tggctcgttc | gaacaccac | ctggatacgg | ctgcgctgca | 1320 |
| gaccgggcag | aggagcagcg | ccggcaccaa | gatgggctgc | cctacattga | tgactcgccc | 1380 |
| tcctcatcgc | ccaccctcag | cagcaagggc | aggggcagcc | gggatgcgct | ggtctcggga | 1440 |
| gccctggagt | ccactaaagc | gagtgagctg | gacttggaaa | agggcttgga | gatgagaaaa | 1500 |
| tgggtcctgt | cgggaatcct | ggctagcgag | gagacttacc | tgagccacct | ggaggcactg | 1560 |
| ctgctgccca | tgaagcctt | gaaagccgct | gccaccacct | ctcagccggt | gctgacgagt | 1620 |

-continued

```
cagcagatcg agaccatctt cttcaaagtg cctgagctct acgagatcca aaggagttc      1680
tatgatgggc tcttcccccg cgtgcagcag tggagccacc agcagcgggt gggcgacctc      1740
ttccagaagc tggccagcca gctgggtgtg taccgggtct taggctataa tcacaatggg      1800
gaatggtgtg aagcccaaac caaaaatggc caaggctggg tcccaagcaa ctacatcacg      1860
ccagtcaaca gtctggagaa acactcctgg taccatgggc ctgtgtcccg caatgccgct      1920
gagtatctgc tgagcagcgg gatcaatggc agcttcttgg tgcgtgagag tgagagcagt      1980
cctggccaga ggtccatctc gctgagatac gaagggaggg tgtaccatta caggatcaac      2040
actgcttctg atggcaagct ctacgtctcc tccgagagcc gcttcaacac cctggccgag      2100
ttggttcatc atcattcaac ggtggccgac gggctcatca ccacgctcca ttatccagcc      2160
ccaaagcgca caagcccac tgtctatggt gtgtccccca actacgacaa gtgggagatg      2220
gaacgcacgg acatcaccat gaagcacaag ctgggcgggg gccagtacgg ggaggtgtac      2280
gagggcgtgt ggaagaaata cagcctgacg gtggccgtga agaccttgaa ggaggacacc      2340
atggaggtgg aagagttctt gaaagaagct gcagtcatga aagagatcaa acaccctaac      2400
ctggtgcagc tccttgggt ctgcacccgg gagcccccgt tctatatcat cactgagttc      2460
atgacctacg gaacctcct ggactacctg agggagtgca accggcagga ggtgaacgcc      2520
gtggtgctgc tgtacatggc cactcagatc tcgtcagcca tggagtacct ggagaagaaa      2580
aacttcatcc acagagatct tgctgcccga aactgcctgg taggggagaa ccacttggtg      2640
aaggtagctg atttttggcct gagcaggttg atgacagggg acacctacac agcccatgct      2700
ggagccaagt tccccatcaa atggactgca cccgagagcc tggcctacaa caagttctcc      2760
atcaagtccg acgtctgggc atttggagta ttgctttggg aaattgctac ctatggcatg      2820
tccccttacc cgggaattga cctgtcccag gtgtatgagc tgctagagaa ggactaccgc      2880
atggagcgcc cagaaggctg cccagagaag gtctatgaac tcatgcgagc atactttgat      2940
aaccgtgaag aaagaacaag atagaaggtt ggcagtggaa tccctctgac cggccctcct      3000
ttgctgaaat ccaccaagcc tttgaaacaa tgttccagga atccagtatc tcagacgaag      3060
tggaaaagga gctggggaaa caaggcgtcc gtggggctgt gagtaccttg ctgcaggccc      3120
cagagctgcc caccaagacg aggacctcca ggagagctgc agagcacaga gacaccactg      3180
acgtgcctga gatgcctcac tccaagggcc agggagagag cgatcctctg gaccatgagc      3240
ctgccgtgtc tccattgctc cctcgaaaag agcgaggtcc cccggagggc ggcctgaatg      3300
aagatgagcg ccttctcccc aaagacaaaa agaccaactt gttcagcgcc ttgatcaaga      3360
agaagaagaa gacagcccca acccctccca aacgcagcag ctccttccgg gagatggacg      3420
gccagccgga gcgcagaggg gccggcgagg aagagggccg agacatcagc aacgggggca      3480
tggctttcac ccccttggac acagctgacc cagccaagtc cccaaagccc agcaatgggg      3540
ctggggtccc caatggagcc ctccgggagt ccggggggctc aggcttccgg tctccccacc      3600
tgtggaagaa gtccagcacg ctgaccagca gccgcctagc caccggcgag gaggagggcg      3660
gtggcagctc cagcaagcgc ttcctgcgct cttgctccgc ctcctgcgtt cccatggggg      3720
ccaaggacac ggagtggagg tcagtcacgc tgcctcggga cttgcagtcc acggaaagac      3780
agtttgactc gtccacattt ggagggcaca aaagtgagaa gccggctctg cctcggaaga      3840
gggcagggga gaacaggtct gaccaggtga cccgaggcac agtaacgcct ccccccaggc      3900
tggtgaaaaa gaatgaggaa gctgctgatg aggtcttcaa agacatcatg gagtccagcc      3960
cgggctccag cccgcccaac ctgactccaa aacccctccg gcggcaggtc accgtggccc      4020
```

```
ctgcctcggg cctcccccac aaggaagaag ctggaaaggg cagtgcctta gggacccctg    4080
ctgcagctga gccagtgacc cccaccagca aagcaggctc aggtgcacca gggggcacca    4140
gcaagggccc cgccgaggag tccagagtga ggaggcacaa gcactcctct gagtcgccag    4200
ggagggacaa ggggaaattg tccaggctca aacctgcccc gccgccccca ccagcagcct    4260
ctgcagggaa ggctggagga aagccctcgc agagcccgag ccaggaggcg gccggggagg    4320
cagtcctggg cgcaaagaca aaagccacga gtctggttga tgctgtgaac agtgacgctg    4380
ccaagcccag ccagccggga gagggcctca aaaagcccgt gctcccggcc actccaaagc    4440
cacagtccgc caagccgtcg ggacccccca tcagcccagc cccgttcccc tccacgttgc    4500
catcagcatc ctcggccctg cagggggacc agccgtcttc caccgccttc atccctctca    4560
tatcaacccg agtgtctctt cggaaaaccc gccagcctcc agagcggatc gccagcggcg    4620
ccatcaccaa gggcgtggtc ctggacagca ccgaggcgct gtgcctcgcc atctctagga    4680
actccgagca gatggccagc cacagcgcag tgctggaggc cggcaaaaac ctctacacgt    4740
tctgcgtgag ctatgtggat ccatccagc aaatgaggaa caagtttgcc ttccgagagg     4800
ccatcaacaa actggagaat aatctcccgg gagcttcagat ctgcccggcg acagcaggca    4860
gtggtccggc ggccactcag gacttcagca agctcctcag ttcggtgaag gaaatcagtg    4920
acatagtgca gaggtag                                                  4937

<210> SEQ ID NO 27
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaactcatgc gagcatactt tgataaccgt gaagaaagaa caagatagaa ggttggcagt    60
ggaatc                                                              66

<210> SEQ ID NO 28
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gattccactg ccaaccttct atcttgttct ttcttcacgg ttatcaaagt atgctcgcat    60
gagttc                                                              66

<210> SEQ ID NO 29
<211> LENGTH: 274
<212> TYPE: PRT
<213> ORGANISM: Homo sapiens

<400> SEQUENCE: 29

Met Asp Pro Ser Ser Pro Asn Tyr Asp Lys Trp Glu Met Glu Arg Thr
1               5                   10                  15

Asp Ile Thr Met Lys His Lys Leu Gly Gly Gly Gln Tyr Gly Glu Val
            20                  25                  30

Tyr Glu Gly Val Trp Lys Lys Tyr Ser Leu Thr Val Ala Val Lys Thr
        35                  40                  45
```

```
Leu Lys Glu Asp Thr Met Glu Val Glu Glu Phe Leu Lys Glu Ala Ala
 50                  55                  60

Val Met Lys Glu Ile Lys His Pro Asn Leu Val Gln Leu Leu Gly Val
 65                  70                  75                  80

Cys Thr Arg Glu Pro Pro Phe Tyr Ile Ile Thr Glu Phe Met Thr Tyr
                 85                  90                  95

Gly Asn Leu Leu Asp Tyr Leu Arg Glu Cys Asn Arg Gln Glu Val Ser
                100                 105                 110

Ala Val Val Leu Leu Tyr Met Ala Thr Gln Ile Ser Ser Ala Met Glu
            115                 120                 125

Tyr Leu Glu Lys Lys Asn Phe Ile His Arg Asp Leu Ala Ala Arg Asn
 130                 135                 140

Cys Leu Val Gly Glu Asn His Leu Val Lys Val Ala Asp Phe Gly Leu
145                 150                 155                 160

Ser Arg Leu Met Thr Gly Asp Thr Tyr Thr Ala His Ala Gly Ala Lys
                165                 170                 175

Phe Pro Ile Lys Trp Thr Ala Pro Glu Ser Leu Ala Tyr Asn Lys Phe
                180                 185                 190

Ser Ile Lys Ser Asp Val Trp Ala Phe Gly Val Leu Leu Trp Glu Ile
                195                 200                 205

Ala Thr Tyr Gly Met Ser Pro Tyr Pro Gly Ile Asp Leu Ser Gln Val
 210                 215                 220

Tyr Glu Leu Leu Glu Lys Asp Tyr Arg Met Glu Arg Pro Glu Gly Cys
225                 230                 235                 240

Pro Glu Lys Val Tyr Glu Leu Met Arg Ala Cys Trp Gln Trp Asn Pro
                245                 250                 255

Ser Asp Arg Pro Ser Phe Ala Glu Ile His Gln Ala Phe Glu Thr Met
                260                 265                 270

Phe Gln

<210> SEQ ID NO 30
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Asp Pro Ser Ser Pro Asn Tyr Asp Lys Trp Glu Met Glu Arg Thr
 1               5                  10                  15

Asp Ile Thr Met Lys His Lys Leu Gly Gly Gly Gln Tyr Gly Glu Val
                 20                  25                  30

Tyr Glu Gly Val Trp Lys Lys Tyr Ser Leu Thr Val Ala Val Lys Thr
             35                  40                  45

Leu Lys Glu Asp Thr Met Glu Val Glu Glu Phe Leu Lys Glu Ala Ala
 50                  55                  60

Val Met Lys Glu Ile Lys His Pro Asn Leu Val Gln Leu Leu Gly Val
 65                  70                  75                  80

Cys Thr Arg Glu Pro Pro Phe Tyr Ile Ile Thr Glu Phe Met Thr Tyr
                 85                  90                  95

Gly Asn Leu Leu Asp Tyr Leu Arg Glu Cys Asn Arg Gln Glu Val Ser
                100                 105                 110

Ala Val Val Leu Leu Tyr Met Ala Thr Gln Ile Ser Ser Ala Met Glu
            115                 120                 125
```

-continued

```
Tyr Leu Glu Lys Lys Asn Phe Ile His Arg Asp Leu Ala Ala Arg Asn
    130                 135                 140

Cys Leu Val Gly Glu Asn His Leu Val Lys Val Ala Asp Phe Gly Leu
145                 150                 155                 160

Ser Arg Leu Met Thr Gly Asp Thr Tyr Thr Ala His Ala Gly Ala Lys
                165                 170                 175

Phe Pro Ile Lys Trp Thr Ala Pro Glu Ser Leu Ala Tyr Asn Lys Phe
            180                 185                 190

Ser Ile Lys Ser Asp Val Trp Ala Phe Gly Val Leu Leu Trp Glu Ile
        195                 200                 205

Ala Thr Tyr Gly Met Ser Pro Tyr Pro Gly Ile Asp Leu Ser Gln Val
    210                 215                 220

Tyr Glu Leu Leu Glu Lys Asp Tyr Arg Met Glu Arg Pro Glu Gly Cys
225                 230                 235                 240

Pro Glu Lys Val Tyr Glu Leu Met Arg Ala Tyr Phe Asp Asn Arg Glu
                245                 250                 255

Glu Arg Thr Arg
            260
```